United States Patent
Datta et al.

(10) Patent No.: US 9,050,176 B2
(45) Date of Patent: Jun. 9, 2015

(54) AT LEAST PARTIALLY RESORBABLE RETICULATED ELASTOMERIC MATRIX ELEMENTS AND METHODS OF MAKING SAME

(75) Inventors: Arindam Datta, Hillsborough, NJ (US); Lawrence P. Lavelle, Rahway, NJ (US); Craig Friedman, Santa Fe, NM (US); Balakrishna Haridas, Mason, OH (US)

(73) Assignee: BIOMERIX CORPORATION, New York, NY (US)

( * ) Notice: Subject to any disclaimer, the term of this patent is extended or adjusted under 35 U.S.C. 154(b) by 601 days.

(21) Appl. No.: 13/352,276

(22) Filed: Jan. 17, 2012

(65) Prior Publication Data
US 2012/0239161 A1  Sep. 20, 2012

Related U.S. Application Data

(63) Continuation-in-part of application No. 12/798,511, filed on Apr. 5, 2010, now Pat. No. 8,801,801.

(60) Provisional application No. 61/166,687, filed on Apr. 3, 2009, provisional application No. 61/433,136, filed on Jan. 14, 2011.

(51) Int. Cl.
*A61F 2/02* (2006.01)
*A61L 27/18* (2006.01)
(Continued)

(52) U.S. Cl.
CPC . *A61F 2/02* (2013.01); *A61L 27/18* (2013.01); *A61L 27/56* (2013.01); *A61L 27/58* (2013.01);
(Continued)

(58) Field of Classification Search
CPC ......... A61L 27/18; A61L 27/58; A61L 27/05; C08L 101/16; C08G 18/4277; C08G 18/6611; C08G 18/2063; C08G 18/3206; C08G 18/7671; C08G 18/1833; C08G 2101/005; C08G 2101/0083
USPC ............. 623/1.36, 1.39, 1.4, 1.41, 1.46, 1.49, 623/11.11, 14.12, 15.12, 23.72, 23.75, 623/23.76; 424/422, 424, 425; 52/50, 52, 52/117, 170, 172, 173
See application file for complete search history.

(56) References Cited

U.S. PATENT DOCUMENTS

| | | |
|---|---|---|
| 5,133,755 A | 7/1992 | Brekke |
| 5,514,378 A | 5/1996 | Mikos et al. |

(Continued)

FOREIGN PATENT DOCUMENTS

| | | |
|---|---|---|
| WO | 2004062531 A1 | 7/2004 |
| WO | 2004/074342 | 9/2004 |

(Continued)

OTHER PUBLICATIONS

International Search Report in related international application No. PCT/US10/01035, mailed Jun. 16, 2010.

(Continued)

*Primary Examiner* — Thomas McEvoy
(74) *Attorney, Agent, or Firm* — Pillsbury Winthrop Shaw Pittman LLP

(57) ABSTRACT

The present disclosure relates to reticulated elastomeric matrices, and more particularly to at least partially degradable elastomeric elements that are compressible and exhibit resilience in their recovery and that can be employed in diverse applications including, without limitation, biological implantation, especially in humans.

17 Claims, 3 Drawing Sheets

(51) Int. Cl.

| | | |
|---|---|---|
| *A61L 27/56* | (2006.01) | |
| *A61L 27/58* | (2006.01) | |
| *C08G 18/66* | (2006.01) | |
| *C08G 18/76* | (2006.01) | |
| *C08G 18/18* | (2006.01) | |
| *C08G 18/20* | (2006.01) | |
| *C08G 18/32* | (2006.01) | |
| *C08G 18/42* | (2006.01) | |
| *C08L 101/16* | (2006.01) | |
| *A61K 9/00* | (2006.01) | |
| *A61K 47/10* | (2006.01) | |
| *C08G 101/00* | (2006.01) | |

(52) U.S. Cl.
CPC .......... *A61L 2430/06* (2013.01); *A61L 2430/10* (2013.01); *A61K 9/0024* (2013.01); *A61K 47/10* (2013.01); *C08G 18/6611* (2013.01); *C08G 18/7671* (2013.01); *C08G 18/1833* (2013.01); *C08G 18/2063* (2013.01); *C08G 18/3206* (2013.01); *C08G 18/4277* (2013.01); *C08G 2101/0058* (2013.01); *C08G 2101/0083* (2013.01); *C08G 2230/00* (2013.01); *C08L 101/16* (2013.01)

(56) References Cited

U.S. PATENT DOCUMENTS

| | | | |
|---|---|---|---|
| 5,522,895 | A | 6/1996 | Mikos |
| 5,607,474 | A | 3/1997 | Athanasiou et al. |
| 5,677,355 | A | 10/1997 | Shalaby et al. |
| 5,716,413 | A | 2/1998 | Walter et al. |
| 5,769,899 | A | 6/1998 | Schwartz et al. |
| 5,770,193 | A | 6/1998 | Vacanti et al. |
| 6,177,522 | B1 | 1/2001 | Brady |
| 6,210,441 | B1 | 4/2001 | Flodin |
| 6,221,997 | B1 | 4/2001 | Woodhouse et al. |
| 6,306,424 | B1 | 10/2001 | Vyakarnam et al. |
| 6,355,699 | B1 | 3/2002 | Vyakarnam et al. |
| 6,376,742 | B1 | 4/2002 | Zdrahala et al. |
| 6,545,097 | B2 | 4/2003 | Pinchuk |
| 6,784,273 | B1 | 8/2004 | Spaans et al. |
| 6,852,330 | B2 | 2/2005 | Bowman |
| 7,264,823 | B2 | 9/2007 | Beckman et al. |
| 7,425,288 | B2 | 9/2008 | Flodin et al. |
| 7,763,077 | B2 | 7/2010 | Friedman et al. |
| 7,803,395 | B2 | 9/2010 | Datta et al. |
| 2004/0175408 | A1 | 9/2004 | Chun |
| 2005/0013793 | A1 | 1/2005 | Beckman et al. |
| 2005/0043816 | A1 | 2/2005 | Datta et al. |
| 2006/0188547 | A1 | 8/2006 | Bezwada |
| 2007/0162131 | A1 | 7/2007 | Friedman |
| 2007/0190108 | A1 | 8/2007 | Datta et al. |
| 2007/0299151 | A1 | 12/2007 | Guelcher et al. |
| 2008/0109070 | A1 | 5/2008 | Wagner et al. |
| 2009/0221784 | A1 | 9/2009 | Guelcher et al. |
| 2009/0292029 | A1 | 11/2009 | Bezwada |
| 2010/0068171 | A1 | 3/2010 | Guelcher et al. |
| 2010/0249913 | A1 | 9/2010 | Datta et al. |
| 2010/0256777 | A1 | 10/2010 | Datta et al. |
| 2010/0318108 | A1 | 12/2010 | Datta et al. |
| 2011/0184530 | A1 | 7/2011 | Datta et al. |

FOREIGN PATENT DOCUMENTS

| | | |
|---|---|---|
| WO | 2009026387 A1 | 2/2009 |
| WO | 2009/141732 | 11/2009 |

OTHER PUBLICATIONS

Vicki Rosen and R. Scott Thies, The Cellular and Molecular Basis of Bone Formation and Repair, R.G. Landes Company.
International Search Report and Written Opinion in related international application No. PCT/US2012/21623, mailed May 21, 2012.
Supplementary European Search Report in related international application No. PCT/US2010001035, dated Aug. 22, 2012.
Office Action issued on Mar. 3, 2015 in EP Application No. 10759171.1.

AT LEAST PARTIALLY RESORBABLE RETICULATED ELASTOMERIC MATRIX ELEMENTS AND METHODS OF MAKING SAME

REFERENCE TO PRIOR APPLICATIONS

This application is a Continuation-In-Part of U.S. application Ser. No. 12/798,511 filed Apr. 5, 2010, which claims benefit to U.S. Provisional Application Ser. No. 61/166,687 filed Apr. 3, 2009 both of which are incorporated herein by reference in their entireties. This application also claims priority to U.S. Provisional Application Ser. No. 61/433,136 filed Jan. 14, 2011, which is incorporated herein by reference in its entirety.

FIELD OF THE INVENTION

The present disclosure relates to reticulated elastomeric matrices, and more particularly to at least partially degradable elastomeric elements that are compressible and exhibit resilience in their recovery and that can be employed in diverse applications including, without limitation, biological implantation, especially in humans.

BACKGROUND OF THE INVENTION

There is a current need in medicine for innocuous implantable devices that can be delivered to an in vivo patient site, for example, a site in a human patient that can occupy that site for extended periods of time for healing, repair or regeneration of damaged or defective tissue without being harmful to the host. There is currently a further need for such innocuous porous polymeric implantable devices that can eventually become integrated to the damaged or defective tissue site such as to provide biointegrative repair ingrown with tissue or provide bio-integration but which is also at least partially degradable or bioabsorbable to allow for further tissue ingrowth leading to enhanced tissue augmentation and repair at the defect site.

Various tissue engineering (TE) approaches are reviewed in co-pending U.S. Patent Application Publications US 2005/0043816 (now U.S. Pat. No. 7,803,395) and US2007/0190108, U.S. 2010/0318108 and PCT application PCT/US2010/022946 filed Feb. 10, 2010. Tissue engineering generally includes the delivery of a biocompatible tissue substrate that serves as a scaffold or support onto which cells may attach, grow and/or proliferate, thereby synthesizing new tissue by regeneration or new tissue growth to repair a wound or defect. Open cell biocompatible foams with high porosity have been recognized to have significant potential for use in the repair and regeneration of tissue. Tissue engineering has also tended to focus on synthetic bioabsorbable materials because they tend to be absorbed and metabolized by the body without causing significant adverse tissue responses.

Bioabsorbable TE scaffolds have been made using various processing methods and materials such as those described in U.S. Pat. No. 5,522,895 (Mikos), U.S. Pat. No. 5,514,378 (Mikos et al.), U.S. Pat. No. 5,133,755 (Brekke), U.S. Pat. No. 5,716,413 (Walter et al.), U.S. Pat. No. 5,607,474 (Athanasiou et al.), U.S. Pat. No. 6,306,424 (Vyakarnam et. al), U.S. Pat. No. 6,355,699 (Vyakarnam et. al), U.S. Pat. No. 5,677,355 (Shalaby et al.), U.S. Pat. No. 5,770,193 (Vacanti et al.), and U.S. Pat. No. 5,769,899 (Schwartz et al.). Synthetic bioabsorbable biocompatible polymers used in the above-mentioned references are well known in the art and, in most cases, include aliphatic polyesters, homopolymers and copolymers (random, block, segmented and graft) of monomers such as glycolic acid, glycolide, lactic acid, lactide (d-, l-, meso-), ε-caprolactone, trimethylene carbonate, and p-dioxanone or mixtures thereof.

Bioabsorbable polyurethane have been made using various processing methods and materials such as those described in U.S. Pat. No. 7,425,288 (Flodin et al.) and U.S. Pat. No. 6,210,441 (Flodin), U.S. Pat. No. 6,221,997 (Woodhouse, et al), U.S. Pat. No. 6,784,273 (Spaans et. al.), US 2007/0299151 (Guelcher, et al), US 2010/0068171 (Guelcher, et al), US 2009/0221784 (Guelcher, et al), U.S. Pat. No. 7,264,823 (Beckman et al), US 2005/0013793 (Beckman et al), WO 2009/141732 (Van Beijma), WO 2004/074342 (Heijkants, et. al.), US 2010/0068171 (Guelcher, et al), US 2006/0188547 (Bezwada), and US 2009/0292029 (Bezwada).

Various polymers having varying degrees of biodurability or biodegradation are known with the hydrolytic degradation rates being controlled by forming copolymers or blends of various combination of degradable aliphatic polyester homopolymers with different degradation rates. However, some materials are undesirable in view of adverse tissue response during the product's life cycle as the polymers biodegrade. The degradation characteristics of certain materials resist engineering, thus severely limiting their ability to serve as effective scaffolds. Also, there remains a need for an implant that withstands compression in a delivery-device during delivery to a biological site, e.g., by a catheter, endoscope, arthoscope, or syringe, but is capable of expansion by resiliently recovery to occupy and remain in the biological site. Moreover, it has been difficult to engineer controlled pore sizes such that the implant becomes ingrown with tissue, in situ. Furthermore, many materials produced from polyurethane foams formed by blowing during the polymerization process are unattractive from the point of view of biodurability because undesirable materials that can produce adverse biological reactions are generated during polymerization, for example, carcinogens, cytotoxins and the like.

SUMMARY OF THE INVENTION

The present disclosure addressed many of the limitations of the prior art. For example, an embodiment relates to innocuous implantable devices that can be delivered to an in vivo patient site, for example, a site in a human patient that can occupy that site for extended periods of time for healing, repair or regeneration of damaged or defective tissue without being harmful to the host. Such innocuous porous polymeric implantable devices can eventually become integrated to the damaged or defective tissue site such as to provide biointegrative repair ingrown with tissue or provide bio-integration. Such innocuous porous polymeric implantable devices are also at least partially degradable or bioabsorbable to allow for further tissue ingrowth leading to enhanced tissue augmentation and repair at the defect site.

An embodiment relates to a substantially fully or fully resorbable reticulated scaffold having elastomeric and resilient properties with appropriate tensile and compressive properties and dynamic recovery times that would resorb in a body with short or intermediate or long degradation times.

According to an aspect, the disclosure provides a matrix comprising a biocompatible, cross-linked, biodegradable polyurethane, the matrix having a continuous-interconnected void phase, wherein the matrix is configured to be in-grown by a biological tissue. According to an aspect, the polyurethane degrades in a body of an animal to cause a loss of weight of the matrix and the resultant void phase is further ingrown and proliferated by tissues or biological tissue and in one embodiment, further ingrown and proliferated tissues can re-model to become substantially similar to the surrounding tissue in the body of an animal where it was placed. According to an aspect, the polyurethane matrix is reticulated to a Darcy permeability of at least 100 or in one embodiment, at least 150 or in another embodiment, at least 200.

According to an aspect, the elastomeric polyurethane matrix is segmented and comprises biodegradable, polyol-derived soft segments and an isocyanate-derived hard segments. According to an aspect, biodegradable, polyol-derived soft segments comprises of aliphatic polyesters whose hydrolytic degradation rates can be controlled. According to an aspect, the matrix has substantially non-crystalline isocyanate-derived hard segments. According to an aspect, the matrix has substantially non-crystalline isocyanate-derived hard segments that can optionally be further chain extended or optionally cross-linked and degree and extent of both chain extension and cross-linking can be varied to control the degradation rates of the segmented polyurethane elastomeric matrix. According to an aspect, the polyurethane matrix is optionally derived from an amount of glycerol sufficient to at least partially cross-link the isocyanate-derived hard segments. According to an aspect, the isocyanate-derived hard segments are substantially free from biuret and/or allophanate and/or isocyanurate groups.

According to an aspect of the disclosure, the isocyanate hard segment is at least partially non-crystalline. According to an aspect of the disclosure, the isocyanate hard segment is at least partially composed of 4,4-MDI and 2,4-MDI. According to an aspect of the disclosure, the 2,4-MDI is included in an amount sufficient to render the hard segment substantially non-crystalline. According to an aspect of the disclosure, the 2,4-MDI is present at from about 5% to about 50% relative to the amount of 4,4-MDI. According to an aspect of the disclosure, the isocyanate hard segment is at least partially composed of 4,4-MDI, 2,4-MDI and polymeric MDI. According to an aspect of the disclosure, MDI-derived hard segment are biostable. In one aspect of the disclosure, the isocyanate hard segment is at least partially composed of 4,4-MDI and with no polymeric MDI.

According to an aspect of the disclosure, the isocyanate hard segment is at least partially biodegradable. According to an aspect of the disclosure, the isocyanate hard segment is composed of monomers containing at least one hydrolysable bond. According to an aspect, biodegradable hard segments may be formed from an aliphatic diisocyanate is selected from the group consisting of lysine methyl ester diisocyanate, lysine triisocyanate, 1,4-diisocyanatobutane, hexamethylene diisocyanate, $H_{12}MDI$, and mixtures thereof. According to an aspect, biodegradable hard segments may be formed from an aromatic diisocyanate. is a hydrolytically-cleavable, bridged diphenyl diisocyanate. According to an aspect, the aromatic diisocyanate may be a hydrolytically-cleavable, bridged diphenyl diisocyanate.

According to an aspect of the disclosure, the at least partially biodegradeable, reticulated, elastomeric, polyurethane matrix contains soft segments derived from hydrolyzable polyols. According to an aspect of the disclosure, the polyols contain one or more tertiary carbon linkages. According to an aspect of the disclosure, the polyol soft segments will at least partially degrade. According to an aspect of the disclosure, the polyol soft segments may be derived from at least one moiety derived from the group consisting of a polyester polyol, polycaprolactone polyol, a poly(caprolactone-co-glycolide)polyol, a poly(caprolactone-co-l-lactide) polyol, a poly(caprolactone-co-d-l-lactide)polyol, poly(caprolactone-co-paradioxanone polyol poly(caprolactone-co-glycolide-co-lactide)polyol, poly(caprolactone-co-glycolide-co-d/l lactide)polyol, poly(caprolactone-co-lactide-co-d/l lactide) polyol and copolymers and mixtures thereof.

According to an aspect of the disclosure, the polyol soft segments may contain one or more tertiary carbon linkages.

According to an aspect of the disclosure, the at least partially biodegradeable, reticulated, elastomeric, polyurethane matrix has an isocyanate index less than or equal to 1.05 or in another embodiment less than 1.02.

According to an aspect of the disclosure, the at least partially biodegradeable, reticulated, elastomeric, polyurethane matrix may further contain a chain extender. According to an aspect of the disclosure, the at least partially biodegradeable, reticulated, elastomeric, polyurethane matrix may further comprise a cross-linker in addition to glycerol.

According to an aspect of the disclosure, the at least partially biodegradeable, reticulated, elastomeric, polyurethane matrix further comprising a blowing agent. The blowing agent may be water.

According to an aspect of the disclosure, the at least partially biodegradeable, reticulated, elastomeric, polyurethane matrix may further comprise at least one at least one auxiliary agent which may include surfactants, cell-openers, viscosity modifiers, blowing catalysts, and gelling catalysts.

According to an aspect, the disclosure provides methods of making the partially biodegradeable, reticulated, elastomeric, polyurethane matrix. According to an aspect, there is provided a mixture of diisocyanates that polymerize to yield non-crystalline hard segments. According to an aspect, there is provided a mixture of hydrolyzable polyols. The disclosure provides for reacting the isocyanates and polyols to form an at least partially biodegradable elastomeric polyurethane matrix such as foam. Moreover, the reaction proceeds so that the resultant matrix is substantially free of un-reacted isocyanate groups, biuret groups, allophanate groups, and/or isocyanurate group. According to an aspect, the methods further provide for reticulating the matrix to a Darcy permeability of at least 100.

According to an aspect, the disclosure provides devices made from the disclosed a partially biodegradable, reticulated, elastomeric, polyurethane matrix. According to an aspect, the devices include artificial tissues.

According to an aspect, the disclosure provides a process for preparing a biocompatible; cross-linked, biodegradable polyurethane, the matrix having a continuous-interconnected void phase, wherein said matrix is configured to be in-grown by a biological tissue the process comprising providing a biodegradable polyol having a molecular weight of at least 750, admixing an isocyanate component, wherein said isocyanate reacts to form substantially non-crystalline hard segments, admixing a glycerol cross-linker, admixing a blowing agent, and reacting said admixture to form a biocompatible, cross-linked, biodegradable polyurethane matrix.

According to an aspect of the disclosure, the at least partially biodegradeable, reticulated, elastomeric, polyurethane matrix can have a structure post foaming that can be reticulated. According to an aspect of the disclosure, the at least partially biodegradeable, reticulated, elastomeric, polyurethane matrix can have a structure post foaming that can be reticulated. According to an aspect of the disclosure, the at least partially biodegradeable, reticulated, elastomeric, polyurethane matrix can have a structure post foaming that can be thermally reticulated.

According to an aspect of the method, the elastomeric matrix is reticulated. According to an aspect of the method, the elastomeric matrix is thermally reticulated. According to an aspect of the method, the matrix is reticulated to a Darcy value of at least 100. According to an aspect of the method, the matrix is reticulated by contact with a mixture of explosive gases containing hydrogen and oxygen. According to an aspect of the method, the matrix is reticulated by detonation of the explosive gas mixture.

According to an aspect, a medical device is provided. According to an aspect, the medical device has a matrix comprising a biocompatible, cross-linked, biodegradable polyurethane, the matrix having a continuous-interconnected void phase, wherein said matrix is configured to be in-grown by a biological tissue. The continuous-interconnected void phase is termed as reticulated matrix and is interconnected and intercommunicating networks of cells, pores, and voids to permit ingrowth and proliferation of tissue into the matrix interiors or in one embodiment into the device interiors.

According to an aspect, a method of treating a tissue defect is provided. According to an aspect, the method comprises providing a medical device to an in vivo site of a tissue defect, said medical device having a matrix comprising a biocompatible, cross-linked, biodegradable polyurethane, the matrix having a continuous-interconnected void phase, wherein said matrix is configured to be in-grown by a biological tissue.

Another embodiment relates to the determination of the stoichiometric composition and processing conditions for fabrication of the various scaffold types.

Another embodiment relates to the development of the partially degradable highly porous inter-connected reticulated elastomeric urethane scaffold by a repeatable process with stable configurations that withstood thermal reticulation, preferably using PCL based polyols. Preferably, the formulations has high void content leading to high permeabilities that would allow for efficient exudate removal and provide for tissue ingrowth if used for Negative Pressure Wound Therapy NPWT.

Another embodiment relates to the development of a fully degradable highly porous formulations in producing elastomeric scaffolds with fully accessible high void content and high permeabilities that would allow for efficient exudate removal and tissue ingrowth in potential NPWT applications.

Another embodiment relates to overcoming a challenge in handling and control of the lower initial green strength of the scaffolds due to lower cross-linking and hard segment. However, this challenge was solved in that these materials would subsequently gain strength and become stronger after curing even with lower crosslinking levels as exhibited by the degradable PCL based polyols.

An embodiment relates to a partially resorbable reticulated scaffold formulation comprising (a) a non-degradable aromatic MDI having cross-linking or a non-degradable aliphatic H12MDI having cross-linking and optionally a chain extender as a hard segment and (b) a degradable PCL/PGA copolymer polyol or a degradable PCL/PLA copolymer polyol or a degradable PCL/PGA/PLA copolymer polyol or a degradable PCL/PDLA copolymer polyol or a degradable PCL polyol or their appropriate combinations as a soft segment.

An embodiment relates to a partially resorbable reticulated scaffold comprising polyurethane-urea or polyurea-urethane An embodiment relates to a partially resorbable reticulated scaffold having elastomeric and resilient properties with appropriate tensile and compressive properties and dynamic recovery times that would resorb in a body with short or intermediate or long degradation times.

An embodiment relates to a partially resorbable reticulated scaffold that is biocompatible and conducive to allow for fluid transfer, tissue ingrowth, regeneration and re-modeling with bio-integration to wound or defect site to heal tissue defect.

An embodiment relates to a process of making a partially resorbable reticulated scaffold comprising reacting (a) a non-degradable aromatic MDI having cross-linking or a non-degradable aliphatic H12MDI having cross-linking and optionally a chain extender as a hard segment and (b) a degradable PCL/PGA copolymer polyol or a degradable PCL/PLA copolymer polyol or a degradable PCL/PGA/PLA copolymer polyol or a degradable PCL/PDLA copolymer polyol or a degradable PCL polyol or their appropriate combinations as a soft segment, followed by thermal reticulation.

An embodiment relates to a substantially fully or fully resorbable reticulated scaffold formulation comprising (a) a PGA-based or PLA-based or PDS-based or PCL-based resorbable aromatic diisocyanate having cross-linking and optionally a chain extender as a hard segment and (b) a degradable PCL/PGA copolymer polyol or a degradable PCL/PLA copolymer polyol or a degradable PCL/PGA/PLA copolymer polyol or a degradable PCL/PDLA copolymer polyol or a degradable PCL polyol or their appropriate combinations as a soft segment.

An embodiment relates to a substantially fully or fully resorbable reticulated scaffold comprising polyurethane-urea or polyurea-urethane.

An embodiment relates to a substantially fully or fully resorbable reticulated scaffold that is biocompatible and conducive to allow for fluid transfer, tissue ingrowth, regeneration and re-modeling with bio-integration to wound or defect site to heal tissue defect.

Still other aspects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BRIEF DESCRIPTION OF THE DRAWINGS

Some embodiments of the invention, and of making and using the invention, are described in detail below, which description is to be read with and in the light of the foregoing description, by way of example, with reference to the accompanying drawings in which.

Figure 1:
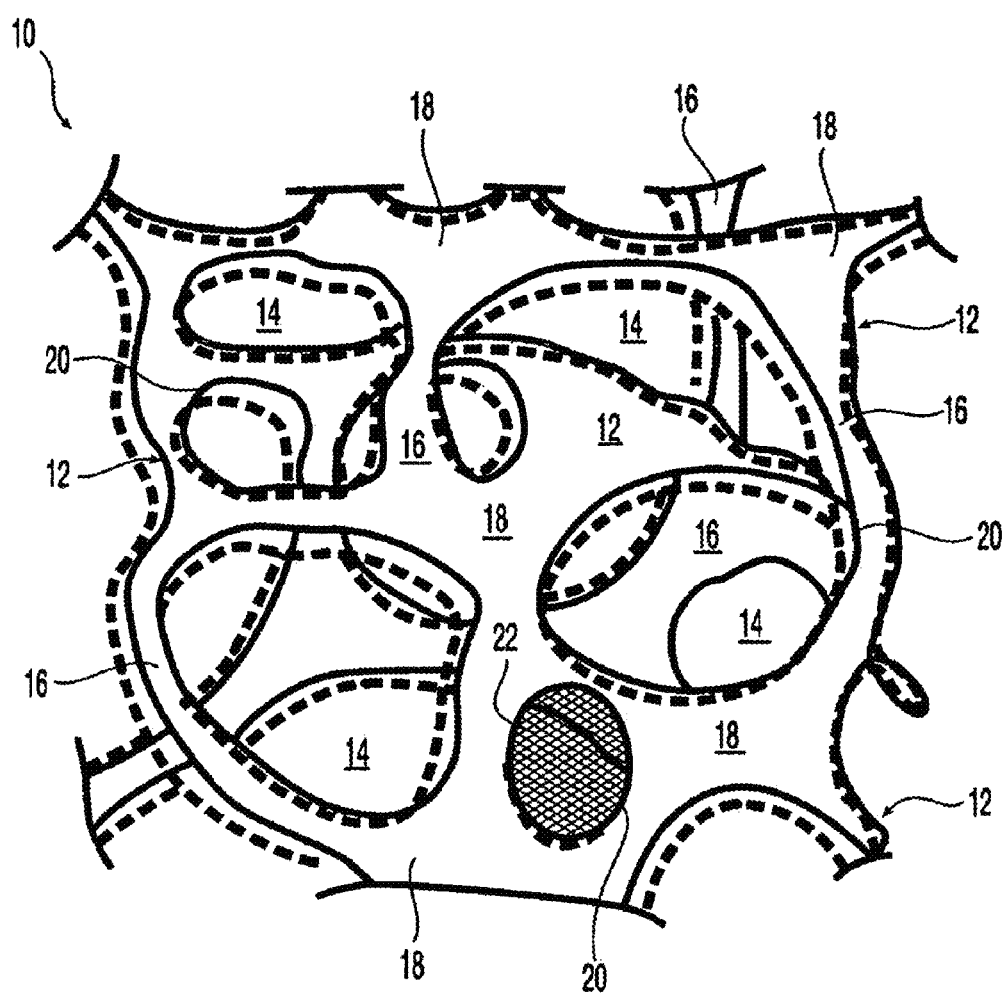
FIG. 1 is a schematic depiction of an example of a particular morphology of a reticulated matrix which illustrates some of the features and principles of the microstructure of embodiments of the invention.

It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

The present disclosure relates to a cross-linked elastomeric polyurethane matrix. The present disclosure thus differs from e.g., Flodin, U.S. Pat. No. 7,425,288, and Chun, U.S. 2004/0175408 who disclose solvent-soluble polyurethanes and from e.g., Woodhouse, U.S. Pat. No. 6,221,997 and Spaans U.S. Pat. No. 6,784,273 who discloses melt-processable and solution-castable polyurethane polymers.

The present disclosure relates to polyurethanes synthesized from high-molecular weigh polyols, e.g., polyoly having a molecular weight >300. The present disclosure differ from polyurethanes synthesized from low-molecular weight polyols. i.e., those such as disclosed by Guelcher, U.S. 2009/0221784.

The present disclosure relates to a solid cross-linked polyurethane matrix that need to be solid to undergo the thermal and mechanical shock or impact of the reticulation step that is required following foaming to remove the cell membranes formed during the foaming process and thus differs from injectable in situ forming foams as those disclosed by Guelcher, US 2007/0299151.

In preferred embodiments, the present disclosure relates to polyurethanes synthesized at low isocayanate ratios, e.g., 1.05 or 1.02 or less, thereby substantially or completely preventing the formation of allophanate, and/or biuret, and/or isocyanurate linkages. Therefore, the polyurethanes of the present disclosure differ from those such as disclosed by Brady, U.S. Pat. No. 6,177,522.

The present disclosure relates to bioabsorbable polyurethanes and thus differ from the biostable polyurethanes such as disclosed by Bowman, U.S. Pat. No. 6,852,330 and Pinchuk, U.S. Pat. No. 6,545,097.

The present disclosure relates to reticulated polyurethane foams having a continuous void phase comprising at least 75% of the total volume. The foams of the present disclosure are characterized by a Darcy permeability of at least 200. Brady, U.S. 2005/0072550 discloses a foam reticulated by crushing. Brady does not disclose a Darcy value for his foam. However, crushing does not remove the membranes between adjacent cells and pores following foaming and thus achieves low Darcy permeability values of approximately 10-15 or lower.

The present disclosure relates to a resilient, elastomeric matrix that is synthesized in the presence of a blowing agent to form a porous foam whose cells and pores are not interconnected to form a continuous void. In a subsequent process step the foam is infused with an explosive mixture, e.g., $H_2$ and $O_2$ which is ignited to reticulate the foam or create three dimensional inter-connected and inter-communicating structure with a continuous void whose pores and cells are fully or almost fully accessible by tissues and body fluids when implanted at a defect site for tissue repair or regeneration. The post-processing steps provide a matrix or scaffold that may be implanted into a body, such as a human body. Because of the biointegrative three dimensional inter-connected and inter-communicating structure characteristics of the base reticulated implantable devices, embodiments of the invention have the advantage of potentially better and faster tissue in-growth, healing, and remodeling. However, the foam differs from prior art foams that may be injected into the body. The requirement for explosive reticulation means that the matrix of this invention cannot be formed in situ, in an animal body.

Certain embodiments of the invention comprise at least partially degradable reticulated elastomeric products, which are also compressible and exhibit resilience in their recovery, that have a diversity of applications and can be employed, by way of example, in biological implantation, especially into humans, for long-term tissue engineering (TE) implants, especially where dynamic loadings and/or extensions are experienced, such as in soft tissue related applications; orthopedic applications especially in soft tissue attachment, repair and regeneration of tendons, ligaments, meniscus, spinal disc disorders, orthopedic applications especially in hard tissue or bone repair and regeneration, repair of soft tissue defects, specifically inguinal, femoral, ventral, incisional, umbilical, and epigastric hernias; surgical meshes for tissue augmentation, support and repair; wound healing and defect filling, for therapeutic purposes; for cosmetic, reconstructive, urologic or gastroesophageal purposes; or as substrates for pharmaceutically-active agents, e.g., drug, delivery. The resilience of the at least partially degradable reticulated elastomeric matrix also allows recovery if it is compressed during delivery and once it is placed in the human or animal body.

In another embodiment, least partially degradable reticulated elastomeric products such as a dressing-scaffold can be uses as an implantable dressing in Negative Pressure Wound Therapy (NPWT) for the treatment of advanced wounds such as diabetic ulcers, decubitus ulcers (pressure sores), and venous & arterial ulcers. In another embodiment, least partially degradable reticulated elastomeric products such as a bi-functional degradable dressing-scaffold biomaterial that will in the first phase function as an implantable NPWT dressing/scaffold during the early therapeutic phase, producing robust fibrovascular granulation tissue by providing an uninterrupted and unfettered medium for exudate removal and biomechanical stimulation thus eliminating the need for dressing changes which damage the nascent granulation tissue bed. In the second phase, least partially degradable reticulated elastomer products such as a bi-functional degradable dressing-scaffold biomaterial that will function as resorbable 3-dimensional tissue scaffold post NPWT to promote cell attachment, maintenance, and remodeling of neogranulation tissue created as a result of application of NPWT. The scaffold structures are either partially degradable or fully degradable through normal metabolic pathways, leaving behind a maturing and remodeling dermis and epithelialized wound. Other embodiments involve reticulated, at least partially degradable elastomer products for in vivo delivery via catheter, endoscope, arthoscope, laproscope, cystoscope, syringe or other suitable delivery-device and can be satisfactorily implanted or otherwise exposed to living tissue and fluids for extended periods of time.

There is a need in medicine, as recognized by the present invention, for innocuous implantable devices that can be delivered to an in vivo patient site, for example a site in a human patient, that can occupy that site for extended periods of time without being harmful to the host. In one embodiment, such implantable devices are allowed to eventually become integrated, such as biointegrated, e.g., ingrown with tissue or bio-integration. In one embodiment, such implantable devices can at least partially degrade or bioabsorb to allow for further tissue ingrowth and in yet another embodiment, such implantable devices can fully degrade or bioabsorb to allow for even further tissue ingrowth. Various biodegradable or absorbable porous polymeric materials are proposed for tissue augmentation and repair.

In one embodiment of the invention the at least partially degradable or fully resorbable matrix can be employed as a hybrid dressing scaffold material for the treatment of chronic ulcers that form in patients due to impaired peripheral vascular perfusion. These ulcers can be diabetic ulcers, decubitus ulcers, or arterial/venous insufficiency ulcers. Current treatments of these very difficult to heal wounds involves the application of vacuum (negative pressure wound therapy—NPWT) to the wound bed through a non-resorbable foam or gauze dressing. This method treatment presents two complications, i.e., significant pain during dressing changes since tissue grows into the pores/interstices of the currently used dressings in NPWT, and prolonged inflammation of the site as a result of the inadvertent damage during dressing change. A resorbable elastomeric matrix as proposed in the current invention address both these important clinical unmet needs by service as a "stay-in-place" dressing-scaffold that enables delivery of NPWT to the wound bed and at the same time serving as a scaffold to promote tissue ingrowth that is eventually resorbed at a controlled degradation rate.

In another embodiment of the invention, the at least partially degradable or fully resorbable elastomeric matrix can be used for applications as a three dimensional tissue filler to support tissue ingrowth at sites of excisional biopsies done for cancer diagnosis and therapy. This includes applications in breast cancer therapy such as lumpectomies and other procedures that involve removal of significant amounts of connective tissue. Other similar applications are in the field of plastic surgery wherein the elastomeric matrix can be used to fill tissue defects created at the donor site in tram flap procedures In another embodiment of the invention, the at least partially degradable or fully resorbable elastomeric matrix can be used for applications in general surgery involving the repair and reinforcement of soft tissue defects at sites that are highly prone to infection or require well-tolerated device with excellent tissue ingrowth and biointegration of the implant with no device-related adverse events that can cause post-surgery pain and discomfort. These include repair of complex incisional hernias, gastrointestinal fistulas, anal fistulas and enterocutaneuous fistulas. All these applications require a resorbable elastomeric matrix material that fills the 3-dimensional defect site, engenders tissue ingrowth, and degrades at a predetermined rate to allow the remodeling of the extracellular matrix that is laid down during the early phases of wound healing In another embodiment of the invention, the at least partially degradable or fully resorbable elastomeric matrix can be used for applications in repair of orthopedic soft tissues such as tendons, ligaments, meniscus, intervertebral disk, and articular cartilage. In each of these applications, the elastomeric matrix can also be implanted and deliver various bioactive and cellular components such as platelet rich plasma, platelet rich fibrin matrix, growth factors (PDGF, FGF) to improve the regeneration of tissue in avascular zones.

In another embodiment of the invention, the at least partially degradable or fully resorbable elastomeric matrix can be used for endovascular and cardiovascular/neurovascular applications such as aneurysm occlusion, closure of atrial and ventricular septal defects, closure of arteriotomy sites, vascular occlusion, etc.

In another embodiment of the invention, the at least partially degradable or fully resorbable elastomeric matrix can be used for delivery of adult cells, adult mesenchymal and hematopoetic stem cells, differentiated cells derived from induced Pluripotent Stem (iPS) cells as well as those derived from human embryonic stem cells (hESC) to target sites for therapeutic purposes. Applications include (but are not limited to) delivery of iPS derived pancreatic islet cells into liver parenchyma for curing Type 1 and Type 2 diabetes, delivery of cardiac myocytes into regions of cardiac muscle that have ischemic damage resulting from infarcts, delivery of stem cells for guided nerve generation in the peripheral nervous system, and spinal cord regeneration applications.

In another embodiment of the invention, the at least partially degradable or fully resorbable elastomeric matrix can be used as a carrier for various bioactive agents and proteins/peptides applied as coatings to the elastomeric matrix substrate or via immobilization/attachment of functionalized end groups. Applications envisioned include promotion of selective cellular membrane integrin receptor adhesion, improved biocompatibility for blood contacting applications, enhanced cellular activity and synthesis of extracellular matrix proteins, and leveraging these benefits to accelerate the repair process in tissues.

It would be desirable to form implantable devices suitable for use as tissue engineering scaffolds, or other comparable substrates, to support in vivo cell propagation applications, for example, in a large number of orthopedic applications especially in soft tissue attachment, regeneration, augmentation, support and ingrowth of a prosthetic organ. In another embodiment, it would also be desirable to form implantable devices suitable for use as tissue engineering to support in vivo cell or tissue propagation applications, for example in a large number of surgical or wound healing applications, such as healing of tissue where weakness exists in the cases of repair of soft tissue defects such as number of hernia applications, surgical meshes for augmentation Without being bound by any particular theory, having a high void content and a high degree of reticulation allowing unfettered access to the inter-connected and inter-communicating cells and pores that constitute the high void content is thought to allow the implantable device to become at least partially ingrown and/or proliferated, in some cases substantially ingrown and proliferated. Without being bound by any particular theory, the reticulated implantable devices having a high void content and a high degree of reticulation or inter-connectivity and inter-communication between cells and pores that constitute these voids that can be accessed by the in vivo cell or tissue propagation is thought to allow the implantable device to become at least partially ingrown and/or proliferated, in some cases substantially ingrown and proliferated, in other cases completely ingrown and proliferated, with cells including tissues such as fibroblasts, fibrous tissues, synovial cells, bone marrow stromal cells, stem cells and/or fibrocartilage cells. The ingrown and/or proliferated tissues thereby provide functionality over time, such as load bearing capability, for defect repair of the original tissue that is being repaired or replaced. Owing to the biointegrative three dimensional inter-connected and inter-communicating structure characteristics of the base reticulated implantable devices, embodiments of the invention have the advantage of potentially better and faster tissue in-growth, healing, and remodeling. The high degree of initial inter-connected and inter-communicated accessible void content can be enhanced by further at least partial degradation, at least partial absorption or complete degradation and absorption of the implantable device allowing for progressively larger parts of the defect to be replaced and regenerated with new tissue. In another embodiment, the high degree of initial inter-connected and inter-communicated accessible void content can be enhanced by combination of substantially partially degradation and absorption of the implantable device followed by or in conjunction with small remnants being biocompatibly bio-erodible again allowing for progressively larger parts of the defect to be replaced and regenerated with new tissue. This at least partial or full degradation or absorption ultimately leads to further enhancement of the already high void content of the reticulated matrix with its high degree of inter-connectivity leading to higher volume of tissue incorporation and less-hindered bio-integration. The tissue incorporation and less-hindered bio-integration is even further enhanced by progressive degradation and absorption that occurs in case of both partial or complete degradation and absorption.

In one aspect of this invention, the at least partially degradable reticulated elastomeric matrix which is designed to support tissue ingrowth may contain at least one functional element that is useful or necessary for the intended for repair of the targeted tissue defects. In one embodiment, the functional element is a reinforcing element that can be fiber or a mesh or a film designed to enhance the mechanical load bearing functions such as strength, stiffness, tear resistance, burst strength, suture pull out strength, etc. Such reinforcements may made from either be permanent or resorbable copolymers and homopolymers. In other embodiments, the functional element is a thin layer, coating or film of either a permanent polymer or biodegradable polymer or a bioactive polymer or a biopolymer or biologically derived collagen used to reduce the potential for adhesions, reduce the potential for biological adhesions and enhance tissue response. In yet another embodiment, the functional element is a polymeric and/or metallic structures used to impart shape, shape memory or structural support during delivery or placement of the device; and markers including dyes used to differentiate between two sides of a mesh which may have differing characteristics. In one embodiment, one or all or at least a selected number of the functional elements can be incorporated into the least partially degradable reticulated elastomeric matrix. Any of these preferred functional elements may be incorporated with the least partially degradable reticulated elastomeric matrix using various processing techniques known in the art including adhesive bonding, melt processing, compression molding, solution casting, thermal bonding, suturing, and other techniques.

In one embodiment, in some orthopedic applications such as rotator cuff repair or repair of soft tissue defects such as number of hernia applications where the implantable device serves in an augmentary role, precise fitting may not be required to match or fit the tissue that is being repaired or regenerated. The resilient nature of the matrix allows for the device or the material to follow the contour of the target site in the body and one embodiment, fills the target space at it can provide a fit and in another embodiment, the resilient nature of the matrix allows for recover from the first shape to the second shape. In another embodiment, an implantable device containing a reinforced reticulated elastomeric matrix is shaped prior to its use, such as in surgical repair of tendons and ligaments or in repair of soft tissue defects, specifically inguinal, femoral, ventral, incisional, umbilical, and epigastric hernias; meshes for tissue augmentation, support and repair. One exemplary method of shaping is trimming. When shaping is desired, the reinforced reticulated elastomeric matrix can be trimmed in its length and/or width direction along the lines or reinforcing fibers. In one embodiment, this trimming is accomplished so as to leave about 2 mm outside the reinforcement border, e.g., to facilitate suture attachment during surgery. In another embodiment, when shaping is desired, the reinforced reticulated elastomeric matrix can be trimmed along its length and/or width direction, along any other regular curved dimensions such as circle or ellipse or along any irregular shape.

Broadly stated, certain embodiments of the reticulated, at least partially degradable elastomeric products of the invention comprise or are largely if not entirely, constituted by a highly permeable, reticulated matrix formed of an at least partially degradable polymeric elastomer that is resiliently-compressible so as to regain its shape after delivery to a biological site. In another embodiment of the reticulated, completely degradable elastomeric products of the invention comprise or are largely if not entirely, constituted by a highly permeable, reticulated matrix formed of an at least partially degradable polymeric elastomer that is resiliently-compressible so as to regain its shape after delivery to a biological site. In one embodiment, the elastomeric matrix has good fatigue resistance associated with dynamic loading. In another embodiment, the elastomeric matrix is chemically well-characterized. In another embodiment, the elastomeric matrix is physically well-characterized. In another embodiment, the elastomeric matrix is chemically and physically well-characterized.

Certain embodiments of the invention can be used to support cell growth and permit cellular ingrowth and proliferation in vivo and can be useful as in vivo biological implantable devices, for example, for tissue engineering scaffolds that may be used in vitro or in vivo to provide a substrate for cellular propagation.

The implantable devices of the invention can be useful for many applications as long-term tissue engineering implants, especially where dynamic loadings and/or extensions are experienced, such as in soft tissue related orthopedic applications for repair and regeneration. In some embodiments, the reticulated elastomeric matrices of the present invention are as described in U.S. patent application Ser. No. 10/848,624, filed May 17, 2004 (published as U.S. Patent Application Publication No. U.S. 2005-0043816-A1 on Feb. 24, 2005 and now U.S. Pat. No. 7,803,395), and U.S. Patent Application Publication No. 2007/0190108 filed on Jan. 7, 2007, U.S. Patent Application Publication No. 2010/0318108 filed on Feb. 2, 2010, the disclosures of each of which are hereby incorporated herein by this reference in their entireties for all purposes.

In one embodiment, the at least partially degradable reticulated elastomeric matrix of the invention can be used to facilitate tissue ingrowth by providing a surface for cellular attachment, migration, proliferation and/or coating (e.g., collagen) deposition. In another embodiment, any type of tissue is allowed to grow into an implantable device comprising an at least partially degradable or fully degradable reticulated elastomeric matrix of the invention, including, by way of example, epithelial tissue (which includes, e.g., squamous, cuboidal and columnar epithelial tissue), connective tissue (which includes, e.g., areolar tissue, dense regular and irregular tissue, reticular tissue, adipose tissue, cartilage and bone), and muscle tissue (which includes, e.g., skeletal, smooth and cardiac muscle), or any combination thereof, e.g., fibrovascular tissue. In another embodiment of the invention, an implantable device comprising an at least partially degradable reticulated elastomeric matrix of the invention can be used to have tissue ingrowth substantially throughout the volume of its interconnected pores.

In one embodiment, the invention comprises an implantable device having sufficient resilient compressibility to be delivered by a "delivery-device", i.e., a device with a chamber for containing an elastomeric implantable device while it is delivered to the desired site then released at the site, e.g., using a catheter, endoscope, arthoscope, laproscope, cystoscope or syringe. In another embodiment, the thus-delivered elastomeric implantable device substantially regains its shape after delivery to a biological site and has adequate biodurability and biocompatibility characteristics to be suitable for long-term implantation.

In another embodiment, the thus-delivered elastomeric implantable device substantially regains its shape after delivery to a biological site and has adequate biocompatibility as it degrades or absorbs over time. In another embodiment, the thus-delivered elastomeric implantable device can span defects and serve to bridge a gap or a defect in the native tissue.

The structure, morphology and properties of the elastomeric matrices of this invention can be engineered or tailored over a wide range of performance by varying the starting materials and/or the processing conditions for different functional or therapeutic uses. The wide range of performance can include but not limited to loading, delivery and placement of the device as well as the biocompatible in vivo functionality ranging from cellular attachment, tissue ingrowth and proliferation to degree and time of degradation and absorption.

Without being bound by any particular theory, it is believed that an aim of the invention, i.e., to provide a light-weight structure, parts of which are durable and parts of which are partially or fully degradable over time or a combination of substantially partially degradable followed by or in conjunction with small remnants being biocompatibly erodible or bio-erodible and that can be used to fill a biological volume or cavity or defects and containing sufficient porosity distributed throughout the volume, can be fulfilled by permitting one or more of: occlusion, embolization, cellular ingrowth, cellular proliferation, tissue regeneration, cellular attachment, drug delivery, enzymatic action by immobilized enzymes, and other useful processes as described herein including, in particular, the applications to which priority is claimed. The available space for this light-weight structure for cellular ingrowth, cellular proliferation, tissue regeneration and cellular attachment increases over time progressively encompassing the biological volume or cavity or defects.

In one embodiment, elastomeric matrices of the invention have sufficient resilience to allow substantial recovery, e.g., to at least about 50% of the size of the relaxed configuration in at least one dimension, after being compressed for implantation in the human body, for example, a low compression set, e.g., at 25° C. or 37° C., and sufficient strength and flow-through for the matrix to be used for controlled release of pharmaceutically-active agents, such as a drug, and for other medical applications. In another embodiment, elastomeric matrices of the invention have sufficient resilience to allow recovery to at least about 25% of the size of the relaxed configuration in at least one dimension after being compressed for implantation in the human body. In another embodiment, elastomeric matrices of the invention have sufficient resilience to allow recovery to at least about 60% of the size of the relaxed configuration in at least one dimension after being compressed for implantation in the human body. In another embodiment, elastomeric matrices of the invention have sufficient resilience to allow recovery to at least about 90% of the size of the relaxed configuration in at least one dimension after being compressed for implantation in the human body. In yet another embodiment, elastomeric matrices of the invention have sufficient resilience to allow recovery to at least about 95% of the size of the relaxed configuration in at least one dimension after being compressed for implantation in the human body.

In the present application, the elastomeric matrix and other products are initially stable for extended periods of time in a biological environment but eventually will show partial degradation or complete degradation. Such products should not exhibit significant symptoms of breakdown or degradation, erosion or significant deterioration of mechanical properties relevant to their employment when exposed to biological environments for periods of time that may be weeks or months or even a few years. As the device or the product partially degrades or absorbs commensurate with the use of the implantable device, the non-degradable part or the remaining part of the device or products are stable and biocompatible for extended periods of time in a biological environment and do not exhibit significant symptoms of breakdown or degradation when exposed to biological environments for periods of time commensurate with the use of the implantable device. However, the non-degradable parts formed from the low solid content of the high void containing reticulated elastomeric matrix will exist in very small volume and will likely to bioerode or erode away from the implantation site or stay at the implantation site without any biocompatibility issues. In one embodiment, the non-degradable parts can be less than 3 cubic centimeter (cc) out of a total initial implantable matrix volume of 100 cc and in another embodiment, the non-degradable parts can be less than 2 cc out of a total initial implantable matrix volume of 100 cc. The degradable part of the device or the product absorbs in a biocompatible fashion over a period of time and in one embodiment over a long period of time exceeding at least 60 days or at least 181 days or at least one year or at least two years or at least three years. The period of implantation may be weeks or months or a few years; the lifetime of a host product in which the elastomeric products of the invention are incorporated, such as a graft or prosthetic; or the lifetime of a patient host to the elastomeric product. In one embodiment, the desired period of exposure is to be understood to be at least partially about 29 days. In another embodiment, the desired period of exposure is to be understood to be at least partially 29 days. In one embodiment, the implantable device is biodurable at least partially for at least 2 months. In another embodiment, the implantable device is biodurable at least partially for at least 6 months. In another embodiment, the implantable device is biodurable at least partially for at least 12 months. In another embodiment, the implantable device is biodurable at least partially for longer than 12 months. In another embodiment, the implantable device is biodurable for at least at least partially 24 months. In another embodiment, the parts of the implantable device are biodurable at least partially for at least 5 years. In another embodiment, the parts of the implantable device are biodurable at least partially for longer than 5 years. In another embodiment, the entire implantable device degrades or bioabsorbs completely over time in a biocompatible fashion. Unlike the well known degradable aliphatic polyesters and degradable thermoplastic polyurethane containing aliphatic polyesters whose hydrolytic degradation rates are controlled by forming copolymers or blends using various combination of degradable aliphatic polyester homopolymers with different degradation rates, the degradation rates of the segmented polyurethane elastomeric matrix of this invention are further controlled by nature and degree of cross-linking, level of chain extension of the hard segment and the ratio of urethane to urea content.

In one embodiment, the products of the invention are also biocompatible. In the present application, the term "biocompatible" means that the product induces few, if any, adverse biological reactions when implanted in a host patient. Employment of an implant that can support invasion of fibroblasts and other cells enables the implant to eventually become a biointegrated part of the healed aneurysm. The implant can be biocompatible and elicit no adverse biological response on delivery or after occlusion and the healing of the aneurysm.

In one embodiment, biodurable part of the partially degradable reticulated elastomeric matrix of this invention is also biocompatible. In another embodiment, the non-degradable or the no-resorbable or the biostable part of the partially degradable reticulated elastomeric matrix of this invention is also biocompatible. In another embodiment, the non-degradable or the no-resorbable or the biostable part of the partially degradable reticulated elastomeric matrix of this will likely to bioerode or erode away from the implantation site or stay at the implantation site without any biocompatibility issues. In the present application, the term "biocompatible" means that the product induces few, if any, adverse biological reactions when implanted in a host patient. Similar considerations applicable to "biodurable" also apply to the property of "biocompatibility". The non-degradable or the no-resorbable or the biostable part comprises the hard segment of the partially degradable reticulated elastomeric matrix. The hard segment comprises non-degradable isocyanate-derived hard segment.

The biodegradable components of the at least partially degradable elastomeric matrix can degrade by hydrolysis or by enzymatic activity. In one embodiment, the biodegradable components of the at least partially degradable elastomeric matrix can bio-degrade or may be broken down into innocuous, nontoxic or biocompatible products. The degradation product is not allowed to evoke unusual inflammatory response/toxic response and is metabolized by the body in a biocompatible fashion and is characterized by the absence of or extremely low: cytotoxicity, hemotoxicity, carcinogenicity, mutagenicity, or teratogenicity.

An intended biological environment can be understood to be in vivo, e.g., that of a patient host into which the product is implanted or to which the product is topically applied, for example, a mammalian host such as a human being or other primate, a pet or sports animal, a livestock or food animal, or a laboratory animal. All such uses are contemplated as being within the scope of the invention. As used herein, a "patient" is an animal. In one embodiment, the animal is a bird, including but not limited to a chicken, turkey, duck, goose or quail, or a mammal. In another embodiment, the animal is a mammal, including but not limited to a cow, horse, sheep, goat, pig, cat, dog, mouse, rat, hamster, rabbit, guinea pig, monkey and a human.

In another embodiment, the animal is a primate or a human. In another embodiment, the animal is a human.

In one embodiment, structural materials for the inventive reticulated elastomers are synthetic polymers, especially but not exclusively, elastomeric polymers that are partially susceptible to biological degradation, for example, in one embodiment, polycaprolactone-polyethylene glycol polyurethanes, polycaprolactone-polyethylene glycol urea-urethane, polycaprolactone polyurethanes, polycaprolactone urea-urethanes, polycaprolactone-polylactide polyurethanes, polycaprolactone-polylactide urea-urethanes, polycaprolactone-polyglycolide polyurethanes, polycaprolactone-polyglycolide urea-urethanes, polycaprolactone-d/l lactide polyurethanes, polycaprolactone-d/l lactide urea-urethanes, polycaprolactone-polyparadioxanone polyurethanes, polycaprolactone-polyparadioxanone urea-urethane or copolymers or mixtures thereofs. Some illustrative copolymers include but not limited to polycaprolactone-co-glycolide-co-lactide polyurethanes, polycaprolactone-co-glycolide-co-lactide urea-urethanes, polycaprolactone-co-glycolide-co-d/l lactide polyurethanes, polycaprolactone-co-glycolide-co-d/l lactide urea-urethanes, polycaprolactone-co-lactide-co-d/l lactide polyurethanes, polycaprolactone-co-lactide-co-d/l lactide urea-urethanes. Such elastomers are generally hydrophobic but, pursuant to the invention, may be treated to have surfaces that are less hydrophobic or somewhat hydrophilic. In another embodiment, such elastomers may be produced with surfaces that are significantly or largely hydrophobic The reticulated at least partially degradable elastomeric products of the invention can be described as having a "macrostructure" and a "microstructure", which terms are used herein in the general senses described in the following paragraphs.

The "macrostructure" refers to the overall physical characteristics of an article or object formed of the at least partially degradable elastomeric product of the invention, such as: the outer periphery as described by the geometric limits of the article or object, ignoring the pores or voids; the "macrostructural surface area" which references the outermost surface areas as though any pores thereon were filled, ignoring the surface areas within the pores; the "macrostructural volume", or simply the "volume" occupied by the article or object which is the volume bounded by the macrostructural, or simply "macro", surface area; and the "bulk density" which is the weight per unit volume of the article or object itself as distinct from the density of the structural material.

The "microstructure" refers to the features of the interior structure of the at least partially degradable elastomeric material from which the inventive products are constituted such as pore dimensions; pore surface area, being the total area of the material surfaces in the pores; and the configuration of the struts and intersections that constitute the solid structure of certain embodiments of the inventive elastomeric product.

Referring to FIG. 1, what is shown for convenience is a schematic depiction of the particular morphology of a reticulated matrix. FIG. 1 is a convenient way of illustrating some of the features and principles of the microstructure of embodiments of the invention. FIG. 1 is not intended to be an idealized depiction of an embodiment of, nor is it a detailed rendering of a particular embodiment of the elastomeric products of the invention. Other features and principles of the microstructure will be apparent from the present specification, or will be apparent from one or more of the inventive processes for manufacturing porous elastomeric products that are described herein.

Morphology

Described generally, the microstructure of the illustrated porous at least partially degradable elastomeric matrix 10, which may, inter alia, be an individual element having a distinct shape or an extended, continuous or amorphous entity, comprises a reticulated solid phase 12 formed of a suitable at least partially degradable elastomeric material and interspersed therewithin, or defined thereby, a continuous interconnected void phase 14, the latter being a principle feature of a reticulated structure. In one embodiment, the reticulated structure comprises a continuous, interconnected and intercommunicating networks of cells, pores, and voids to permit ingrowth and proliferation of tissue into the matrix interiors. In another embodiment, the void space of the reticulated structure comprises a plurality of interconnected pores forming a continuous network of intercommunicating passageways extending from an interior portion to an exterior surface of said matrix.

In one embodiment, the elastomeric material of which elastomeric matrix 10 is constituted may be a mixture or blend of multiple materials. In another embodiment, the elastomeric material is a single synthetic polymeric elastomer such as will be described in more detail below. In other embodiments, although elastomeric matrix 10 is subjected to post-reticulation processing, such as annealing, compressive molding and/or reinforcement, it is to be understood that the elastomeric matrix 10 retains its defining characteristics, that is, it remains at least partially degradable, reticulated and elastomeric.

Void phase 14 will usually be air- or gas-filled prior to use. During use, void phase 14 can in many but not all cases become filled with liquid, for example, with biological fluids or body fluids.

Solid phase 12 of elastomeric matrix 10, as shown in FIG. 1, has an organic structure and comprises a multiplicity of relatively thin struts 16 that extend between and interconnect a number of intersections 18. The intersections 18 are substantial structural locations where three or more struts 16 meet one another. Four or five or more struts 16 may be seen to meet at an intersection 18 or at a location where two intersections 18 can be seen to merge into one another. In one embodiment, struts 16 extend in a three-dimensional manner between intersections 18 above and below the plane of the paper, favoring no particular plane. Thus, any given strut 16 may extend from an intersection 18 in any direction relative to other struts 16 that join at that intersection 18. Struts 16 and intersections 18 may have generally curved shapes and define between them a multitude of pores 20 or interstitial spaces in solid phase 12. Struts 16 and intersections 18 form an interconnected, continuous solid phase.

As illustrated in FIG. 1, the structural components of the solid phase 12 of elastomeric matrix 10, namely struts 16 and intersections 18, may appear to have a somewhat laminar configuration as though some were cut from a single sheet, it will be understood that this appearance may in part be attributed to the difficulties of representing complex three-dimensional structures in a two dimensional figure. Struts 16 and intersections 18 may have, and in many cases will have, non-laminar shapes including circular, elliptical and non-circular cross-sectional shapes and cross sections that may vary in area along the particular structure, for example, they may taper to smaller and/or larger cross sections while traversing along their longest dimension.

The cells of elastomeric matrix 10 are formed from clusters or groups of pores 20, which would form the walls of a cell except that the cell walls 22 of most of the pores 20 are absent or substantially absent owing to reticulation. In particular, a small number of pores 20 may have a cell wall of structural material also called a "window" or "window pane" such as cell wall 22. Such cell walls are undesirable to the extent that they obstruct the passage of fluid and/or propagation and proliferation of tissues through pores 20. Cell walls 22 may, in one embodiment, be removed in a suitable process step, such as reticulation as discussed below.

The individual cells forming the reticulated elastomeric matrix are characterized by their average cell diameter or, for nonspherical cells, by their largest transverse dimension. The reticulated elastomeric matrix comprises a network of cells that form a three-dimensional spatial structure or void phase 14 which is interconnected via the open pores 20 therein. In one embodiment, the cells form a 3-dimensional superstructure. The boundaries of individual cells can be visualized from the sectioned struts 16 and/or intersections 18. The pores 20 are generally two- or three-dimensional structures. The pores provide connectivity between the individual cells, or between clusters or groups of pores which form a cell.

Except for boundary terminations at the macrostructural surface, in the embodiment shown in FIG. 1 solid phase 12 of elastomeric matrix 10 comprises few, if any, free-ended, dead-ended or projecting "strut-like" structures extending from struts 16 or intersections 18 but not connected to another strut or intersection.

However, in an alternative embodiment, solid phase 12 can be provided with a plurality of such fibrils (not shown), e.g., from about 1 to about 5 fibrils per strut 16 or intersection 18. In some applications, such fibrils may be useful, for example, for the additional surface area they provide.

Struts 16 and intersections 18 can be considered to define the shape and configuration of the pores 20 that make up void phase 14 (or vice versa). Many of pores 20, in so far as they may be discretely identified, open into and communicate, by the at least partial absence of cell walls 22, with at least two other pores 20. At intersections 18, three or more pores 20 may be considered to meet and intercommunicate. In certain embodiments, void phase 14 is continuous or substantially continuous throughout elastomeric matrix 10, meaning that there are few if any closed cell pores. Such closed cell pores, the interior volume of each of which has no communication with any other cell, e.g., is isolated from an adjacent cells by cell walls 22, represent loss of useful volume and may obstruct access of useful fluids to interior strut and intersection structures 16 and 18 of elastomeric matrix 10.

In one embodiment, closed cell pores, if present, comprise less than about 60% of the volume of elastomeric matrix 10. In another embodiment, closed cell pores, if present, comprise less than about 50% of the volume of elastomeric matrix 10. In another embodiment, closed cell pores, if present, comprise less than about 40% of the volume of elastomeric matrix 10. In another embodiment, closed cell pores, if present, comprise less than about 50% of the volume of elastomeric matrix 10. In another embodiment, closed cell pores, if present, comprise less than about 30% of the volume of elastomeric matrix 10. In another embodiment, closed cell pores, if present, comprise less than about 25% of the volume of elastomeric matrix 10. In another embodiment, closed cell pores, if present, comprise less than about 20% of the volume of elastomeric matrix 10. In another embodiment, closed cell pores, if present, comprise less than about 15% of the volume of elastomeric matrix 10. In another embodiment, closed cell pores, if present, comprise less than about 10% of the volume of elastomeric matrix 10. In another embodiment, closed cell pores, if present, comprise less than about 5% of the volume of elastomeric matrix 10. In another embodiment, closed cell pores, if present, comprise less than about 2% of the volume of elastomeric matrix 10. The presence of closed cell pores can be noted by their influence in reducing the volumetric flow rate of a fluid through elastomeric matrix 10 and/or as a reduction in cellular ingrowth and proliferation into elastomeric matrix 10.

In another embodiment, elastomeric matrix 10 is reticulated. In another embodiment, elastomeric matrix 10 is partially reticulated. In another embodiment, elastomeric matrix 10 is substantially reticulated. In another embodiment, elastomeric matrix 10 is fully reticulated. In another embodiment, elastomeric matrix 10 has many cell walls 22 removed. In another embodiment, elastomeric matrix 10 has most cell walls 22 removed. In another embodiment, elastomeric matrix 10 has substantially all cell walls 22 removed. In another embodiment, elastomeric matrix 10 has all cell walls 22 removed In another embodiment, solid phase 12, which may be described as reticulated, comprises a continuous network of solid structures, such as struts 16 and intersections 18, without any significant terminations, isolated zones or discontinuities, other than at the boundaries of the elastomeric matrix, in which network a hypothetical line may be traced entirely through the material of solid phase 12 from one point in the network to any other point in the network. The inventive implantable device, is reticulated, i.e., comprises an interconnected network of cells and pores and channels and voids that provides fluid permeability throughout the implantable device and permits cellular and tissue ingrowth and proliferation into the interior of the implantable device. In one embodiment, the inventive implantable device, preferably the outer surface, is reticulated. The biodurable elastomeric matrix or material is considered to be reticulated because its microstructure or the interior structure comprises inter-connected and inter-communicating pores and/or voids bounded by configuration of the struts and intersections that constitute the solid structure. The continuous interconnected void phase is the principle feature of a reticulated structure.

In another embodiment, void phase 14 is also a continuous network of interstitial spaces, or intercommunicating fluid passageways for gases or liquids, which fluid passageways extend throughout and are defined by (or define) the structure of solid phase 12 of elastomeric matrix 10 and open into all its exterior surfaces. In another embodiment, void phase 14 of elastomeric matrix 10 is continuous and fully accessible by proliferating tissues and cells or by fluids and interconnected and inter-communicating. In another embodiment, void phase 14 of elastomeric matrix 10 is a continuous interconnected and inter-communicating network of voids, cells and pores and this continuous void phase is the principle characteristic of the reticulated matrix. In other embodiments, as described above, there are only a few, substantially no, or no occlusions or closed cell pores that do not communicate with at least one other pore 20 in the void network. Also in this void phase network, a hypothetical line may be traced entirely through void phase 14 from one point in the network to any other point in the network.

In concert with the objectives of the invention, in one embodiment the microstructure of elastomeric matrix 10 can constructed to permit or encourage cellular adhesion to the surfaces of solid phase 12, neointima formation thereon and cellular and tissue ingrowth and proliferation into pores 20 of void phase 14, when elastomeric matrix 10 resides in suitable in vivo locations for a period of time. Owing to its partially degradable nature of elastomeric matrix 10, the cellular and tissue ingrowth and proliferation into pores of the void phase is allowed to progressively increased over time. In another embodiment, owing to its partially degradable nature of elastomeric matrix 10, the amount of cellular and tissue ingrowth and proliferation into pores of the void phase progressively can increase over time as more void space is created by the absorption of the partially degrading matrix.

In another embodiment, the reticulated structure allows for ingrowth for such tissues as fibrovascular tissues, fibroblasts, fibrocartilage cells, endothelial tissues, etc. In another embodiment, the tissue ingrowth and proliferation into the interior of the implantable device can allow for bio-integration of the device to the site where the device is placed. In yet another embodiment, the tissue ingrowth and proliferation into the interior of the implantable device prevents migration and recanalization.

Preferred scaffold materials for the implants have a reticulated structure with sufficient and required liquid permeability and thus selected to permit blood, or other appropriate bodily fluid, and cells and tissues to access interior surfaces of the implants. This can happen due to the presence of inter-connected and inter-communicating, reticulated open pores and/or voids and/or channels and/or concavities that form fluid passageways or fluid permeability providing fluid access all through. These inter-connected and inter-communicating, reticulated open pores and/or cells and/or voids and/or channels and/or concavities are accessible for fluid passageways or fluid permeability providing fluid access all through. The accessible and inter-connected and inter-communicating nature of the reticulated matrix distinguishes it from porous materials and in porous materials although there are voids, not all of them are accessible as they are not all inter-communicating and inter-connected as is the case with reticulated matrix. Over time, the tissue ingrowth and proliferation into the interior of the implantable device placed at the defect site can lead to bio-integration of the device to the site where the device is placed. Without being bound by any particular theory, it is believed that the high void content and degree of reticulation of the reticulated elastomeric matrix not only allows for tissue ingrowth and proliferation of cells within the matrix but also allows for orientation and remodeling of the healed tissue after the initial tissues have grown into the implantable device. The biodurable reticulated elastomeric material that comprises the implant device can allow for tissue ingrowth and proliferation and bio-integrate the implant device to the aneurysm site. The biodurable reticulated elastomeric material that comprises the implant device can allow for tissue ingrowth and will seal the aneurysm and in one embodiment can provide a permanent sealing of the defect. The reticulated elastomeric matrix and/or the implantable device, over time, provides functionality or substantial functionality such as load bearing capability or re-modeling of the initial cell and tissue infiltration to the morphology and structure similar to the original tissue that is being repaired or replaced. Without being bound by any particular theory, it is believed that owing to the high void content of the reticulated elastomeric matrix or implantable device comprising it, once the tissue is healed and bio-integration takes place, most of the regenerated or repaired site consists of new tissue and a small volume fraction of the reticulated elastomeric matrix, or the implantable device formed from it.

In another embodiment, such cellular or tissue ingrowth and proliferation, which may for some purposes include fibrosis and eventual tissue regeneration and re-modeling, can occur or be encouraged not just into exterior layers of pores 20, but into the deepest interior of and throughout elastomeric matrix 10. This is possible owing to the presence of interconnected and inter-communicating cells and pores and voids, all of which are accessible for cellular or tissue ingrowth and proliferation. Thus, in this embodiment, the space occupied by elastomeric matrix 10 can become entirely filled by the cellular and tissue ingrowth and proliferation in the form of fibrotic, scar or other tissue except for the space occupied by the elastomeric solid phase 12. Over time as more void space is created by the absorption of the partially degrading elastomeric solid phase, the additional void phase is also filled by the cellular and tissue ingrowth and proliferation in the form of fibrotic, scar or other tissue. In another embodiment, the inventive implantable device can function so that ingrown tissue is kept vital, for example, by the prolonged presence of a supportive microvasculature that is at least partially non-degradable.

To this end, particularly with regard to the morphology of void phase 14, in one embodiment elastomeric matrix 10 is reticulated with open interconnected and inter-communicating pores and these interconnected and inter-communicating pores and voids are also accessible for cellular and tissue ingrowth and proliferation. Without being bound by any particular theory, this is thought to permit natural irrigation of the interior of elastomeric matrix 10 with bodily fluids, e.g., blood, even after a cellular population has become resident in the interior of elastomeric matrix 10 so as to sustain that population by supplying nutrients thereto and removing waste products and degradation products therefrom. In another embodiment, elastomeric matrix 10 is reticulated with open interconnected and inter-communicating pores pores of a particular size range. In another embodiment, the interconnected and inter-communicating pores and voids facilitate and/or allow for the removal of the degradation products as the implantable device or the reticulated matrix degrades, bio-degrades or bioabsorbs and in another embodiment, this removal happens during or in concert with the natural irrigation by bodily fluids to and fro the interiors of elastomeric matrix 10, In another embodiment, elastomeric matrix 10 is reticulated with open interconnected pores with a distribution of size ranges. In another embodiment, elastomeric matrix 10 is reticulated with interconnected and inter-communicating cell and pores and voids, all of which are accessible by bodily fluids and cells and tissues.

It is intended that the various physical and chemical parameters of elastomeric matrix 10 including in particular the parameters to be described below, be selected to encourage cellular ingrowth and proliferation and also tissue ingrowth and proliferation according to the particular application for which an elastomeric matrix 10 is intended.

It will be understood that such constructions of elastomeric matrix 10 that provide interior cellular irrigation will be fluid permeable and may also provide fluid access through and to the interior of the matrix for purposes other than cellular irrigation, for example, for elution of pharmaceutically-active agents, e.g., a drug such as nitric oxide releasing polymer, anti-microbial agent platelet rich plasma or other biologically useful materials. Such materials may optionally be secured to the interior surfaces of elastomeric matrix 10 by application of suitable coatings that are preferably degradable and more preferably made from degradable polymers.

In another embodiment of the invention, gaseous phase 12 can be filled or contacted with a deliverable treatment gas, for example, a sterilant such as ozone or a wound healant such as nitric oxide, provided that the macrostructural surfaces are sealed, for example by a bioabsorbable membrane to contain the gas within the implanted product until the membrane erodes releasing the gas to provide a local therapeutic or other effect.

The matrix after its manufacture, which consists primarily of foaming, reticulation or machining to the desired size and shape of the implantable device, is washed in organic solvent such as isopropyl alcohol (IPA) and this removes any un-reacted ingredients and bringing down the residual level of extractable of volatile and semi-volatile organic compounds. The IPA wash is carried out by sonication in IPA for less than 30 minutes preferably less than 15 minutes and washing or cleaning by tumbling for times in excess of 2 hours or in excess of 4 hours or in excess of 6 hours before removing the IPA by vacuum dying. The reticulated structure facilitates easier removal of residual unused processing aids and/or unreacted starting ingredients during subsequent wash cycles, due to the presence of accessible open passages offered by interconnected and intercommunicating network of cells and pores. The washed reticulated matrix is thus rendered more biocompatible with extractable levels below 50 ppm or in one embodiment, below 300 ppm or in another embodiment below 1000 ppm.

Useful embodiments of the invention include structures that are somewhat randomized, as shown in FIG. 1 where the shapes and sizes of struts 16, intersections 18 and pores 20 vary substantially, and more ordered structures which also exhibit the described features of three-dimensional interpenetration of solid and void phases, structural complexity and high fluid permeability. The shapes and sizes of struts 16, intersections 18 and pores 20 will eventually undergo more changes as the degradable part of the device or the product absorbs in a biocompatible fashion over a period of time. Such more ordered structures can be produced by the processes of the invention as will be further described below.

Porosity

Post-reticulation, void phase 14 may comprise as little as 10% by volume of elastomeric matrix 10, referring to the volume provided by the interstitial spaces of elastomeric matrix 10 before any optional interior pore surface coating or layering is applied, such as for a reticulated elastomeric matrix that, after reticulation, has been compressively molded and/or reinforced as described in detail herein. In another embodiment, void phase 14 may comprise as little as 40% by volume of elastomeric matrix 10. In another embodiment, void phase 14 may comprise as little as 50% by volume of elastomeric matrix 10. In another embodiment, void phase 14 may comprise as least 70% by volume of elastomeric matrix 10. In another embodiment, void phase 14 may comprise at least 95% by volume of elastomeric matrix 10. In one embodiment, the volume of void phase 14, as just defined, is from about 10% to about 99% of the volume of elastomeric matrix 10. In another embodiment, the volume of void phase 14, as just defined, is from about 40% to about 99% of the volume of elastomeric matrix 10. In another embodiment, the volume of void phase 14, as just defined, is from about 30% to about 98% of the volume of elastomeric matrix 10. In another embodiment, the volume of void phase 14, as just defined, is from about 50% to about 99% of the volume of elastomeric matrix 10. In another embodiment, the volume of void phase 14, as just defined, is from about 70% to about 99% of the volume of elastomeric matrix 10. In another embodiment, the volume of void phase 14 is from about 80% to about 98% of the volume of elastomeric matrix 10. In another embodiment, the volume of void phase 14 is from about 90% to about 98% of the volume of elastomeric matrix 10.

One implanted in humans or animals or in in vivo situation, the void phase or the accessible space for tissue and cell ingrowth and proliferation in the reticulated matrix progressively increases over time owing to the partial or fully degradable nature of elastomeric matrix 10 that absorbs in a biocompatible fashion over a period of time. However in the case of least partially degradable reticulated matrix the presence of the stable non-degradable part of the elastomeric matrix or device or products, does not allow for increase in void phase beyond a certain limit. The increase in void phase as elastomeric matrix 10 that at least partially absorbs in a biocompatible fashion over a period of time can be between 40% to 90%. In another embodiment, the increase in void phase as elastomeric matrix 10 that at least partially absorbs in a biocompatible fashion over a period of time can be between 50% and 80 In yet another embodiment, the increase in void phase as elastomeric matrix 10 that at least partially absorbs in a biocompatible fashion over a period of time can be between 62% and 80%. In another embodiment, the increase in void phase as elastomeric matrix 10 that at least partially absorbs in a biocompatible fashion over a period of time can be greater than 95%. %. In another embodiment, the increase in void phase as elastomeric matrix 10 that at least partially absorbs in a biocompatible fashion over a period of time can be between 10% and 50% and in another embodiment can be between 15% and 40%. In another embodiment, the presence of a fully degradable elastomeric matrix or device or products, will allow for the void phase to increase with time until the elastomeric matrix is completely absorbed or degrades and the repaired, healed and re-modeled in-grown tissue will completely or substantially completely fill the target site or the space occupied by the implant after delivery and placement.

As used herein, when a pore is spherical or substantially spherical, its largest transverse dimension is equivalent to the diameter of the pore. When a pore is non-spherical, for example, ellipsoidal or tetrahedral, its largest transverse dimension is equivalent to the greatest distance within the pore from one pore surface to another, e.g., the major axis length for an ellipsoidal pore or the length of the longest side for a tetrahedral pore. As used herein, the "average diameter or other largest transverse dimension" refers to the number average diameter, for spherical or substantially spherical pores, or to the number average largest transverse dimension, for non-spherical pores.

In one embodiment to encourage cellular ingrowth and proliferation and to provide adequate fluid permeability, the average diameter or other largest transverse dimension of pores 20 is at least about 10 µm. In another embodiment, the average diameter or other largest transverse dimension of pores 20 is at least about 20 μm. In another embodiment, the average diameter or other largest transverse dimension of pores 20 is at least about 50 μm. In another embodiment, the average diameter or other largest transverse dimension of pores 20 is at least about 100 μm. In another embodiment, the average diameter or other largest transverse dimension of pores 20 is at least about 150 μm. In another embodiment, the average diameter or other largest transverse dimension of pores 20 is at least about 250 μm. In another embodiment, the average diameter or other largest transverse dimension of pores 20 is greater than about 250 μm. In another embodiment, the average diameter or other largest transverse dimension of pores 20 is greater than 250 μm. In another embodiment, the average diameter or other largest transverse dimension of pores 20 is at least about 450 μm. In another embodiment, the average diameter or other largest transverse dimension of pores 20 is greater than about 450 μm. In another embodiment, the average diameter or other largest transverse dimension of pores 20 is greater than 450 μm. In another embodiment, the average diameter or other largest transverse dimension of pores 20 is at least about 500 μm.

In another embodiment the average diameter or other largest transverse dimension of pores 20 is not greater than about 1000 μm. In another embodiment the average diameter or other largest transverse dimension of pores 20 is not greater than about 800 μm. In another embodiment the average diameter or other largest transverse dimension of pores 20 is not greater than about 600 μm. In another embodiment, the average diameter or other largest transverse dimension of pores 20 is not greater than about 500 μm. In another embodiment, the average diameter or other largest transverse dimension of pores 20 is not greater than about 450 μm. In another embodiment, the average diameter or other largest transverse dimension of pores 20 is not greater than about 350 μm. In another embodiment, the average diameter or other largest transverse dimension of pores 20 is not greater than about 250 μm. In another embodiment, the average diameter or other largest transverse dimension of pores 20 is not greater than about 150 μm. In another embodiment, the average diameter or other largest transverse dimension of pores 20 is not greater than about 20 μm.

In another embodiment, the average diameter or other largest transverse dimension of pores 20 is from about 10 μm to about 50 μm. In another embodiment, the average diameter or other largest transverse dimension of pores 20 is from about 20 μm to about 150 μm. In another embodiment, the average diameter or other largest transverse dimension of pores 20 is from about 150 μm to about 250 μm. In another embodiment, the average diameter or other largest transverse dimension of pores 20 is from about 250 μm to about 500 μm. In another embodiment, the average diameter or other largest transverse dimension of pores 20 is from about 450 μm to about 600 μm. In another embodiment, the average diameter or other largest transverse dimension of pores 20 is from about 10 μm to about 500 μm. In another embodiment, the average diameter or other largest transverse dimension of pores 20 is from about 20 μm to about 600 μm. In another embodiment, the average diameter or other largest transverse dimension of pores 20 is from about 50 μm to about 600 μm. In another embodiment, the average diameter or other largest transverse dimension of pores 20 is from about 100 μm to about 500 μm. In another embodiment, the average diameter or other largest transverse dimension of pores 20 is from about 50 μm to about 800 μm. In another embodiment, the average diameter or other largest transverse dimension of pores 20 is from about 50 μm to about 1000 μm. In another embodiment, the average diameter or other largest transverse dimension of pores 20 is from about 150 μm to about 350 μm.

In one embodiment to encourage cellular ingrowth and proliferation and to provide adequate fluid permeability, the average diameter or other largest transverse dimension of the cells of elastomeric matrix 10 is at least about 100 μm. In another embodiment, the average diameter or other largest transverse dimension of it cells is at least about 150 μm. In another embodiment, the average diameter or other largest transverse dimension of it cells is at least about 200 μm. In another embodiment, the average diameter or other largest transverse dimension of it cells is at least about 250 μm.

In another embodiment, the average diameter or other largest transverse dimension of the cells of elastomeric matrix 10 is not greater than about 1500 μm. In another embodiment, the average diameter or other largest transverse dimension of the cells of elastomeric matrix 10 is not greater than about 1200 μm. In another embodiment, the average diameter or other largest transverse dimension of the cells of elastomeric matrix 10 is not greater than about 1000 μm. In another embodiment, the average diameter or other largest transverse dimension of its cells is not greater than about 850 μm. In another embodiment, the average diameter or other largest transverse dimension of its cells is not greater than about 450 μm. In another embodiment, the average diameter or other largest transverse dimension of its cells is not greater than about 700 μm. In another embodiment, the average diameter or other largest transverse dimension of its cells is not greater than about 650 μm.

In another embodiment, the average diameter or other largest transverse dimension of the cells of elastomeric matrix 10 is from about 100 μm to about 1000 μm. In another embodiment, the average diameter or other largest transverse dimension of its cells is from about 150 μm to about 850 μm. In another embodiment, the average diameter or other largest transverse dimension of its cells is from about 200 μm to about 700 μm. In another embodiment, the average diameter or other largest transverse dimension of its cells is from about 250 μm to about 650 μm.

In another embodiment, an implantable device made from elastomeric matrix 10 may comprise pore sizes that vary from small, e.g., 20 μm, to large, e.g., 500 μm, in a single device. In another embodiment, an implantable device made from elastomeric matrix 10 may comprise cell sizes that vary from small, e.g., 100 μm, to large, e.g., 1000 μm, in a single device. In another embodiment, such a variation may occur across the cross-section of the entire material or across any sub-section of a cross-section. In another embodiment, such a variation occurs in a systematic gradual transition. In another embodiment, such a variation occurs in a stepwise manner. For example, the pore size distribution can be from about 20 μm to about 70 μm on one end of an implantable device and be from about 300 μm to about 500 μm on another end of the device. This change in pore size distribution can take place in one or more continuous transitions or in one or more discrete steps. Such variations in pore size distribution result in continuous transition zones or in discrete steps, i.e., the transition from one pore size distribution to another may be more gradual in the case of a continuous transition or transitions but more distinct in the case of a discrete step or steps. With regard to pore orientation, similar transitions may occur in the orientation of the pores, with more oriented pores transitioning into less oriented pores or even into pores substantially devoid of orientation across the cross-section or across a sub-section of the cross-section. The difference in the pore size distribution and/or orientation of the pores across a cross-section of implantable devices made from elastomeric matrix 10 may allow the device to be engineered for preferential behavior in terms of cell type, cell attachment, cell ingrowth and/or cell proliferation. Alternatively, different pore size distribution and/or orientation of the pores across the cross-section of implantable devices made from elastomeric matrix 10 may allow the device to be engineered for preferential behavior in terms of tissue type, tissue attachment, tissue ingrowth and/or tissue proliferation.

The partially degradable reticulated or the fully degradable matrix initially functions as a long term implantable pseudo-extracellular matrix supporting the continuum of biological events through the healing and remodeling cascade. This biocompatible degradable reticulated or the fully degradable matrix induces eventual bio-integration by being i) receptive of cell membrane adhesion, ii) providing platelet adhesion, activation, aggregation, iii) allowing for angiogenesis (formation of new blood vessel) and granulation, iv) allowing for cell migration and proliferation and finally v) for the formation of the extra cellular matrix synthesis (protein synthesis and assembly) and re-modeling of the synthesized extra cellular matrix.

Cells are allowed to adhere, proliferate and differentiate along and through the contours of the structure formed by the pore size distribution. The cell orientation and cell morphology can be used to result in engineered or newly-formed tissue that may further re-model to substantially replicate or mimic the anatomical features of real tissues, e.g., of the tissues being replaced. This preferential cell morphology and orientation ascribed to the continuous or step-wise pore size distribution variations, with or without pore orientation, can occur when the implantable device is placed, without prior cell seeding, into the tissue repair and regeneration site. This preferential cell morphology and orientation ascribed to the continuous or step-wise pore size distribution can also occur when the implantable device is placed into a patient, e.g., human or animal, tissue repair and regeneration site after being subjected to in vitro cell culturing. These continuous or step-wise pore size distribution variations, with or without pore orientation, can be important characteristics for TE scaffolds in a number of orthopedic applications, especially in soft tissue attachment, repair, regeneration, augmentation and/or support encompassing the spine, shoulder, knee, hand or joints, and in the growth of a prosthetic organ and orthopedic applications especially in hard tissue or bone repair and regeneration, In another embodiment, these continuous or step-wise pore size distribution variations, with or without pore orientation, can be important characteristics for TE scaffolds in a number of other surgical applications such as wound healing and defect filling, healing of tissue where weakness exists such as for repair of soft tissue defects, specifically inguinal, femoral, ventral, incisional, umbilical, and epigastric hernias; surgical meshes for tissue augmentation, support and repair; for therapeutic purposes. In another embodiment, these continuous or step-wise pore size distribution variations, with or without pore orientation, can be important characteristics for TE scaffolds in a number of applications healing of vascular and neuro-vascular defects including arteriovenous malformations (AVMs), aneurysms, anomalies of feeding and draining veins, arteriovenous fistulas, e.g., anomalies of large arteriovenous connections, and abdominal aortic aneurysm endograft endoleaks (e.g., inferior mesenteric arteries and lumbar arteries associated with the development of Type II endoleaks in endograft patients). In another embodiment, these continuous or step-wise pore size distribution variations, with or without pore orientation, can be important characteristics for TE scaffolds in a number of applications for cosmetic, reconstructive, urologic or gastroesophageal, gynecological, pelvic prolapse repair purposes. In another embodiment, these continuous or step-wise pore size distribution variations, with or without pore orientation, can be important characteristics for TE scaffolds in a number of applications for in wound healing, chronic wound healing, pressure and diabetic sores and other dermal tissue regeneration.

The morphology or structure of interconnected and inter-communicating network of accessible cells and pores in the reticulated matrix is very different from the porous structure formed by textile processing such as weaving, braiding and knitting and used to make grafts or graft jackets. The textile processes produce a more regular structure, do not have void content as high as reticulated matrix and do not have a system of interconnected and inter-communicating network of pores. In general, the three-dimensional form of structures made by textile processes have pore size that is on very rare occasions higher than 50 microns and the pore size of the reticulated elastomeric matrix is usually above 50 microns and more likely above 100 microns. The pore size of the reticulated elastomeric matrix, prior to thermal processing, compression molding, compressive molding or annealing is usually above 50 microns and more likely above 100 microns. In another embodiment, the morphology or structure of interconnected and inter-communicating network of accessible cells and pores in the reticulated matrix is very different from the porous structure formed by loss scaffold/leaching/lyophilization techniques. The porosity is not as high for scaffolds or structure made by scaffold/leaching/lyophilization techniques compared to reticulated matrix and the interconnectivity and accessibility for those techniques is also lower than reticulated matrix. Even in cases where porosities can be high, they still do not possess the high degree of interconnectivity between the cells and pores in the absence of a reticulation step. All the methods relating to loss scaffold/leaching/lyophilization techniques are made from thermoplastic polymers high molecular weights and when they dissolve form liquids with high viscosities; the high viscosities makes it physically impossible to form and grow inter-connected void phase or interconnected pores and cells within his highly viscous fluid. On the other hand in case of degradable urethane matrix, the formation of the pores and cells occurs simultaneously with the polymerization reaction so the pores and voids nucleate and grow in low viscosity and reticulation removes the cell membranes and the windows to provide the inter-connected and inter-communicating structure The control of pore size, interconnectivity of pores and the accessibility of scaffolds or structure made by lyophilization is lower than the reticulated matrix as is the mechanical properties of the scaffolds or structure made by lyophilization. Also the structures made by textile processes do not generally possess the same degree of elastomeric properties or are as resilient in recovery as reticulated elastomeric matrix. Other porous matrix made by processes such as electro-static spinning produce structures that do not have the same degree of inter-connected and inter-communicating network of accessible cells and pores as reticulated elastomeric matrix usually have lower void fraction compared to reticulated matrix and have pore size that are usually below 50 microns and in most cases below 30 microns. Also structures made by electro-static spinning, loss scaffold/leaching/lyophilization techniques being usually made from polymers that are predominantly thermoplastic in nature, are less elastomeric and less resilient in recovery compared to the reticulated elastomeric matrix. Also each of the foaming and reticulation processing steps take place in less than 10 minutes or in less than 5 minutes; the processing steps to make porous structure formed by loss scaffold/leaching/lyophilization techniques take several hours and in sometimes days to accomplish.

Size and Shape

Elastomeric matrix 10 can be readily fabricated in any desired size and shape. It is a benefit of the invention that elastomeric matrix 10 is suitable for mass production from bulk stock by subdividing such bulk stock, e.g., by cutting, die punching, laser slicing, or compression molding. In one embodiment, subdividing the bulk stock can be done using a heated surface. It is a further benefit of the invention that the shape and configuration of elastomeric matrix 10 may vary widely and can readily be adapted to desired anatomical morphologies.

The size, shape, configuration and other related details of elastomeric matrix 10 can be either customized to a particular application or patient or standardized for mass production. However, economic considerations may favor standardization. To this end, elastomeric matrix 10 or a composite mesh comprising reticulated elastomeric matrix 10 can be embodied in a kit comprising elastomeric implantable device pieces of different sizes and shapes. Also, as discussed elsewhere in the present specification and as is disclosed in the applications to which priority is claimed, multiple, e.g. two, three or four, individual elastomeric matrices 10 or composite mesh comprising reticulated elastomeric matrix 10 can be used as an implantable device system for a single target biological site, being sized or shaped or both sized and shaped to function cooperatively for treatment of an individual target site.

The practitioner performing the procedure, who may be a surgeon or other medical or veterinary practitioner, researcher or the like, may then choose one or more implantable devices from the available range to use for a specific treatment, for example, as is described in the applications to which priority is claimed in U.S. Patent Application Publication No. 2007/019108 and U.S. Patent Application Publication No. 2010/0318108, the disclosures of which are incorporated herein by this reference.

By way of example, the minimum dimension of elastomeric matrix 10 or a composite mesh comprising reticulated elastomeric matrix 10 may be as little as 0.5 mm and the maximum dimension as much as 100 mm or even greater. In another embodiment, the minimum dimension of elastomeric matrix 10 or composite mesh comprising reticulated elastomeric matrix 10 may be as little as 0.5 mm and the maximum dimension as much as 200 mm or even greater. However, in one embodiment it is contemplated that an elastomeric matrix 10 or a composite mesh comprising reticulated elastomeric matrix 10 of such dimension intended for implantation would have an elongated shape, such as the shapes of cylinders, rods, tubes or elongated prismatic forms, or a folded, coiled, helical or other more compact configuration. In another embodiment, it is contemplated that an elastomeric matrix 10 or composite mesh comprising reticulated elastomeric matrix 10 of such dimension intended for implantation would have a shape of a flat sheet or a long ribbon or a folded sheet with square or rectangular configuration. Comparably, a dimension as small as 0.5 mm can be a transverse dimension of an elongated shape or of a ribbon or sheet-like implantable device.

In an alternative embodiment, an elastomeric matrix 10 or a composite mesh comprising reticulated elastomeric matrix 10 having a spherical, cubical, tetrahedral, toroidal or other form having no dimension substantially elongated when compared to any other dimension and with a diameter or other maximum dimension of from about 0.5 mm to about 500 mm may have utility, for example, for an orthopedic application site, soft tissue defect site such as various forms of hernias, other soft tissue defect site for augmentation, support and ingrowth that require surgical meshes and wound healing sites and chronic wound healing sites In another embodiment, the elastomeric matrix 10 having such a form has a diameter or other maximum dimension from about 3 mm to about 20 mm.

For most implantable device applications, macrostructural sizes of elastomeric matrix 10 or a composite mesh comprising reticulated elastomeric matrix 10 include the following embodiments: compact shapes such as spheres, cubes, pyramids, tetrahedrons, cones, cylinders, trapezoids, parallelepipeds, ellipsoids, fusiforms, tubes or sleeves, and many less regular shapes having transverse dimensions of from about 1 mm to about 200 mm (In another embodiment, these transverse dimensions are from about 5 mm to about 100 mm.); and sheet- or strip-like shapes having a thickness of from about 0.5 to about 20 mm (In another embodiment, these thickness are from about 1 to about 5 mm.) and lateral dimensions of from about 5 to about 200 mm (In another embodiment, these lateral dimensions are from about 10 to about 100 mm.).

The inventors have investigated the use of an implantable elastomeric matrix 10 for orthopedic, hernia, surgical mesh, wound healing, and chronic wound healing applications. It was discovered that the matrix of the present invention provides unexpected benefits suitable for augmentation, support and ingrowth purposes. It is an advantage of the invention that the implantable elastomeric matrix 10 elements or composite mesh comprising reticulated elastomeric matrix 10 can be effectively employed without any need to closely conform to the configuration to the application site, which may often be complex and difficult to model. Another unexpected advantage of the invention is that the implantable elastomeric matrix elements or composite mesh comprising reticulated elastomeric matrix 10 embodiment is that when oversized with respect to the soft tissue defect which can be for orthopedic or hernia repair or wound healing applications, the implantable device conformally fits the tissue defect. Without being bound by any particular theory, the resilience and recoverable behavior that leads to such a conformal fit results in the formation of a tight boundary between the walls of the implantable device and the defect with substantially no clearance, thereby providing an interface conducive to the promotion of cellular ingrowth and tissue proliferation.

Furthermore, in one embodiment, the implantable device of the present invention, or implantable devices if more than one is used, should not completely fill the application site even when fully expanded in situ. In one embodiment, the fully expanded implantable device(s) of the present invention are smaller in a dimension than the application site and provide sufficient space within the application site to ensure vascularization, cellular ingrowth and proliferation, and for possible passage of blood to the implantable device. In another embodiment, the fully expanded implantable device(s) of the present invention are substantially the same in a dimension as the application site. In another embodiment, the fully expanded implantable device(s) of the present invention are larger in a dimension than the application site. In another embodiment, the fully expanded implantable device(s) of the present invention are smaller in volume than the application site. In another embodiment, the fully expanded implantable device(s) of the present invention are substantially the same volume as the application site. In another embodiment, the fully expanded implantable device(s) of the present invention are larger in volume than the application site.

In another embodiment, after being placed in the application site the expanded implantable device(s) of the present invention does not swell significantly or appreciably. The reticulated matrix or the implantable device(s) of the present invention are not considered to be an expansible material or a hydrogel or water swellable. The reticulated matrix is not considered to be a foam gel. The reticulated matrix does not expand swell on contact with bodily fluid or blood or water. In one embodiment, the reticulated matrix does not substantially expand or swell on contact with bodily fluid or blood or water.

Some useful implantable device shapes may approximate the contour of a portion of the target application site and in one embodiment, the resilient nature of the reticulated matrix allows for larger or slightly larger implantable device to compress appropriately in order to approximate the contour of a portion of the target application site. In one embodiment, the implantable device is shaped as relatively simple convex, dish-like or hemispherical or hemi-ellipsoidal shape or cylindrical and size that is appropriate for treating multiple different sites in different patients.

It is contemplated, in another embodiment, upon implantation, before their pores become filled with biological fluids, bodily fluids and/or tissue, such implantable devices for applications and the like do not entirely fill, cover or span the biological site in which they reside and that an individual implanted elastomeric matrix 10 or composite mesh comprising reticulated elastomeric matrix 10 will, in many cases although not necessarily, have at least one dimension of no more than 50% of the biological site within the entrance thereto or over 50% of the damaged tissue that is being repaired or replaced. In another embodiment, an individual implanted elastomeric matrix 10 or composite mesh comprising reticulated elastomeric matrix 10 as described above will have at least one dimension of no more than 75% of the biological site within the entrance thereto or over 75% of the damaged tissue that is being repaired or replaced. In another embodiment, an individual implanted elastomeric matrix 10 or composite mesh comprising reticulated elastomeric matrix 10 as described above will have at least one dimension of no more than 95% of the biological site within the entrance thereto or over 95% of the damaged tissue that is being repaired or replaced.

In another embodiment, upon implantation, before their pores become filled with biological fluids, bodily fluids and/or tissue, such implantable devices for applications and the like substantially fill, cover or span the biological site in which they reside and an individual implanted elastomeric matrix 10 or composite mesh comprising reticulated elastomeric matrix 10 will, in many cases, although not necessarily, have at least one dimension of no more than about 100% of the biological site within the entrance thereto or cover 100% of the damaged tissue that is being repaired or replaced. In another embodiment, an individual implanted elastomeric matrix 10 or composite mesh comprising reticulated elastomeric matrix 10 as described above will have at least one dimension of no more than about 98% of the biological site within the entrance thereto or cover 98% of the damaged tissue that is being repaired or replaced. In another embodiment, an individual implanted elastomeric matrix 10 or composite mesh comprising reticulated elastomeric matrix 10 as described above will have at least one dimension of no more than about 102% of the biological site within the entrance thereto or cover 102% of the damaged tissue that is being repaired or replaced.

In another embodiment, upon implantation, before their pores become filled with biological fluids, bodily fluids and/or tissue, such implantable devices for applications such as soft tissue orthopedic defect, hard tissue orthopedic defect, soft tissue defect site such as various forms of hernias, other soft tissue defect site for augmentation, support and ingrowth that require surgical meshes and wound healing sites and the like over fill, cover or span the biological site in which they reside and an individual implanted elastomeric matrix 10 or composite mesh comprising reticulated elastomeric matrix 10 will, in many cases, although not necessarily, have at least one dimension of more than about 105% of the biological site within the entrance thereto or cover 105% of the damaged tissue that is being repaired or replaced. In another embodiment, an individual implanted elastomeric matrix 10 as described above will have at least one dimension of more than about 125% of the biological site within the entrance thereto or cover 125% of the damaged tissue that is being repaired or replaced. In another embodiment, an individual implanted elastomeric matrix 10 as described above will have at least one dimension of more than about 150% of the biological site within the entrance thereto or cover 150% of the damaged tissue that is being repaired or replaced. In another embodiment, an individual implanted elastomeric matrix 10 or composite mesh comprising reticulated elastomeric matrix 10 as described above will have at least one dimension of more than about 200% of the biological site within the entrance thereto or cover 200% of the damaged tissue that is being repaired or replaced. In another embodiment, an individual implanted elastomeric matrix 10 or composite mesh comprising reticulated elastomeric matrix 10 as described above will have at least one dimension of more than about 300% of the biological site within the entrance thereto or cover 300% of the damaged tissue that is being repaired or replaced.

One embodiment for use in the practice of the invention is a reticulated elastomeric matrix 10 which is sufficiently flexible and resilient, i.e., resiliently-compressible, to enable it to be initially compressed under ambient conditions, e.g., at 25° C., from a relaxed configuration to a first, compact configuration for delivery via a delivery-device, e.g., catheter, endoscope, syringe, cystoscope, trocar or other suitable introducer instrument, for delivery in vitro and, thereafter, to expand to a second, working configuration in situ. Furthermore, in another embodiment, an elastomeric matrix can have the herein described resilient-compressibility after being compressed about 5-95% of an original dimension (e.g., compressed about $^{19}/_{20}$th-$^{1}/_{20}$th of an original dimension). In another embodiment, an elastomeric matrix can have the herein described resilient-compressibility after being compressed about 10-90% of an original dimension (e.g., compressed about $^{9}/_{10}$th-$^{1}/_{10}$th of an original dimension). As used herein, elastomeric matrix 10 can have "resilient-compressibility", i.e., is "resiliently-compressible", when the second, working configuration, in vitro, is at least about 50% of the size of the relaxed configuration in at least one dimension. In another embodiment, the resilient-compressibility of elastomeric matrix 10 is such that the second, working configuration, in vitro, is at least about 80% of the size of the relaxed configuration in at least one dimension. In another embodiment, the resilient-compressibility of elastomeric matrix 10 is such that the second, working configuration, in vitro, is at least about 90% of the size of the relaxed configuration in at least one dimension. In another embodiment, the resilient-compressibility of elastomeric matrix 10 is such that the second, working configuration, in vitro, is at least about 97% of the size of the relaxed configuration in at least one dimension.

In another embodiment, an elastomeric matrix can have the herein described resilient-compressibility after being compressed about 5-95% of its original volume (e.g., compressed about ¹⁹⁄₂₀th-¹⁄₂₀th of its original volume). In another embodiment, an elastomeric matrix can have the herein described resilient-compressibility after being compressed about 10-90% of its original volume (e.g., compressed about ⁹⁄₁₀th-¹⁄₁₀th of its original volume). As used herein, "volume" is the volume swept-out by the outermost 3-dimensional contour of the elastomeric matrix. In another embodiment, the resilient-compressibility of elastomeric matrix 10 is such that the second, working configuration, in vivo, is at least about 50% of the volume occupied by the relaxed configuration. In another embodiment, the resilient-compressibility of elastomeric matrix 10 is such that the second, working configuration, in vivo, is at least about 80% of the volume occupied by the relaxed configuration. In another embodiment, the resilient-compressibility of elastomeric matrix 10 is such that the second, working configuration, in vivo, is at least about 90% of the volume occupied by the relaxed configuration. In another embodiment, the resilient-compressibility of elastomeric matrix 10 is such that the second, working configuration, in vivo, occupies at least about 97% of the volume occupied by the elastomeric matrix in its relaxed configuration.

One embodiment for use in the practice of the invention is a reticulated elastomeric matrix or a composite mesh comprising reticulated elastomeric matrix which is sufficiently flexible and resilient, i.e., resiliently-compressible, to enable it to be initially compressed under ambient conditions, e.g., at 25° C., from a relaxed configuration to a first, compact configuration for delivery via a delivery-device, e.g., catheter, endoscope, syringe, cystoscope, trocar or other suitable introducer instrument, for delivery in vitro and, thereafter, to expand to a second, working configuration in situ.

Elastomeric Matrix Physical Properties

A reticulated at least partially or fully degradable elastomeric matrix 10, an implantable device comprising a reticulated elastomeric matrix, can have any suitable bulk density, also known as specific gravity, consistent with its other properties. In another embodiment, Elastomeric matrix 10, a reticulated at least partially or fully degradable elastomeric matrix, an implantable device comprising a reticulated elastomeric matrix, and/or an implantable device comprising a compressive molded reticulated elastomeric matrix can have any suitable bulk density, also known as specific gravity, consistent with its other properties. For example, in one embodiment, the bulk density, as measured pursuant to the test method described in ASTM Standard D3574, may be from about 0.008 g/cc to about 0.96 g/cc (from about 0.50 lb/ft³ to about 60 lb/ft³). In another embodiment, the bulk density may be from about 0.016 g/cc to about 0.56 g/cc (from about 1.0 lb/ft³ to about 35 lb/ft³). In another embodiment, the bulk density may be from about 0.008 g/cc to about 0.15 g/cc (from about 0.50 lb/ft³ to about 9.4 lb/ft³). In another embodiment, the bulk density may be from about 0.008 g/cc to about 0.127 g/cc (from about 0.5 lb/ft³ to about 8 lb/ft³). In another embodiment, the bulk density may be from about 0.008 g/cc to about 0.288 g/cc (from about 0.5 lb/ft³ to about 18 lb/ft³). In another embodiment, the bulk density may be from about 0.016 g/cc to about 0.115 g/cc (from about 1.0 lb/ft³ to about 7.2 lb/ft³). In another embodiment, the bulk density may be from about 0.024 g/cc to about 0.104 g/cc (from about 1.5 lb/ft³ to about 6.5 lb/ft³).

Elastomeric matrix 10 can have any suitable microscopic surface area consistent with its other properties. From an exposed plane of the porous material, one can estimate the microscopic surface area from the pore frequency, e.g., the number of pores per linear millimeter, and can routinely estimate the pore frequency from the average cell side diameter in μm.

Elastomeric Matrix Mechanical Properties

In one embodiment, at least partially degradable or fully degradable reticulated elastomeric matrix 10 can have sufficient structural integrity to be self-supporting and free-standing in vitro. However, in another embodiment, elastomeric matrix 10 can be furnished with structural supports such as ribs or struts or reinforcements.

The at least partially degradable or fully degradable reticulated elastomeric matrix 10 has sufficient tensile strength such that it can withstand normal manual or mechanical handling during its intended application and during post-processing steps that may be required or desired without tearing, breaking, crumbling, fragmenting or otherwise disintegrating, shedding pieces or particles, or otherwise losing its structural integrity. The tensile strength of the starting material(s) should not be so high as to interfere with the fabrication or other processing of elastomeric matrix 10.

Thus, for example, in one embodiment at least partially degradable or fully degradablereticulated elastomeric matrix 10 may have a tensile strength of from about 7000 kg/m² to about 105,000 kg/m² (from about 10 psi to about 150 psi). In another embodiment, elastomeric matrix 10 may have a tensile strength of from about 10,500 kg/m² to about 70,000 kg/m² (from about 15 psi to about 100 psi). In another embodiment, reticulated elastomeric matrix 10 may have a tensile modulus of from about 7,000 kg/m² to about 63,000 kg/m² (from about 10 psi to about 90 psi). In another embodiment, elastomeric matrix 10 may have a tensile strength of from about 2,100 kg/m² to about 10,500 kg/m² (from about 3 psi to about 150 psi).

Sufficient ultimate tensile elongation is also desirable. For example, in another embodiment, at least partially degradable or fully degradable reticulated elastomeric matrix 10 can have an ultimate tensile elongation of at least about 50%. In another embodiment, elastomeric matrix 10 can have an ultimate tensile elongation of at least about 75%. In another embodiment, elastomeric matrix 10 can have an ultimate tensile elongation of at least about 125%. In another embodiment, elastomeric matrix 10 can have an ultimate tensile elongation of at least about 150%. In another embodiment, elastomeric matrix 10 can have an ultimate tensile elongation of at least about 200%. In one embodiment, these high elongation to break makes these at least partially degradable or fully degradable reticulated matrix comprise elastomeric properties. In another embodiment, these high elongation to break coupled with low modulus make these at least partially degradable or fully degradable reticulated matrix comprise elastomeric properties. The elastomeric nature of these at least partially degradable or fully degradable reticulated elastomeric matrix arises from their cross-linked structure which allows for high elongation to beak or high strain to failure.

In one embodiment, reticulated elastomeric matrix 10 may have a compressive modulus of from about 7,000 kg/m² to about 63,000 kg/m² (from about 10 psi to about 90 psi). In another embodiment, reticulated elastomeric matrix 10 can have a compressive strength of from about 70 kg/m² to about 350,00 kg/m² (from about 0.1 psi to about 50 psi) at 50% compression strain. In another embodiment, reticulated elastomeric matrix 10 can have a compressive strength of from about 140 kg/m² to about 21,100 kg/m² (from about 0.2 psi to about 30 psi) at 50% compression strain.

In one embodiment, the elastomeric matrix 10 is allowed to expand from the first, compact configuration to the second, working configuration over a short time, e.g., about 90% recovery in 90 seconds or less in one embodiment, or in 40 seconds or less in another embodiment, each from 75% compression strain held for up to 10 minutes. In another embodiment, the expansion from the first, compact configuration to the second, working configuration can occur over a short time, e.g., about 95% recovery in 180 seconds or less in one embodiment, in 90 seconds or less in another embodiment, in 60 seconds or less in another embodiment, each from 75% compression strain held for up to 30 minutes. In another embodiment, elastomeric matrix 10 can recover in about 10 minutes to occupy at least about 97% of the volume occupied by its relaxed configuration, following 75% compression strain held for up to 30 minutes. In another embodiment, the expansion from the first, compact configuration to the second, working configuration can occur over a short time, e.g., about 90% recovery in 180 seconds or less in one embodiment, in 90 seconds or less in another embodiment, in 60 seconds or less in another embodiment, in 30 seconds or less in another embodiment, each from 50% compression strain held for up to 120 minutes. In one embodiment, the elastomeric matrix 10 is allowed to expand from the first, compact configuration to the second, working configuration over a short time, e.g., about 90% recovery in 400 minutes or less in one embodiment, or in 150 minutes or less in another embodiment, or in 75 minutes or less in another embodiment, or in 50 minutes or less in another embodiment, or in 10 minutes or less in another embodiment, or in 3 minutes or less in another embodiment, each from 50% compression strain held for up to 120 minutes. In one embodiment, the elastomeric matrix 10 is allowed to expand from the first, compact configuration to the second, working configuration over a short time, e.g., about 90% recovery in about 5 hours or less in one embodiment, or in about 1 hour or less in another embodiment, or in 600 seconds or less in another embodiment, or in 300 seconds or less in another embodiment, or in 90 seconds or less in another embodiment, or in 30 seconds or less in another embodiment, each from 75% compression strain held for up to 10 minutes. This recovery is due to the resilient nature of the at least partially degradable or fully degradable elastomeric matrix.

The mechanical properties of the porous materials described herein, if not indicated otherwise, may be determined according to ASTM D3574-01 entitled "Standard Test Methods for Flexible Cellular Materials—Slab, Bonded and Molded Urethane Foams", or other such method.

Furthermore, if porosity is to be imparted to the elastomer employed for elastomeric matrix 10 after rather than during the polymerization reaction, good processability is also desirable for post-polymerization shaping and fabrication. For example, in one embodiment, elastomeric matrix 10 can have low tackiness.

Elastomeric Matrices from Elastomer Polymerization, Cross-Linking and Foaming

In further embodiments, the invention provides a porous at least partially degradable elastomer or fully degradable elastomer and a process for polymerizing, cross-linking and foaming and reticulating the same which can be used to produce an at least partially degradable or fully degradable reticulated elastomeric matrix 10 as described herein. In another embodiment, the invention provides a porous at least partially degradable elastomer or fully degradable elastomer and a process for polymerizing, foaming and optional cross-linking and reticulating the same which can be used to produce an at least partially degradable or fully degradable reticulated elastomeric matrix 10 as described herein. In one embodiment, the degradation characteristics reticulated elastomeric matrix 10 as described herein can be controlled or engineered.

The polymerization reaction between isocyanate with polyol in the optional presence of chain extenders, cross-linking agent, surfactants, catalysts and processing aids leads to the formation of a segmented polyurethane polymer matrix with hard segments derived from isocyanate and soft segments derived from polyols and formation of urethane bonds or linkages. The polymerization reaction is accompanied by a second reaction between isocyanate and water, which produces the urea bonds or linkages with simultaneous formation of carbon dioxide ($CO_2$). Release of the $CO_2$, also termed as a foaming reaction, aids in the formation of a porous matrix with cellular structure. In one embodiment, cross-links are present in this material. The segmented matrix formed is elastomeric and demonstrates resilient recovery after being deformed under both compression and tension. This matrix is then subjected to optional curing at room temperature or at an elevated temperature that ensures the further reaction of the un-reacted starting components that may not have reacted during foam formation. For the purpose of this invention gelation is the polymeric reaction associated with urethane production and which produces a solid material from the liquid components. In one embodiment, gelation comprises formation of urethane bonds or linkages and urea bonds or linkages as well as the solidification of the polyols. In one embodiment, gelation comprises provide dimensional and structural stability. In embodiment, curing at least partially anneals the matrix so as to release any stresses imparted during processing and provide dimensional and structural stability.

The porous matrix is then reticulated, or subjected to removal of the windows or membranes formed between the struts that comprise the porous structure and are formed during the foaming process. In one embodiment in the reticulation process, a gas mixture with a combustible ratio of hydrogen to oxygen gas is introduced into the porous matrix placed in a sealed chamber and the gas in the chamber is then ignited with a spark, and the resultant combustion process causes rapid propagation of hot gases through the cellular structure of the matrix. In one embodiment, the high pressure and temperature generated during the process ruptures and melts the thin cell windows of the porous matrix and wraps them around the remaining struts. In one embodiment, the high pressure and temperature generated during the process ruptures the cell windows of the porous matrix. Removal of the cell windows creates a continuous passage throughout the entire matrix, and the porous matrix is now a reticulated matrix characterized by inter-connected and intercommunicating cells and pores. According to an aspect, the polyurethane matrix is reticulated to a Darcy permeability of at least 50 or in one embodiment 100 or in one embodiment, at least 150 or in another embodiment, at least 200. The thin windows or membranes formed during the foaming process needs to be at least partially ruptured or broken to allow for passage of the reticulation gas. These ruptured or broken windows or membranes do not allow for fluid transport or tissue ingrowth and has a low Darcy permeability of about 10 or less and in another embodiment of 15 or less. If the thin windows or membranes do not allow for passage of the reticulation gas, the matrix is considered to have closed cell porous structure.

More particularly, in another embodiment, the invention provides a process for preparing an at least partially degradable elastomeric polyurethane matrix which comprises synthesizing the matrix from a polyol component comprising polycaprolactone or its copolymers and an isocyanate component by polymerization, cross-linking and foaming, thereby forming pores, followed by reticulation of the foam to provide a reticulated product. In one embodiment, the product is optional. In this embodiment, the product is designated as a polycaprolactone polyurethane, being a polymer comprising urethane groups formed from, e.g., the hydroxyl groups of the polycaprolactone polyol component and the isocyanate groups of the isocyanate component. In another embodiment, the product is designated as a polycaprolactone urea-urethane, being a polymer comprising urethane groups formed from, e.g., the hydroxyl groups of the polycaprolactone polyol component and the isocyanate groups of the isocyanate component and urea linkages or groups formed from reaction of isocyanate component with water component used for foaming. In this embodiment, the process employs controlled chemistry to provide a reticulated elastomer product with controlled degradable characteristics that can be at least partially or fully degradable. In one embodiment, controlled degradation characteristics can be obtained from the chemistry of the polyol-derived soft segments that comprise of aliphatic polyesters whose hydrolytic degradation rates can be controlled. In one embodiment, controlled degradation characteristics can be obtained from degree and extent of cross-linking. In one embodiment, controlled degradation characteristics can be obtained from degree and extent of chain extension. In another embodiment, controlled degradation characteristics can be obtained from the molecular weight of the polyol-derived soft segments or the relative molecular weights of the copolymers of the polyol-derived soft segments. In one embodiment, one specific degradation characteristics can be obtained through multiple paths or differing chemistries obtained as a combination of all factors or some factors selected from the chemistry of the polyol-derived soft segments, the molecular weight of the polyol-derived soft segments, relative molecular weights of the copolymers of the polyol-derived soft segments, degree and extent of cross-linking and degree and extent of chain extension. Pursuant to the invention, the polymerization can be conducted to provide a foam product employing chemistry that avoids biologically undesirable or nocuous constituents therein.

In one embodiment, as one starting material, the process employs at least one polyol component. For the purposes of this application, the term "polyol component" includes molecules comprising, on the average, about 2 hydroxyl groups per molecule, i.e., a difunctional polyol or a diol, as well as those molecules comprising, on the average, greater than about 2 hydroxyl groups per molecule, i.e., a polyol or a multi-functional polyol. Exemplary polyols can comprise, on the average, from about 2 to about 5 hydroxyl groups per molecule. In one embodiment, as one starting material, the process employs a difunctional polyol component. In this embodiment, because the hydroxyl group functionality of the diol is about 2, it does not provide the so-called "soft segment" with soft segment cross-linking. In another embodiment, as one starting material of the polyol component, the process employs a multi-functional polyol component in sufficient quantity to provide a controlled degree of soft segment cross-linking. In another embodiment, the process provides sufficient soft segment cross-linking to yield a stable foam. In another embodiment, the soft segment is composed of a polyol component that is generally of a relatively low molecular weight, in one embodiment from about 350 to about 6,000 Daltons, and from about 450 to about 4,000 Daltons in another embodiment. In another embodiment, the molecular weight of the polyol component is from about 1000 to about 3,000 Daltons. In another embodiment, the molecular weight of the polyol component is from about 750 to about 3,500 Daltons. In another embodiment, the molecular weight of the polyol component is above about 750 Daltons. Thus, these polyols are generally liquids or low-melting-point solids. This soft segment polyol is terminated with hydroxyl groups, either primary or secondary. In another embodiment, a soft segment polyol component has about 2 hydroxyl groups per molecule. In another embodiment, a soft segment polyol component has greater than about 2 hydroxyl groups per molecule; more than 2 hydroxyl groups per polyol molecule are required of some polyol molecules to impart soft-segment cross-linking. In one embodiment, controlled degradation characteristics or the degradation rate of the reticulated elastomeric matrix can be obtained from the molecular weight of the polyol-derived soft segments or the relative molecular weights of the copolymers of the polyol-derived soft segments.

In one embodiment, the average number of hydroxyl groups per molecule in the polyol component is about 2. In another embodiment, the average number of hydroxyl groups per molecule in the polyol component is greater than about 2. In another embodiment, the average number of hydroxyl groups per molecule in the polyol component is greater than 2. In one embodiment, the polyol component comprises a tertiary carbon linkage. In one embodiment, the polyol component comprises a plurality of tertiary carbon linkages.

In one embodiment, the polyol component is a polycaprolactone-polyethylene glycol polyurethanes, polycaprolactone-polyethylene glycol urea-urethane, polycaprolactone polyol, polyester polyol, glycolide polyol, l-lactide polyol, d-l lactide polyol, polyether polyol, poly(ether-co-ester) polyol, poly (caprolactone-co-glycolide)polyol, poly (caprolactone-co-l-lactide) polyol, poly (caprolactone-co-d-l-lactide)polyol, poly (caprolactone-co-para-dioxanone) polyol, (caprolactone-co-l-lactide-co glycolide)polyol, poly (caprolactone-co-glycolide-co-d-l lactide)polyol, poly (caprolactone-co-l-lactide-co-d-l lactide)polyol, poly(caprolactone-co-carbonate)polyol, poly(caprolactone-co-siloxane)polyol, polyol, poly(caprolactone-co-hydrocarbon)polyol, polyethylene glycol polyol, polyvivyl alcohol, polysaccharide polyol, polyols containing starch, polyols containing various forms of sugars, polyols containing cellulose, polyols containing chitin and chitosan, polyols containing cellulose, or a mixture thereof. In another embodiment, the polyol component comprises polycaprolactone polyol or copolymers of polycaprolactone. In another embodiment, the polyol component comprises polycaprolactone or copolymers of polycaprolactone. The mole percentage of caprolactone in the copolymer polyol varies from 30% to 97%. In another embodiment, the mole percentage of caprolactone in the copolymer polyol varies from 40% to 95%. In another embodiment, the mole percentage of caprolactone in the copolymer polyol varies from 60% to 95%. In another embodiment, the mole percentage of caprolactone in the copolymer polyol varies from 70% to 95%. In another embodiment, the mole percentage of caprolactone in the copolymer polyol varies from 80% to 95%. If the poly caprolactone polyol is a solid at 25° C., it is typically melted prior to further processing.

In one embodiment, fillers or diluents or additives such as starch, sugar, cellulose, chitin and chitosan, polyethylene glycol polyol, polyvinyl alcohol, collagen, Hyaluronic acid, etc, can be added to polycaprolactone polyol or copolymers of polycaprolactone used to make at least partially of fully degradable elastomeric matrix. The amount of fillers or diluents or additives can vary from 1 to 50% by weight of the polycaprolactone polyol or copolymers of polycaprolactone in one embodiment and can vary from 3 to 30% in another embodiment and can vary from 5 to 25% in another embodiment.

The soft segment of the partially degradable and fully degradable reticulated elastomeric matrix comprises the polyol and will at least partially degrade or at least partially hydrolyze or at least partial absorb or bioabsorb over time. In another embodiment, the soft segment part comprising polyol component will completely degrade or hydrolyze or absorb or bioabsorb over time. In another embodiment, the polyol component comprising polycaprolactone will completely degrade or hydrolyze or absorb or bioabsorb over time. The soft segment part comprising polyol component will degrade by hydrolysis and lose it mechanical properties or integrity over time. The degradation rate and time of the soft segment will depend on the composition of these hydrolysable polyols. In one embodiment, it is expected that that for copolymer polyols where the polycaprolactone is the major component and for the same polycaprolactone content, polyols containing glycolide will degrade fastest rate, polyols containing l-lactide will degrade at a slowest rate and polyol containing d-l-lactide will degrade at an intermediate rate. In one embodiment, it is expected that that for copolymer polyols where the polycaprolactone is greater than or about 60 mole % in the copolymer polyol, polyols containing glycolide will degrade fastest rate, polyols containing l-lactide will degrade at a slowest rate and polyol containing d-l-lactide will degrade at an intermediate rate. In one embodiment, it is expected that that for copolymer polyols where the polycaprolactone is greater than or about 70 mole % in the copolymer polyol, polyols containing glycolide will degrade fastest rate, polyols containing l-lactide will degrade at a slowest rate and polyol containing d-l-lactide will degrade at an intermediate rate. In one embodiment, it is expected that that for copolymer polyols where the polycaprolactone is greater than or about 80 mole % in the copolymer polyol, polyols containing glycolide will degrade fastest rate, polyols containing l-lactide will degrade at a slowest rate and polyol containing d-l-lactide will degrade at an intermediate rate. In one embodiment, in copolymer polyols containing multiple copolymers other than polycaprolactone such as poly(caprolactone-co-glycolide-co-lactide)polyol, poly(caprolactone-co-glycolide-co-d/l lactide)polyol, poly(caprolactone-co-lactide-co-d/l lactide)polyol, the ratio of the ingredients including polycaprolactone will determine the degradation rate. Degradation of the soft segment of the at least partially degradable or fully degradable elastomeric matrix occurs owing to hydrolytic degradation and possibly also due to enzymatic degradation. Degradation of both hard and soft segments of the fully degradable elastomeric matrix occurs owing to hydrolytic degradation and possibly also due to enzymatic degradation.

In one embodiment, copolymer polyols where the polycaprolactone is higher will degrade at a slower rate than the copolymer polyols where the polycaprolactone is lower. In one embodiment, copolymer polyols where the polycaprolactone is higher is more elastomeric or more resilient in recovery compare to the copolymer polyols where the polycaprolactone is lower.

The degradable part of the partially degradable matrix comprising of the degradable polyol component will degrade or hydrolyze or absorb or bioabsorb over a period of time in about 30 days or in another embodiment in 60 days. In another embodiment, degradable part of the partially degradable matrix comprising of the degradable polyol component will degrade or hydrolyze or absorb or bioabsorb over a period of time in about 180 days. In another embodiment, degradable part of the partially degradable matrix comprising of the degradable polyol component will degrade or hydrolyze or absorb or bioabsorb over a period of time in about 1 year. In another embodiment, degradable part of the partially degradable matrix comprising of the degradable polyol component will degrade or hydrolyze or absorb or bioabsorb over a period of time in about 2 years. In another embodiment, degradable part of the partially degradable matrix comprising of the degradable polyol component will degrade or hydrolyze or absorb or bioabsorb over a period of time in greater than 2 years and in another embodiment in greater than 5 years. The fully degradable matrix comprising of the degradable polyol component and degradable isocyanate component will degrade or hydrolyze or absorb or bioabsorb over a period of time in about 180 days or in another embodiment in 60 days. In another embodiment, the fully degradable matrix comprising of the degradable polyol component and degradable isocyanate component will degrade or hydrolyze or absorb or bioabsorb over a period of time in about 1 year. In another embodiment, the fully degradable matrix comprising of the degradable polyol component and degradable isocyanate component will degrade or hydrolyze or absorb or bioabsorb over a period of time in about 2 years. In another embodiment, the fully degradable matrix comprising of the degradable polyol component and degradable isocyanate component will degrade or hydrolyze or absorb or bioabsorb over a period of time in greater than 2 years and in another embodiment in greater than 5 years.

A particular type of polyol need not be limited to those formed from a single monomeric unit. For example, a polyether-type polyol can be formed from a mixture of ethylene oxide and propylene oxide. In another example poly (caprolactone-co-l-lactide)polyol can comprise of caprolactone and l-lactic acid. In another example poly (caprolactone-co-glycolide) polyol can comprise of caprolactone and glycolic acid. In another example poly (caprolactone-co d-l lactide) polyol can comprise of caprolactone and d-l lactide. In another example poly (caprolactone-co paradioxanone) polyol can comprise of caprolactone and poly(paradioxanone). In another example poly poly(caprolactone-co-glycolide-co-lactide)polyol can comprise of caprolactone, lactic acid and glycolic acid. In another example poly poly(caprolactone-co-glycolide-co-d/l lactide)polyol can comprise of caprolactone, d/l lactide and glycolic acid. Furthermore, in another embodiment, mixtures, admixtures and/or blends of polyols and copolyols can be used in the elastomeric matrix of the present invention. In another embodiment, the molecular weight of the polyol is varied. In another embodiment, the functionality of the polyol is varied. In another embodiment, if difunctional polyols cannot, on their own, induce soft segment cross-linking, higher functionality is introduced into the formulation through the use of a chain extender component with a hydroxyl group functionality greater than about 2. In another embodiment, higher functionality is introduced through the use of an isocyanate component with an isocyanate group functionality greater than about 2.

The process also employs at least one isocyanate component and, optionally, at least one chain extender component to provide the so-called "hard segment". For the purposes of this application, the term "isocyanate component" includes molecules comprising, on the average, about 2 isocyanate groups per molecule as well as those molecules comprising, on the average, greater than about 2 isocyanate groups per molecule. The isocyanate groups of the isocyanate component are reactive with reactive hydrogen groups of the other ingredients, e.g., with hydrogen bonded to oxygen in hydroxyl groups and with hydrogen bonded to nitrogen in amine groups of the polyol component, chain extender, cross-linker and/or water.

In one embodiment, the average number of isocyanate groups per molecule in the isocyanate component is about 2. In another embodiment, the average number of isocyanate groups per molecule in the isocyanate component is greater than about 2. In another embodiment, the average number of isocyanate groups per molecule in the isocyanate component is greater than 2. In another embodiment, the number of isocyanate groups per molecule in the isocyanate component is greater than 2 which allows for cross-linking of elastomeric matrix. In one embodiment, the number of isocyanate groups per molecule in the isocyanate component is greater than 2 which allows for cross-linking of isocyanate comprising hard segment. In one embodiment, controlled degradation characteristics of the reticulated elastomeric matrix can be obtained from degree and extent of cross-linking. In another embodiment, the degradation rate of the reticulated elastomeric matrix can be obtained from degree and extent of cross-linking.

The soft segment part of the partially degradable and fully degradable reticulated elastomeric matrix comprises the polyol and constitutes about 50 to about 90 mole percent. In another embodiment, the soft segment of the partially degradable and fully degradable reticulated elastomeric matrix comprises the polyol and constitutes about 40 to about 80 mole percent. In another embodiment, the soft segment of the partially degradable and fully degradable reticulated elastomeric matrix comprises the polyol and constitutes about 50 to about 80 mole percent or in another embodiment from about 55 to about 75 mole percent. In another embodiment, the soft segment of the partially degradable and fully degradable reticulated elastomeric matrix comprises the polyol and constitutes about 60 to about 80 mole percent. In another embodiment, the soft segment of the partially degradable and fully degradable reticulated elastomeric matrix comprises the polyol and constitutes about 65 to about 75 mole percent. The hard segment comprising the isocyanate, the cross-linker and the optional chain extender comprises the remaining mole percent.

The isocyanate index is the mole ratio of the number of isocyanate groups in a formulation available for reaction to the number of groups in the formulation that are able to react with those isocyanate groups, e.g., the reactive groups of diol(s), polyol component(s), chain extender(s) and water, when present. In one embodiment, the isocyanate index is from about 0.9 to about 1.1. In another embodiment, the isocyanate index is from about 0.85 to about 1. In another embodiment, the isocyanate index is from about 0.85 to about 1.01. In another embodiment, the isocyanate index is from about 0.9 to about 1.02. In another embodiment, the isocyanate index is from about 0.98 to about 1.02. In another embodiment, the isocyanate index is from about 0.95 to about 1.025. In another embodiment, the isocyanate index is from about 0.9 to about 1.0. In another embodiment, the isocyanate index is from about 0.85 to about 1.05. In another embodiment, the isocyanate index is from about 0.90 to about 1.0. In another embodiment, the isocyanate index is below 1.02. In another embodiment, the isocyanate index is below 1.01. In another embodiment, the isocyanate index is below 1.0. In another embodiment, the isocyanate index is from about 0.9 to about 0.98. In another embodiment, the isocyanate index is from about 0.9 to about 1.05. In another embodiment, the isocyanate index is from about 0.85 to about 1.1.

The hard segment is derived from the isocyanate component. Exemplary diisocyanates for at least partially degradable reticulated elastomeric matrix include aliphatic diisocyanates, isocyanates comprising aromatic groups, the so-called "aromatic diisocyanates", or a mixture thereof. Aliphatic diisocyanates include tetramethylene diisocyanate, cyclohexane-1,2-diisocyanate, cyclohexane-1,4-diisocyanate, 1,4-butanediisocyanate, hexamethylene diisocyanate, isophorone diisocyanate, methylene-bis-(p-cyclohexyl isocyanate) ("$H_{12}$ MDI"), cyclohexyl diisocyanate, or a mixture thereof. Aromatic diisocyanates include p-phenylene diisocyanate, 4,4'-diphenylmethane diisocyanate ("4,4'-MDI"), 2,4'-diphenylmethane diisocyanate ("2,4'-MDI"), 2,4-toluene diisocyanate ("2,4-TDI"), 2,6-toluene diisocyanate ("2,6-TDI"), m-tetramethylxylene diisocyanate, or a mixture thereof.

Exemplary isocyanate components for at least partially degradable reticulated elastomeric matrix comprising, on the average, greater than about 2 isocyanate groups per molecule, include an adduct of hexamethylene diisocyanate and water comprising about 3 isocyanate groups, available commercially as MONDUR 1488, Mondur 1488 and Mondur MRS 20 from Bayer, RUBINATE 9433 and RUBINATE 9258, each from Huntsman, $H_{12}$ MDI, such as DESMODUR W from Bayer and a trimer of hexamethylene diisocyanate comprising about 3 isocyanate groups, available commercially as MONDUR N3390 from Bayer.

In one embodiment, for at least partially degradable reticulated elastomeric matrix the preferred isocyanate component contains a mixture of at least about 5% by weight of 2,4'-MDI with the balance 4,4'-MDI. In another embodiment, the isocyanate component contains a mixture of at least 5% by weight of 2,4'-MDI with the balance 4,4'-MDI. In another embodiment, the isocyanate component contains a mixture of from about 5% to about 50% by weight of 2,4'-MDI with the balance 4,4'-MDI. In another embodiment, the isocyanate component contains a mixture of from 5% to about 50% by weight of 2,4'-MDI with the balance 4,4'-MDI. In another embodiment, the isocyanate component contains a mixture of from about 5% to about 40% by weight of 2,4'-MDI with the balance 4,4'-MDI. In another embodiment, the isocyanate component contains a mixture of from 5% to about 40% by weight of 2,4'-MDI with the balance 4,4'-MDI. In another embodiment, the isocyanate component contains a mixture of from 5% to about 35% by weight of 2,4'-MDI with the balance 4,4'-MDI. Without being bound by any particular theory, it is thought that the use of higher amounts of 2,4'-MDI in a blend with 4,4'-MDI results in a softer elastomeric matrix because of the disruption of the crystallinity of the hard segment arising out of the asymmetric 2,4'-MDI structure. Also. Without being bound by any particular theory, it is thought that the use of higher amounts of 2,4'-MDI in a blend with 4,4'-MDI results in a softer elastomeric matrix because of the disruption of the stereo regularity of the hard segment arising out of the asymmetric 2,4'-MDI structure. It is believed that the disruption of the crystallinity or the stereo regularity of the hard segment arising out of the asymmetric 2,4'-MDI structure, provides a less stiffer structure for the reticulated elastomeric matrix.

Exemplary diisocyanates for fully or completely degradable reticulated elastomeric matrix include suitable aliphatic polyisocyanates include lysine methyl ester diisocyanate, lysine triisocyanate, amino acid lysine based diisocyanate and include the degradable diisocyanate described in U.S. Pat. No. 6,221,997.

In another embodiment, exemplary diisocyanates for fully or completely degradable reticulated elastomeric matrix include various hydrolytically-degradable, bridged diphenyl diisocyanates described in US patent application 2006/0188547.

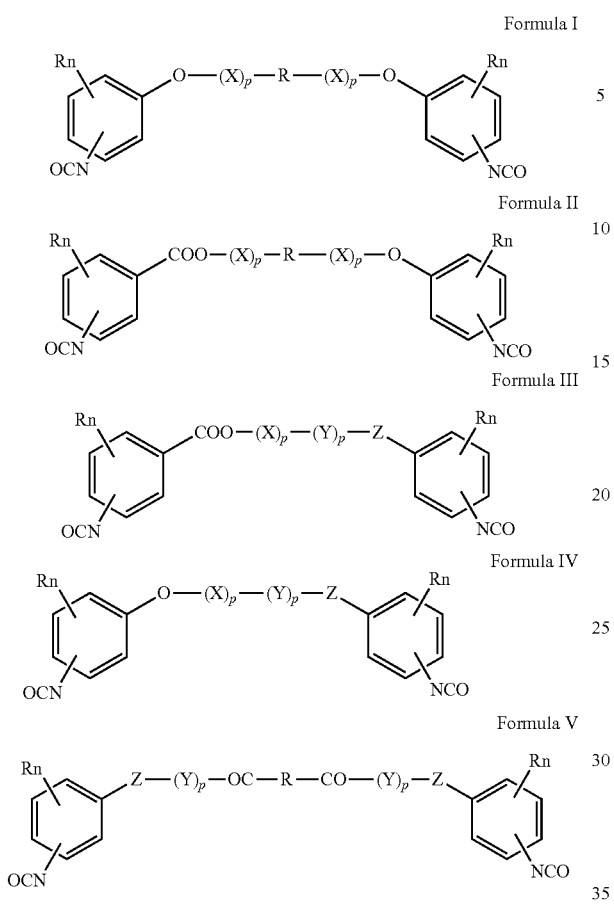

Formula I
Formula II
Formula III
Formula IV
Formula V

Wherein each X represents a member independently selected from:
a) —CH2COO— (glycolic acid moiety);
b) —CH(CH3)COO— (lactic acid moiety);
c) —CH2CH2OCH2COO— (dioxanone moiety);
d) —CH2CH2CH2CH2CH2COO— (caprolactone moiety);
e) —(CH2)yCOO—, where y is an integer 2,3,4 and 6-24 inclusive; and
f) —(CH2CH2O)zCH2COO—, where z is an integer between 2 and 24, inclusive.

Wherein each Y represents a member independently selected from:
a) —CH2COO— (glycolic acid moiety);
b) —CH(CH3)COO— (lactic acid moiety);
g) —COCH(CH3)O— (lactic ester moiety);
h) —COCH2OCH2CH2O— (dioxanone ester moiety);
i) —COCH2CH2CH2CH2CH2O— (caprolactone ester moiety);
j) —CO(CH2)mO—, where m is an integer between 2-4 and 6-24 inclusive; and
k) —COCH2-O—(CH2CH2O)n-, where n is an integer between 2 and 24, inclusive.

Wherein each R' is hydrogen, benzyl or linear or branched alkyl group and each p is independently an integer between 1 and 4, inclusive, Z is O or NH.

Wherein Rn represents one or more members selected from H, alkoxy, benzyloxy, aldehyde, halogen, carboxylic acid and —NO2, which is attached directly or through an aliphatic chain to an aromatic ring.

The aromatic compound is selected from amine and/or carboxylic acid containing phenols, such as amino phenols, amino salicylic acids and amino benzoic acids.

In another embodiment, exemplary diisocyanates for fully or completely degradable reticulated elastomeric matrix include various hydrolytically-degradable, bridged diphenyl diisocyanates having the structures of Formulas VI-X as described in US patent application 2009/0292029.

Formula VI
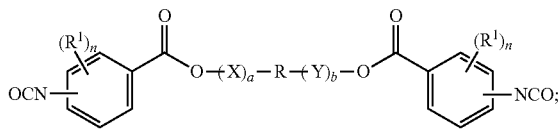

Formula VII
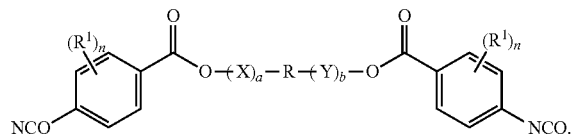

Formula VIII
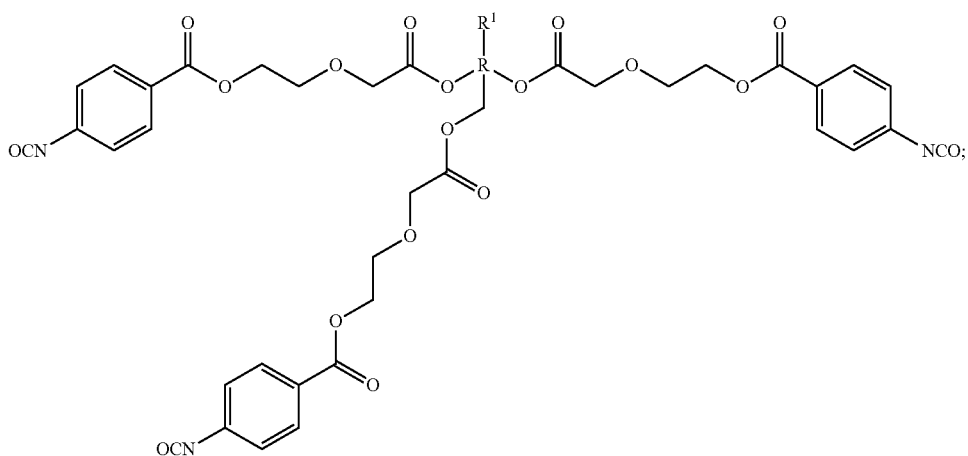

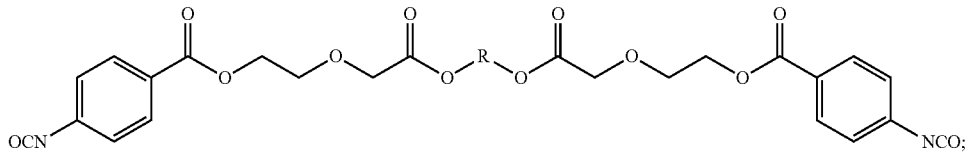

Formula IX

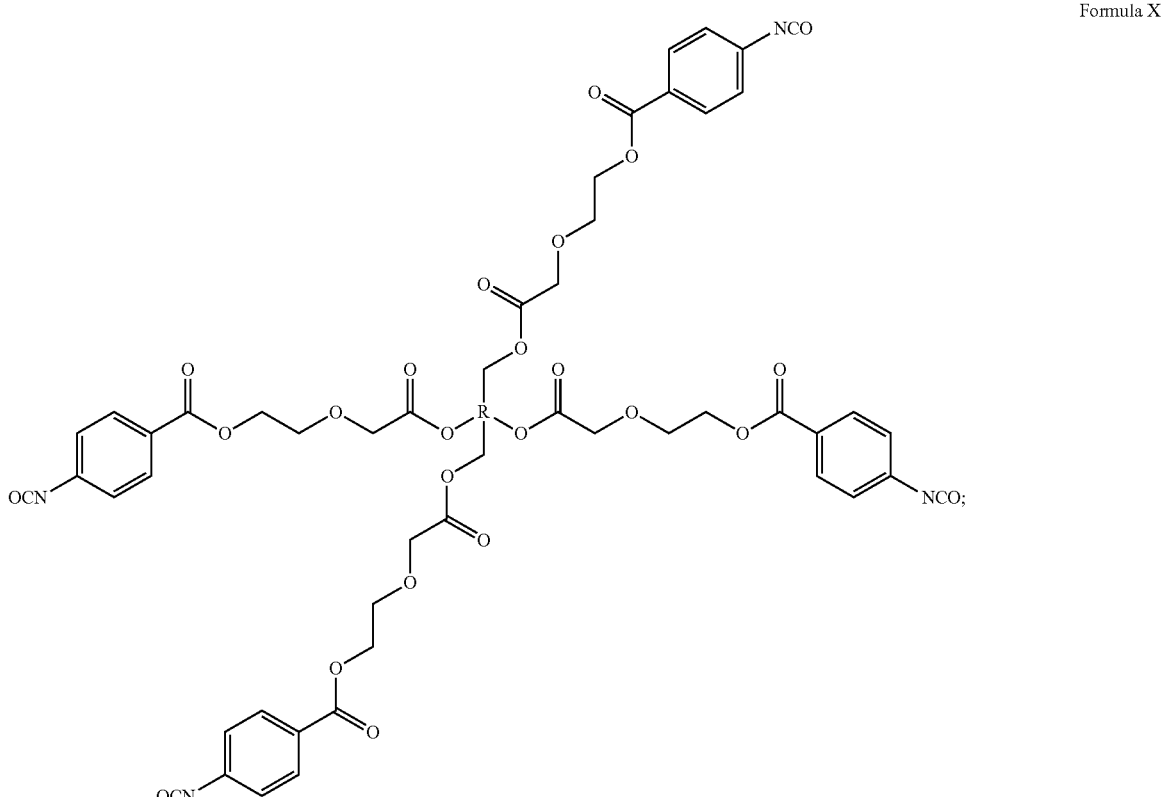

Formula X

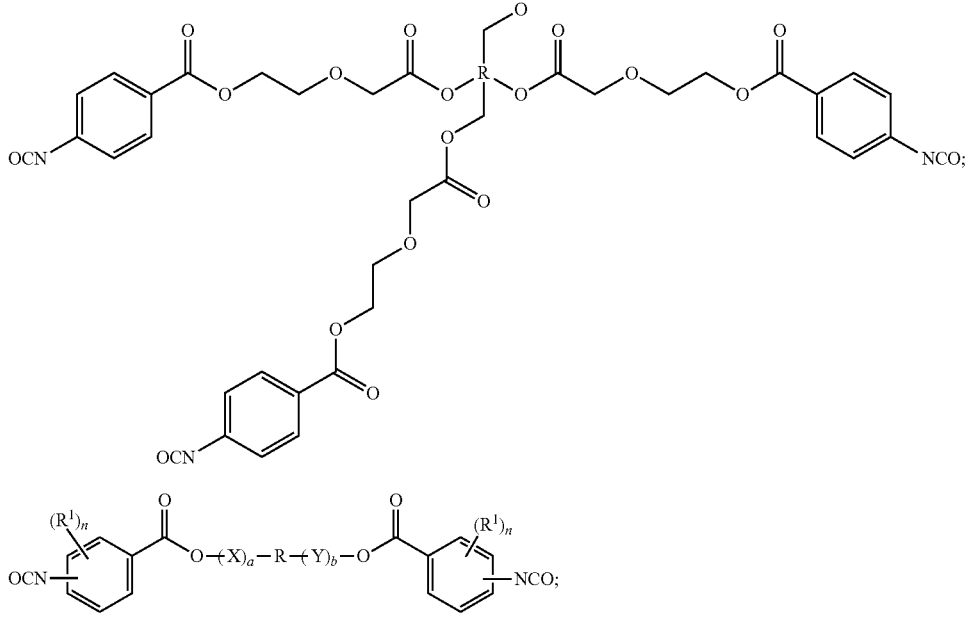

Formula XI

Exemplary chain extenders include diols, diamines, alkanol amines or a mixture thereof. In one embodiment, the chain extender is an aliphatic diol having from 2 to 10 carbon atoms (C2-C10-aliphatic diol). In another embodiment, the diol chain extender is selected from ethylene glycol, 1,2-propane diol, 1,3-propane diol, 1,4-butane diol, 1,5-pentane diol, diethylene glycol, triethylene glycol, 1,4cyclohexane dimethanol, 1,6hexane diol, or a mixture thereof.

In another embodiment, the chain extender is a diamine having from 2 to 10 carbon atoms (C2-C10-diamine). In another embodiment, the diamine chain extender is selected from ethylene diamine, 1,3-diaminobutane, 1,4-diaminobutane, 1,5diaminopentane, 1,6-diaminohexane, 1,7-diaminoheptane, 1,8-diaminooctane, isophorone diamine, or a mixture thereof.

In another embodiment, the chain extender is an alkanol amine having from 2 to 10 carbon atoms. In another embodiment, the alkanol amine chain extender is selected from diethanolamine, triethanolamine, isopropanolamine, dimethylethanolamine, methyldiethanolamine, diethylethanolamine or a mixture thereof. In another embodiment, the chain extender is butane diol, In another embodiment, the chain extender is formed by a reaction between a naturally-occurring amino acid and a diol. In one embodiment, at least partially degradable or fully degradable reticulated elastomeric matrix comprise a chain extender. In one embodiment, at least partially degradable or fully degradable reticulated elastomeric matrix comprise an optional chain extender. In one embodiment, controlled degradation characteristics of the reticulated elastomeric matrix can be obtained from degree and extent of chain extension. In another embodiment, the degradation rate of the reticulated elastomeric matrix can be obtained from degree and extent of chain extension.

In one embodiment, a small quantity of an optional ingredient, such as a multi-functional hydroxyl compound or other cross-linker having a functionality greater than 2, e.g., glycerol, is present to allow cross-linking. In one embodiment glycerol is a very effective cross-linker for the hard segment and it's incorporation in the reticulated elastomeric matrix provides a secondary source of cross-linking in addition to functionality greater than 2 for the isocyanate. In one embodiment, incorporation of the tri-functional glycerol in the reticulated elastomeric matrix provides a more controlled cross-linking to the matrix. In another embodiment, the optional multi-functional cross-linker is present in an amount just sufficient to achieve a stable foam, i.e., a foam that does not collapse to become non-foamlike. Alternatively, or in addition, polyfunctional adducts of aliphatic and cycloaliphatic isocyanates can be used to impart cross-linking in combination with aromatic diisocyanates. Alternatively, or in addition, polyfunctional adducts of aliphatic and cycloaliphatic isocyanates can be used to impart cross-linking in combination with aliphatic diisocyanates. In one embodiment, tri or multi-functional amines can be is present to allow cross-linking. In one embodiment, controlled degradation characteristics of the reticulated elastomeric matrix can be obtained from degree and extent of cross-linking. In another embodiment, the degradation rate of the reticulated elastomeric matrix can be obtained from degree and extent of cross-linking. Cross-linking to control degradation characteristics or the degradation rate of the reticulated elastomeric matrix can be obtained by a multi-functional hydroxyl compound or multi-functional amines or other cross-linker having a functionality greater than 2, Exemplary blowing agents include water and the physical blowing agents, e.g., volatile organic chemicals such as hydrocarbons, ethanol and acetone, and various fluorocarbons and their more environmentally friendly replacements, such as hydrofluorocarbons, chlorofluorocarbons and hydrochlorofluorocarbons. The reaction of water with an isocyanate group yields carbon dioxide, which serves as a blowing agent. Additionally, the reaction of water with an isocyanate group leads to the formation of urea groups. In one embodiment, the urea groups formed during the foaming reaction of isocyanate with water. In one embodiment, the amount of blowing agents such as water is used to control the density of the reticulated elastomeric matrix In one embodiment, controlled degradation characteristics of the reticulated elastomeric matrix can be obtained by the amount of urea groups. In another embodiment, the degradation rate of the reticulated elastomeric matrix can be obtained by the amount of urea groups. Moreover, combinations of blowing agents, such as water with a fluorocarbon, can be used in certain embodiments. In another embodiment, water is used as the blowing agent. Commercial fluorocarbon blowing agents are available from Huntsman, E.I. duPont de Nemours and Co. (Wilmington, Del.), Allied Chemical (Minneapolis, Minn.) and Honeywell (Morristown, N.J.).

An alternative preparation, embodiment pursuant to the invention involves partial or total replacement of water as a blowing agent with water-soluble spheres, fillers or particles which are removed, e.g., by washing, extraction or melting, after full cross-linking of the matrix.

Optionally, the process employs at least one catalyst in certain embodiments selected from a blowing catalyst, e.g., a tertiary amine, a gelling catalyst, e.g., dibutyltin dilaurate, or a mixture thereof. Moreover tertiary amine catalysts can also have gelling effects, that is, they can act as a blowing and gelling catalyst. Exemplary amine catalysts include Dabco 33LV and A-133 from Air Products. In another embodiment, a catalyst such as, e.g., the tin catalyst, is used. In another embodiment, a catalyst such as, e.g., the tin catalyst, is omitted and optionally substituted with another catalyst, e.g., a tertiary amine. In one embodiment, the tertiary amine catalyst comprises one or more non-aromatic amines. In another embodiment, the reaction is conducted so that the tertiary amine catalyst, if employed, is wholly reacted into the polymer, and residues of same are avoided. In another embodiment, the gelling catalyst is omitted and, instead, higher foaming temperatures are used. Exemplary tertiary amine catalysts include the TOTYCAT line from Toyo Soda Co. (Japan), the TEXACAT line from Texaco Chemical Co. (Austin, Tex.), the KOSMOS and TEGO lines from Th. Goldschmidt Co. (Germany), the DMP line from Rohm and Haas (Philadelphia, Pa.), the KAO LIZER line from Kao Corp. (Japan), and the QUINCAT line from Enterprise Chemical Co. (Altamonte Springs, Fla.). Exemplary organotin catalysts include the FOMREZ and FOMREZ UL lines from Witco Corporation (Middlebury, Conn.), the COCURE and COSCAT lines from Cosan Chemical Co. (Carlstadt, N.J.), and the DABCO and POLYCAT lines from Air Products.

In certain embodiments, the process employs at least one surfactant. Exemplary surfactants include TEGOSTAB BF 2370, B-8300, B-8305 and B-5055, all from Goldschmidt, DC 5241 from Dow Corning (Midland, Mich.), and other non-ionic organosilicones, such as the polydimethylsiloxane types available from Dow Corning, Air Products and General Electric (Waterford, N.Y.).

In certain embodiments, the process employs at least one cell-opener. Exemplary cell-openers include ORTEGOL 501 from Goldschmidt. Exemplary cell-openers include ORTEGOL 515 from Goldschmidt. In one embodiment, the cell opener is a suspended particle and in another embodiment, the cell opener is a, surfactant type cell opener. In another embodiment, the process employs at least viscosity modifier or viscosity depressant or compatibilizer such as Propylene carbonate.

In certain embodiments, the hard segment comprising isocyanate such as MDI of the at least partially degradable elastomeric matrix can be between 10 and 60 mole % of the elastomeric matrix. In another embodiment, hard segment comprising isocyanate such as MDI of the least partially degradable elastomeric matrix is between 25 and 45 mole % of the elastomeric matrix. In another embodiment, hard segment comprising isocyanate such as MDI of the least partially degradable elastomeric matrix is between 20 and 50 mole % of the elastomeric matrix. The hard segment comprising isocyanate such as MDI can be substantially or totally biostable or biodurable. In another embodiment, the hard segment comprising isocyanate such as MDI is partially or totally degrade or bioabsorb or bio-resorb over time. In one embodiment, the mechanism for degradation for both hard and soft segment is hydrolytic and/or enzymatic degradation.

Cross-linked polyurethanes may be prepared by approaches which include the prepolymer process and the one-shot process. An embodiment involving a prepolymer is as follows. First, the prepolymer is prepared by a conventional method from the polyol diol in diisocyanate, preferably excess diisocyanate, to produce an isocyanate terminated molecule; the pre-polymer generally has a lower molecular weight but can have an intermediate or higher molecular weight. Subsequent reaction of the pre-polymer with a diol or diamine chain extender and/or multi-functional hydroxyl compound and/or multi-functional amine compound constitutes the second step which produces a block copolymer, preferably a multi-block copolymer. The block copolymer can be cross-linked when the number of isocyanate groups per molecule in the isocyanate component is greater than 2 and/or when a multi-functional hydroxyl compound or other cross-linker having a functionality greater than 2, e.g., glycerol, is present to allow cross-linking. In another embodiment, the prepolymer is prepared from at least one isocyanate component (e.g., methylene diphenyl diisocyanate or MDI), and at least one multi-functional soft segment material with a functionality greater than 2 (e.g., a polyether-based soft segment with a functionality of 3). Then, the prepolymer, optionally at least one catalyst (e.g., dibutyltin dilaurate) and at least one difunctional chain extender (e.g., 1,4-butanediol) are admixed in a mixing vessel to cure or cross-link the mixture. In another embodiment, cross-linking takes place in a mold. In another embodiment, cross-linking and foaming, i.e., pore formation, take place together. In another embodiment, cross-linking and foaming take place together in a mold.

Alternatively, the so-called "one-shot" approach may be used. A one-shot embodiment requires no separate prepolymer-making step. In one embodiment, the starting materials, such as those described in the previous paragraphs, are admixed in a mixing vessel and then foamed and cross-linked. In one embodiment, the starting materials, such as those described in the previous paragraphs, are admixed in a mixing vessel and then foamed. In embodiment, the starting materials, such as those described in the previous paragraphs are separate or some of them are mixed before they are admixed in a mixing vessel and then foamed and cross-linked. In another embodiment, the ingredients are heated before they are admixed. In another embodiment, only selected ingredients are heated before they are admixed. In another embodiment, at least one ingredient and no more than three ingredients are heated before they are admixed. In another embodiment, the ingredients are heated as they are admixed or in other words, the mixing chamber or the foaming reactor is heated. In another embodiment, cross-linking takes place in a mold. The mold can be stationary or can be moving such as conveyor belts with walls and whose speed can be controlled. In another embodiment, foaming and cross-linking take place together. In another embodiment, cross-linking and foaming take place together in a mold. In another embodiment, foaming take place together in a mold. In another embodiment, all of the ingredients except for the isocyanate component are admixed in a mixing vessel. The isocyanate component is then added, e.g., with high-speed stirring, and cross-linking and foaming ensues. In another embodiment, all of the ingredients except for the isocyanate component are admixed in a mixing vessel; the isocyanate component is then added, e.g., with high-speed stirring, and foaming ensues. In another embodiment, this foaming mix is poured into a stationary mold and allowed to rise. In another embodiment, this foaming mix is poured into a moving mold such as conveyor belts with walls and allowed to rise.

In another embodiment, the polyol component is admixed with the isocyanate component and other optional additives, such as a viscosity modifier, surfactant and/or cell opener, to form a first liquid. The isocyanate component with functionality greater than 2 provides cross-linking. In another embodiment, the polyol component is a liquid at the mixing temperature. In another embodiment, the polyol component is a solid, therefore, the mixing temperature is raised such that the polyol component is liquefied prior to mixing, e.g., by heating. Next, a second liquid is formed by admixing a blowing agent and cross-linker with any optional additives, such as gelling catalyst and/or blowing catalyst. The blowing agent is preferably water and in embodiment is distilled water. The cross-linking agent is glycerol. Then, the first liquid and the second liquid are admixed in a mixing vessel and then foamed and cross-linked. In another embodiment, foaming and cross-linking occur simultaneously. The foaming mix is poured optionally through a nozzle into a mold and allowed to rise. In one embodiment, the process can be "one-shot" approach. In another embodiment, the process can follow the pre-polymer approach.

In another embodiment of the one-shot approach, the isocyanate component forms a first liquid. The isocyanate component with functionality greater than 2 provides cross-linking. In one embodiment, the isocyanate component is maintained between 5 psi and 30 psi above the ambient pressure and in another embodiment, the isocyanate component is optionally maintained between 20° C. to 30° C. The polyol component is admixed with other optional additives, such as a viscosity modifier, and/or cell opener, to form a second liquid. In another embodiment, the polyol component is a liquid at the mixing temperature. In another embodiment, the polyol component is a liquid at the mixing temperature or in another embodiment, the polyol component is a liquid at room temperature. In another embodiment, the polyol component is a solid, therefore, the mixing temperature is raised such that the polyol component is liquefied prior to mixing, e.g., by heating. In one embodiment, the temperature of the polyol can be between 50° C. and 90° C. In one embodiment, the polyol component is admixed or pre-mixed with cell opener and viscosity depressant. In another the polyol component is optionally admixed or pre-mixed with cell opener and viscosity depressant. Next, a third liquid is formed by admixing a blowing agent and a cross-liner and optionally a chain extender and optional additives, such as gelling catalyst and/or blowing catalyst and surfactants. The blowing agent is preferably water and in embodiment is distilled water. The cross-linking agent is preferably glycerol. In one embodiment the blowing agent, water, and cross-linking agent, glycerol, are always admixed before the foaming and cross-linking reactions. In one embodiment the blowing agent, water, and cross-linking agent, glycerol, are always admixed before the foaming. Then, the first liquid, the second liquid and the third liquid are admixed in a mixing vessel and then foamed and cross-linked. In one embodiment, the first liquid, the second liquid and the third liquid are admixed in a mixing vessel and then foamed. In another embodiment, foaming and cross-linking occur simultaneously. In another embodiment, this foaming mix is poured optionally through a nozzle into a mold and allowed to rise. Considerations must be taken to ensure that the foaming fluid or the reacting mix is laid down on to the mold bottom surface in a linear fashion or without effective retracing of the flow paths so that it does not introduce any flow disturbances or mix up of the differently aged foaming fluid or the reacting mix coming out of the mixing vessel. In one embodiment, the foaming fluid or the reacting mix is laid down on to the mold bottom surface in a linear fashion or without effective retracing of the flow paths such that the foaming fluid or the reacting mix coming out of the mixing vessel at a later time do not introduce any flow disturbances or mix with foaming fluid or the reacting mix that came out earlier.

In another embodiment of the one-shot process, the delivery system for the polyol component is placed inside a heated compartment to maintain the material as a liquid and accurately maintain temperature control. In another embodiment, the isocyanate component is maintained in a continuously stirred vessel under greater than ambient pressure, between 5 psi and 75 psi above the ambient pressure, to increase nucleation sites available during the reaction process. In another embodiment, isocyanate component is maintained in a continuously stirred vessel under greater than ambient pressure, preferably between 15 psi and 60 psi above the ambient pressure. Higher pressure helps to provide more nucleation leading to finer sized or smaller sized cells. In one extreme, vacuum can be applied to provide larger sized or coarse sized cells. Thus appropriate section of pressure is critical for controlling the cell size. In another embodiment, the reactive components along with the catalysts and surfactants are admixed and maintained in a continuously stirred vessel. In one embodiment, the reactive components include a blowing agent and a cross-liner and a chain extender. In one embodiment, the reactive components include a blowing agent and a cross-liner and a chain extender but does not include the polyol component or the isocyanate component. The blowing agent is preferably water and in one embodiment is distilled water. The cross-linking agent is glycerol. In one embodiment the blowing agent, water, and cross-linking agent, glycerol, are always admixed before the foaming and cross-linking reactions Optionally, the cell opener or any of the chemical constituents could be admixed together or maintained as an independent stream.

In each of the aforementioned embodiments, the independent systems are pumped within their respective systems and controlled with the proper flow rate within recirculation loops to maintain their correct and/or pre-determined proportions within the formulation and subsequently diverted into a mixing chamber with a high shear mixer where they are combined to react in a continuous manner. One embodiment, the high shear mixer contains a multitude of pins and/or stationary mixing elements. The rotational speed of the mixer is maintained between 500 to 10,000 rpm preferably between 5000 and 8000 rpm. Appropriate selection of the high speed mixing helps to maintain the consistency of the nucleation site by controlling the distribution of the liquid-gas interface. In another embodiment, the mixed constituents of the formulation can be injected at variable pressures through nozzles to further control the fluid dynamic properties of the materials within the reaction chamber. Higher injection pressures help to create finer atomization of the injected constituents, which can have a beneficial effect on the nucleation within the resulting porous matrix. In another embodiment, the reaction mixture is poured onto a release paper coated moving conveyor with fixed walls to create a continuous steady state mold for the foaming process. The reaction mixture or the foaming mix after being poured optionally through a nozzle into a mold and allowed to rise fill the volume of the mold and are guided within the space by the walls of the mold. Considerations must be taken to ensure that the foaming fluid or the reacting mix is laid down on to the mold bottom surface in a linear fashion or without effective retracing of the flow paths so that it does not introduce any flow disturbances or mix up of the differently aged foaming fluid or the reacting mix coming out of the mixing vessel. In one embodiment, the foaming fluid or the reacting mix is laid down on to the mold bottom surface in a linear fashion or without effective retracing of the flow paths such that the foaming fluid or the reacting mix coming out of the mixing vessel at a later time do not introduce any flow disturbances or mix with foaming fluid or the reacting mix that came out earlier.

At the end of the foam rise, the foaming and cross-linking reaction are considered to be complete or substantially complete and leads to the formation of a foamed block or a foamed matrix. In one embodiment, the foamed block or the foamed matrix has undergone gelation to provide a matrix with dimensional and structural stability. In one embodiment, the composition of the ingredients that comprise the foamed block or the foamed matrix has undergone gelation to provide a matrix with dimensional and structural stability. Dimensional and structural stability are required to withstand the high pressure and temperature generated during reticulation. An incomplete gelation may lead to inefficient reticulation. Dimensional and structural stability are required to provide a consistent cell and pores throughout the foamed block or the foamed matrix. In one embodiment, the foamed block or the foamed matrix comprises ruptured or broken windows or membranes. In one embodiment, the foamed block or the foamed matrix comprises ruptured or broken windows or membranes that will allow for passage of reticulation gas mixture. In one embodiment, the composition of the ingredients that comprise the foamed block or the foamed matrix comprises ruptured or broken windows or membranes. In one embodiment, the composition of the ingredients that comprise the foamed block or the foamed matrix comprises ruptured or broken windows or membranes that will allow for passage of reticulation gas mixture. If these ruptured or broken windows or membranes did not exist then the foamed block or the foamed matrix will be considered having closed cell porous structure or closed cell structure and cannot be reticulated as there are not adequate passage ways for the combustion gas to pass in order to rupture or melt the windows or membranes between the struts and create a reticulated matrix with inter-connected and inter-communicating cells and pores.

Gelation characteristics of polycaprolactone polyols are different than gelation characteristics of caprolactone copolymer polyols with glycolide, lactide, d/l lactide and polyparadioxanone. In one embodiment, the polycaprolactone copolymer polyols takes longer to solidify compared to linear polycaprolactone polyols. In one embodiment, the polycaprolactone copolymer polyols with glycolide, lactide, d/l lactide and polyparadioxanone takes longer to solidify compared to linear polycaprolactone polyols. In one embodiment, the polycaprolactone copolymer polyols reacts slowly in the polymerization reactions compared to linear polycaprolactone polyols. In one embodiment, the polycaprolactone copolymer polyols with glycolide, lactide, d/l lactide and polyparadioxanone reacts slowly in the polymerization reactions compared to linear polycaprolactone polyols. In one embodiment, isocyanate with functionality of 2 reacts slowly in the polymerization reactions compared to isocyanate with functionality greater than 2. In one embodiment, aliphatic isocyanate reacts slowly in the polymerization reactions compared to aromatic isocyanate. In one embodiment, aromatic isocyanate leads to faster gelation compared to aliphatic isocyanate. In another embodiment, isocyanate with functionality of 2 reacts slowly in the polymerization reactions compared to isocyanate with functionality greater than 2. In another embodiment, the process comprises a gelation process that provides dimensional and structural stability of the foam matrix. In another embodiment, the process comprises a gelation process that provides dimensional and structural stability of the foam matrix even in cases where the polymerization reaction rates are slow owing to a slow reactivity of polyol or isocyanate.

At the end of the foam rise, the foaming and cross-linking reaction are considered to be complete or substantially complete and leads to the formation of a foamed block or a foamed matrix. In one embodiment, the foamed matrix is then optionally subjected to additional curing at an elevated temperature. The curing ensures the utilization and/or removal of any free isocyanates and amines and/or completion or substantial completion of other un-reacted ingredients that may not have reacted during foam formation. The curing temperature can range from 70° C. to 120° C. and in other embodiment can range from 75° C. to 110° C. The curing time can range from 30 minutes to 400 minutes and in other embodiment can range from 60 minutes to 300 minutes. In one embodiment, the foamed matrix is not subjected to additional curing at an elevated temperature.

In another embodiment, any or all of the processing approaches of the invention may be used to make foam with a density greater than 1.0 lbs/ft$^3$ (0.016 g/cc). In this embodiment, cross-linker(s), such as glycerol, are used; the functionality of the isocyanate component is from 2.0 to 2.4; the isocyanate component in case of least partially degradable matrix formulation consists essentially of MDI; and the amount of 4,4'-MDI is greater than about 50% by weight of the isocyanate component. The molecular weight of the polyol component is from about 500 to about 5,000 Daltons preferably between 1000 and 3500. The amount of blowing agent, e.g., water, is adjusted to obtain non-reticulated foam densities with lower amount of water leading to higher densities. A reduced amount of blowing agent may reduce the number of urea linkages in the material. Any reduction in stiffness and/or tensile strength and/or compressive strength caused by fewer urea linkages can be compensated for by using di-functional chain extenders, such as butanediol, and/or increasing the density of the foam, and/or by increasing the amount of cross-linking agent used and/or by increasing the stereo regularity of the isocyanate component. In one embodiment, reducing the degree of cross-linking and, consequently, increasing the foam's toughness and/or elongation to break should allow for more efficient reticulation by improving its ability to withstand the sudden impact of one or a plurality of reticulation steps. However if the reduction is cross-linking is too low or below a certain level, the mechanical performances can become lower and the material can breakdown during handling or during reticulation. In another embodiment, the molecular weight of the polyol can determine the flexibility and/or the toughness and/or elongation to break. In one embodiment, higher molecular of polyol can lead to increasing the foam's toughness and/or elongation to break and allow for more efficient reticulation by improving its ability to withstand the sudden impact of one or a plurality of reticulation steps. In another embodiment, the higher density foam material which results can better withstand the sudden impact of one or a plurality of reticulation steps, e.g., two reticulation steps, and can provide for minimal, if any, damage to struts 16.

In one embodiment, the invention provides a process for preparing a flexible polyurethane least partially degradable or fully degradable matrix capable of being reticulated based on polycaprolactone polyol component or polyol component containing copolymers of polycaprolactone and isocyanate component starting materials. In another embodiment, a porous least partially degradable or fully degradable elastomer polymerization process for making a resilient polyurethane matrix is provided which process comprises admixing a polycaprolactone polyol component and an aliphatic isocyanate component, for example $H_u$ MDI. In another embodiment, a porous least partially degradable or fully degradable elastomer polymerization process for making a resilient polyurethane matrix is provided which process comprises admixing a polycaprolactone polyol component and an aliphatic isocyanate component, for example, lysine methyl ester diisocyanate. In another embodiment, a porous least partially degradable or fully degradable elastomer polymerization process for making a resilient polyurethane matrix is provided which process comprises admixing a polycaprolactone polyol component and various degradable diisocyanate described in US patent application 2006/0188547 A1 and US patent application 2009/0292029 and are referenced as hydrolytically-degradable bridged diphenyl diisocyanates and comprise multiple groups of polymers selected from a group one (containing glycolic acid moiety, lactic acid moiety, dioxanone and caprolactone moiety), group two (containing glycolic ester moiety, lactic ester moiety, dioxanone ester moiety, group three (containing hydrogen, benzyl or an alkyl group, the alkyl group being either straight-chained or branched) and group four (selected from H, alkoxy, benzyloxy, aldehyde, halogen, carboxylic acid and —$NO_2$, which is attached directly to an aromatic ring or attached through an aliphatic chain)

In another embodiment, the foam is substantially free of isocyanurate linkages. In another embodiment, the foam has no isocyanurate linkages. In another embodiment, the foam is substantially free of biuret linkages. In another embodiment, the foam has no biuret linkages. In another embodiment, the foam is substantially free of allophanate linkages. In another embodiment, the foam has no allophanate linkages. In another embodiment, the foam is substantially free of isocyanurate and biuret linkages. In another embodiment, the foam has no isocyanurate and biuret linkages. In another embodiment, the foam is substantially free of isocyanurate and allophanate linkages. In another embodiment, the foam has no isocyanurate and allophanate linkages. In another embodiment, the foam is substantially free of allophanate and biuret linkages. In another embodiment, the foam has no allophanate and biuret linkages. In another embodiment, the foam is substantially free of allophanate, biuret and isocyanurate linkages. In another embodiment, the foam has no allophanate, biuret and isocyanurate linkages. Without being bound by any particular theory, it is thought that the absence of allophanate, biuret and/or isocyanurate linkages provides an enhanced degree of flexibility to the elastomeric matrix because of lower cross-linking of the hard segments.

In certain embodiments, additives helpful in achieving a stable foam, for example, surfactants and catalysts, can be included. By limiting the quantities of such additives to the minimum desirable while maintaining the functionality of each additive, the impact on the toxicity of the product can be controlled.

In one embodiment, elastomeric matrices of various densities, e.g., from about 0.008 to about 0.15 g/cc (from about 0.50 to about 9.4 lb/ft$^3$) are produced. In another embodiment, elastomeric matrices of various densities, e.g., from about 0.008 g/cc to about 0.320 g/cc (from about 0.5 lb/ft$^3$ to about 20 lb/ft$^3$) are produced. The density is controlled by, e.g., the amount of blowing or foaming agent, the isocyanate index, the isocyanate component content in the formulation, the reaction exotherm, and/or the pressure of the foaming environment.

For the purpose of embodiments of the invention, for every 100 parts by weight (or 100 grams) of polyol component (e.g., polycaprolactone polyol, polyol, poly (caprolactone-co-l-lactide) polyol, poly(caprolactone-co-glycolide)polyol, polyol or poly (caprolactone-co-d/l-lactide)) that can be used to make an elastomeric matrix through foaming and cross-linking, the amounts of the other components present, by weight, in a formulation are as follows: from about 10 to about 90 parts (or grams) isocyanate component (e.g., MDIs, their mixtures, $H_{12}$MDI, lysine methyl ester diisocyanate, degradable diisocyanate described in US patent application 2006/0188547 A1) with an isocyanate index of from about 0.85 to about 1.05 preferably from about 0.90 to about 1.02, from about 0.5 to about 6.0 parts (or grams) blowing agent (e.g., water), from about 0.1 to about 2.0 parts (or grams) blowing catalyst (e.g., tertiary amine), from about 0.1 to about 8.0 parts (or grams) surfactant, and from about 0.1 to about 8.0 parts (or grams) cell opener. The amount of isocyanate component is related to and depends upon the magnitude of the isocyanate index for a particular formulation. Additionally, for every 100 parts by weight (or 100 grams) of polyol component that can be used to make an elastomeric matrix through foaming and cross-linking, the amounts of the following optional components, when present in a formulation, are as follows by weight: up to about 20 parts (or grams)

chain extender, up to about 20 parts (or grams) cross-linker, up to about 0.5 parts (or grams) gelling catalyst (e.g., a compound comprising tin), up to about 10.0 parts (or grams) physical blowing agent (e.g., hydrocarbons, ethanol, acetone, fluorocarbons), and optionally up to about 15 parts (or grams) viscosity modifier. The isocyanate is maintained between 15 and 60 psi and optionally between 20 and 55 psi. The mixing speed is between 5000 and 8000 rpm. The foaming fluid or the reacting mix is laid down on to the mold bottom surface in a linear fashion or without effective retracing of the flow paths.

For the purpose of embodiments of the invention, for every 100 parts by weight (or 100 grams) of polyol component (e.g., polycaprolactone polyol, polyol, poly (caprolactone-co-l-lactide) polyol, poly(caprolactone-co-glycolide)polyol, polyol or poly (caprolactone-co-d/l-lactide)) that can be used to make an elastomeric matrix through foaming and cross-linking, the amounts of the other components present, by weight, in a formulation are as follows: from about 30 to about 70 parts (or grams) isocyanate component (e.g., MDIs, their mixtures, $H_{12}$MDI, lysine methyl ester diisocyanate, degradable diisocyanate described in US patent application 2006/0188547 A1) with an isocyanate index of from about 0.85 to about 1.05 preferably from about 0.90 to about 1.02, from about 1.0 to about 5.0 parts (or grams) blowing agent (e.g., water), from about 0.5 to about 2.5 parts (or grams) blowing catalyst (e.g., tertiary amine), from about 0.5 to about 5.0 parts (or grams) surfactant, and from about 0.1 to about 5.0 parts (or grams) cell opener. The amount of isocyanate component is related to and depends upon the magnitude of the isocyanate index for a particular formulation. Additionally, for every 100 parts by weight (or 100 grams) of polyol component that can be used to make an elastomeric matrix through foaming and cross-linking, the amounts of the following optional components, when present in a formulation, are as follows by weight: up to about 10 parts (or grams) chain extender, up to about 10 parts (or grams) cross-linker, up to about 1.5 parts (or grams) gelling catalyst (e.g., a compound comprising tin), up to about 15.0 parts (or grams) physical blowing agent (e.g., hydrocarbons, ethanol, acetone, fluorocarbons), and optionally up to about 20 parts (or grams) viscosity modifier. The isocyanate is maintained between 15 and 60 psi and optionally between 20 and 55 psi and optionally under vacuum. The mixing speed is between 5000 and 8000 rpm and optionally between 2000 and 8000 rpm. The foaming fluid or the reacting mix is laid down on to the mold bottom surface in a linear fashion or without effective retracing of the flow paths.

In other embodiments, for every 100 parts by weight (or 100 grams) of polyol component (e.g., polycaprolactone polyol, polyol, poly (caprolactone-co-l-lactide)polyol, poly (caprolactone-co-glycolide)polyol or poly (caprolactone-co-d/l-lactide)) that can be used to make an elastomeric matrix through foaming and cross-linking, the amounts of the other components present, by weight, in a formulation are as follows: from about 10 to about 90 parts (or grams) isocyanate component (e.g., MDIs, their mixtures, $H_{12}$MDI, lysine methyl ester diisocyanate, degradable diisocyanate described in US patent application 2006/0188547 A1 and US patent application 2009/0292029) with an isocyanate index of from about from about 0.85 to about 1.019 in another embodiment, from about 0.5 to about 6.0 parts (or grams) blowing agent (e.g., water), optionally, from about 0.05 to about 3.0 parts (or grams) catalyst (e.g., tertiary amine), such as a blowing catalyst and/or gelling catalyst, from about 0.1 to about 8.0 parts (or grams) surfactant, optionally, from about 0.1 to about 8.0 parts (or grams) cell opener, optionally, from about 0.05 to about 8.0 parts (or grams) cross-linking agent, e.g., glycerine, and optionally, from about 0.05 to about 8.0 parts (or grams) chain extender, e.g., 1,4-butanediol. The isocyanate is maintained between 15 and 60 psi and optionally between 20 and 55 psi. The mixing speed is between 5000 and 8000 rpm. The foaming fluid or the reacting mix is laid down on to the mold bottom surface in a linear fashion or without effective retracing of the flow paths.

Matrices with appropriate properties for the purposes of embodiments of the invention, as determined by testing, for example, acceptable compression set at human body temperature, airflow, tensile strength and compressive properties, can then be reticulated.

The matrix that are made by polymerization, cross-linking and foaming form cells and pores forms a porous matrix that still needs to undergo further processing during reticulation. The membranes or the cell walls can be formed during the synthesis of the scaffold material or matrix by polymerization, cross-linking and foaming that can result in the formation of cells and cell walls. In one embodiment, the reticulation process substantially or fully removes at least a portion of the cell walls or membranes from the cells and pores. In another embodiment, the reticulation process substantially or fully removes the cell walls and membranes from the cells and pores.

Not all porous foams irrespective of their composition or structure can be reticulated without causing damage to their struts or having the ability to at least partially, substantially or totally remove the cell walls or membranes or windows. There are several factors that provide effective and efficient reticulation to remove or substantially remove the cell walls or membranes or windows formed during the foaming process comprising by polymerization, cross-linking and foaming. One such factor is the reduction of the degree of crosslinking and consequently increasing the foam's toughness and/or elongation to break thus allowing for more efficient and/or effective reticulation. This is because the resulting structures, with higher toughness and/or elongation to break, can have the ability, to withstand the sudden impact in a reticulation process with minimal, if any, damage to struts that surround the cells and the pores. But too low cross-linking can lead to less resilience, less pronounced elastomeric behavior and lower tensile and compression properties. As discussed earlier, one way to lower the degree of crosslinking is by keeping the matrix substantially or totally free of allophanate, biuret and isocyanurate linkages. In another embodiment, a more flexible matrix can withstand the sudden impact in a reticulation process with minimal, if any, damage to struts that form the cells and pores. One way to increase the flexibility of the matrix is to select an appropriate molecular weight for the polyol and without being bound by any particular theory, a higher molecular weight of polyol leads to more flexible matrix. Also for the reticulation process to be efficient and effective, there must be adequate passage for gaseous exchange during evacuation of air from the foamed matrix and during the saturation of combustible gases before ignition. In one embodiment, the composition of the ingredients that comprise the foamed block or the foamed matrix comprises ruptured or broken windows or membranes that will allow for passage of reticulation gas mixture. If these ruptured or broken windows or membranes did not exist then the foamed block or the foamed matrix will be considered having closed cell porous structure or closed cell structure and cannot be reticulated. There are other important variables that need to be controlled such as void content, cell size, cell distribution, mechanical strength and modulus, etc. in the pre-reticulated matrix for the reticulation to be efficient in creating the interconnected and inter-communicating network of cells and pores. It is thus evident that there needs to be a balance between the structure and properties of the matrix before reticulation for the reticulation process to be efficient in creating accessible inter-connected and inter-communicating pores and cells. Thus, the designing the appropriate chemical composition, formulation of various ingredients, and structure of the matrix with a right balance is extremely important for creation of the matrix that can be used effectively for efficient reticulation. The selection and design of the appropriate chemical composition, formulation of various ingredients, and structure of the matrix to obtain effective and efficient reticulation are novel, non-obvious and non-trivial when compared to normal foaming processes. In one embodiment, the selection and design of the appropriate chemical composition, formulation of various ingredients, and structure of the matrix to obtain effective and efficient reticulation are novel, non-obvious and non-trivial when compared to normal foaming processes with similar void content, range of pore size, and even some similarity in some of the starting ingredients. In another embodiment, to enhance biocompatibility, ingredients for the polymerization process are selected so as to avoid or minimize the presence in the end product elastomeric matrix of biologically adverse substances or substances susceptible to biological attack.

Reticulation of Elastomeric Matrices

Elastomeric matrix 10 can be subjected to any of a variety of post-processing treatments to enhance its utility, some of which are described herein and others. In one embodiment, reticulation of an elastomeric matrix 10 of the invention, if not already a part of the described production process, may be used to remove at least a portion of any existing interior "windows", i.e., the residual membranes or cell walls 22 illustrated in FIG. 1. Reticulation tends to increase fluid permeability.

Porous or foam materials with some ruptured cell walls are generally known as "open-cell" materials or foams. In contrast, porous materials known as "reticulated" or "at least partially reticulated" have many, i.e., at least about 40%, of the cell walls that would be present in an identical porous material except composed exclusively of cells that are closed, at least partially removed. Where the cell walls are least partially removed by reticulation, adjacent reticulated cells open into, interconnect with, and communicate with each other. Porous materials from which more, i.e., at least about 65%, of the cell walls have been removed are known as "further reticulated". If most, i.e., at least about 80%, or substantially all, i.e., at least about 90%, of the cell walls have been removed then the porous material that remains is known as "substantially reticulated" or "fully reticulated", respectfully. It will be understood that, pursuant to this art usage, a reticulated material or foam comprises a network of at least partially open interconnected cells.

"Reticulation" generally refers to a process for at least partially removing cell walls, not merely rupturing or tearing them by a crushing process. Moreover, crushing undesirable and creates debris that must be removed by further processing. In another embodiment, the reticulation process substantially fully removes at least a portion of the cell walls. Reticulation may be effected, for example, by at least partially dissolving away cell walls, known variously as "solvent reticulation" or "chemical reticulation"; or by at least partially melting, burning and/or exploding out cell walls, known variously as "combustion reticulation", "thermal reticulation" or "percussive reticulation". Melted material arising from melted cell walls can be deposited on the struts. In one embodiment, such a procedure may be employed in the processes of the invention to reticulate elastomeric matrix 10. In another embodiment, all entrapped air in the pores of elastomeric matrix 10 is evacuated by application of vacuum prior to reticulation. In another embodiment, reticulation is accomplished through a plurality of reticulation steps. In another embodiment, two reticulation steps are used. In another embodiment, a first combustion reticulation is followed by a second combustion reticulation. In another embodiment, combustion reticulation is followed by chemical reticulation. In another embodiment, chemical reticulation is followed by combustion reticulation. In another embodiment, a first chemical reticulation is followed by a second chemical reticulation.

In one embodiment relating to orthopedic applications and the like, the elastomeric matrix 10 can be reticulated to provide an interconnected pore structure, the pores having an average diameter or other largest transverse dimension of at least about 10 µm. In another embodiment, the elastomeric matrix can be reticulated to provide pores with an average diameter or other largest transverse dimension of at least about 20 µm. In another embodiment, the elastomeric matrix can be reticulated to provide pores with an average diameter or other largest transverse dimension of at least about 50 µm. In another embodiment, the elastomeric matrix can be reticulated to provide pores with an average diameter or other largest transverse dimension of at least about 150 µm. In another embodiment, the elastomeric matrix can be reticulated to provide pores with an average diameter or other largest transverse dimension of at least about 250 µm. In another embodiment, the elastomeric matrix can be reticulated to provide pores with an average diameter or other largest transverse dimension of greater than about 250 µm. In another embodiment, the elastomeric matrix can be reticulated to provide pores with an average diameter or other largest transverse dimension of greater than 250 µm. In another embodiment, the elastomeric matrix can be reticulated to provide pores with an average diameter or other largest transverse dimension of at least about 450 µm. In another embodiment, the elastomeric matrix can be reticulated to provide pores with an average diameter or other largest transverse dimension of greater than about 450 µm. In another embodiment, the elastomeric matrix can be reticulated to provide pores with an average diameter or other largest transverse dimension of greater than 450 µm. In another embodiment, the elastomeric matrix can be reticulated to provide pores with an average diameter or other largest transverse dimension of at least about 500 µm. In another embodiment, the elastomeric matrix can be reticulated to provide pores with an average diameter or other largest transverse dimension of at least about 800 µm. In another embodiment, the elastomeric matrix can be reticulated to provide pores with an average diameter or other largest transverse dimension of at least about 1000 µm.

In another embodiment relating to orthopedic applications and the like, the elastomeric matrix can be reticulated to provide pores with an average diameter or other largest transverse dimension of not greater than about 600 µm. In another embodiment, the elastomeric matrix can be reticulated to provide pores with an average diameter or other largest transverse dimension of not greater than about 450 µm. In another embodiment, the elastomeric matrix can be reticulated to provide pores with an average diameter or other largest transverse dimension of not greater than about 250 µm. In another embodiment, the elastomeric matrix can be reticulated to provide pores with an average diameter or other largest transverse dimension of not greater than about 150 µm. In another embodiment, the elastomeric matrix can be reticulated to provide pores with an average diameter or other largest transverse dimension of not greater than about 20 μm.

In another embodiment relating to orthopedic applications and the like, the elastomeric matrix can be reticulated to provide pores with an average diameter or other largest transverse dimension of from about 10 μm to about 50 μm. In another embodiment, the elastomeric matrix can be reticulated to provide pores with an average diameter or other largest transverse dimension of from about 20 μm to about 150 μm. In another embodiment, the elastomeric matrix can be reticulated to provide pores with an average diameter or other largest transverse dimension of from about 150 μm to about 250 μm. In another embodiment, the elastomeric matrix can be reticulated to provide pores with an average diameter or other largest transverse dimension of from about 250 μm to about 500 μm. In another embodiment, the elastomeric matrix can be reticulated to provide pores with an average diameter or other largest transverse dimension of from about 450 μm to about 600 μm. In another embodiment, the elastomeric matrix can be reticulated to provide pores with an average diameter or other largest transverse dimension of from about 10 μm to about 500 μm. In another embodiment, the elastomeric matrix can be reticulated to provide pores with an average diameter or other largest transverse dimension of from about 10 μm to about 600 μm. In another embodiment, the elastomeric matrix can be reticulated to provide pores with an average diameter or other largest transverse dimension of from about 50 μm to about 1000 μm.

Optionally, the reticulated elastomeric matrix may be purified, for example, by solvent extraction, either before or after reticulation. Any such solvent extraction, such as with isopropyl alcohol, or other purification process is, in one embodiment, a relatively mild process which is conducted so as to avoid or minimize possible adverse impact on the mechanical or physical properties of the elastomeric matrix that may be necessary to fulfill the objectives of this invention.

One embodiment employs chemical reticulation, where the elastomeric matrix is reticulated in an acid bath comprising an inorganic acid. Another embodiment employs chemical reticulation, where the elastomeric matrix is reticulated in a caustic bath comprising an inorganic base. Another embodiment employs solvent reticulation, where a volatile solvent that leaves no residue is used in the process. Another embodiment employs solvent reticulation at a temperature elevated above 25° C. In another embodiment, an elastomeric matrix comprising polycaprolactone polyurethane is solvent reticulated with a solvent selected from tetrahydrofuran ("THF"), dimethyl acetamide ("DMAC"), dimethyl sulfoxide ("DMSO"), dimethylformamide ("DMF"), N-methyl-2-pyrrolidone, also known as m-pyrol, or a mixture thereof. In another embodiment, an elastomeric matrix comprising polycaprolactone polyurethane is solvent reticulated with THF. In another embodiment, an elastomeric matrix comprising polycaprolactone polyurethane is solvent reticulated with N-methyl-2-pyrrolidone. In another embodiment, an elastomeric matrix comprising polycaprolactone polyurethane is chemically reticulated with a strong base. In another embodiment, the pH of the strong base is at least about 9.

In any of these chemical or solvent reticulation embodiments, the reticulated foam can optionally be washed. In any of these chemical or solvent reticulation embodiments, the reticulated foam can optionally be dried.

In one embodiment, combustion reticulation may be employed in which a combustible atmosphere, e.g., a mixture of hydrogen and oxygen or methane and oxygen, is ignited, e.g., by a spark. In another embodiment, combustion reticulation is conducted in a pressure chamber. In another embodiment, the pressure in the pressure chamber is substantially reduced, e.g., to below about 50-150 millitorr by evacuation for at least about 2 minutes, before, e.g., hydrogen, oxygen or a mixture thereof, is introduced. In another embodiment, the pressure in the pressure chamber is substantially reduced in more than one cycle, e.g., the pressure is substantially reduced, an unreactive gas such as argon or nitrogen is introduced then the pressure is again substantially reduced, before hydrogen, oxygen or a mixture thereof is introduced. The temperature at which reticulation occurs can be influenced by, e.g., the temperature at which the chamber is maintained and/or by the hydrogen/oxygen ratio in the chamber. In another embodiment, combustion reticulation is followed by an annealing period. In any of these combustion reticulation embodiments, the reticulated foam can optionally be washed. In any of these combustion reticulation embodiments, the reticulated foam can optionally be dried.

In one embodiment, the reticulated elastomeric matrix's permeability to a fluid, e.g., a liquid, is greater than the permeability to the fluid of an unreticulated matrix from which the reticulated elastomeric matrix was made. In another embodiment, the reticulation process is conducted to provide an elastomeric matrix configuration favoring cellular ingrowth and proliferation into the interior of the matrix. In another embodiment, the reticulation process is conducted to provide an elastomeric matrix configuration which favors cellular ingrowth and proliferation throughout the elastomeric matrix configured for implantation, as described herein. The permeability or Darcy permeability as measured by a Permeameter (made by PMI, Ithaca, N.Y.) of the foamed elastomeric matrix prior to reticulation is below 10 and in most cases below 5. Subjecting the foamed elastomeric matrix prior to reticulation to crushing (where the matrix is compressed multiple times (greater than 5 or grater than 10) at compression greater than 50% or in cases above 75%) does not change the permeability or Darcy permeability from that of the foamed elastomeric matrix prior to reticulation. The permeability or Darcy permeability is at least above 100 in one embodiment of the present invention. In another embodiment, permeability or Darcy permeability is at least above 400. In another the permeability or Darcy permeability is at least above 600.

The term "configure" and the like is used to denote the arranging, shaping and dimensioning of the respective structure to which the term is applied. Thus, reference to a structure as being "configured" for a purpose is intended to reference the whole spatial geometry of the relevant structure or part of a structure as being selected or designed to serve the stated purpose.

In any of these chemical or solvent reticulation embodiments, the reticulated foam can optionally be washed. In any of these chemical or solvent reticulation embodiments, the reticulated foam can optionally be dried.

In one embodiment, combustion reticulation may be employed in which a combustible atmosphere, e.g., a mixture of hydrogen and oxygen or methane and oxygen, is ignited, e.g., by a spark. In another embodiment, combustion reticulation is conducted in a pressure chamber. In another embodiment, the pressure in the pressure chamber is substantially reduced, e.g., to below about 50-150 millitorr by evacuation for at least about 2 minutes, before, e.g., hydrogen, oxygen or a mixture thereof, is introduced. In another embodiment, the pressure in the pressure chamber is substantially reduced in more than one cycle, e.g., the pressure is substantially reduced, an unreactive gas such as argon or nitrogen is introduced then the pressure is again substantially reduced, before hydrogen, oxygen or a mixture thereof is introduced. The temperature at which reticulation occurs can be influenced by, e.g., the temperature at which the chamber is maintained and/or by the hydrogen/oxygen ratio in the chamber. In another embodiment, combustion reticulation is followed by an annealing period. In any of these combustion reticulation embodiments, the reticulated foam can optionally be washed. In any of these combustion reticulation embodiments, the reticulated foam can optionally be dried.

In one embodiment, the reticulated elastomeric matrix's permeability to a fluid, e.g., a liquid, is greater than the permeability to the fluid of an unreticulated matrix from which the reticulated elastomeric matrix was made. In another embodiment, the reticulation process is conducted to provide an elastomeric matrix configuration favoring cellular ingrowth and proliferation into the interior of the matrix. In another embodiment, the reticulation process is conducted to provide an elastomeric matrix configuration which favors cellular ingrowth and proliferation throughout the elastomeric matrix configured for implantation, as described herein. The permeability or Darcy permeability as measured by a Permeameter (made by PMI, Ithaca, N.Y.) of the foamed elastomeric matrix prior to reticulation is below 10 and in most cases below 5. Subjecting the foamed elastomeric matrix prior to reticulation to crushing (where the matrix is compressed multiple times (greater than 5 or grater than 10) at compression greater than 50% or in cases above 75%) does not change the permeability or Darcy permeability from that of the foamed elastomeric matrix prior to reticulation. The permeability or Darcy permeability is at least above 200 in one embodiment of the present invention. In another embodiment, permeability or Darcy permeability is at least above 400. In another the permeability or Darcy permeability is at least above 600.

The term "configure" and the like is used to denote the arranging, shaping and dimensioning of the respective structure to which the term is applied. Thus, reference to a structure as being "configured" for a purpose is intended to reference the whole spatial geometry of the relevant structure or part of a structure as being selected or designed to serve the stated purpose.

At least partially degradable or fully degradable elastomeric matrix can be sterilized using either gamma or ethylene oxide. In one embodiment, the gamma sterilization can range from 20 to 50 kGy and in another embodiment can range from 20 to 40 kGy. In one embodiment, gamma sterilization can be used to obtain controlled degradation characteristics of the reticulated elastomeric matrix. In another embodiment, gamma sterilization can be used to control the degradation rates of the reticulated elastomeric matrix. In one embodiment, higher is the relative mole % of polycaprolactone in the copolymer polyol, less is the effect of gamma sterilization in controlling degradation characteristics of the reticulated elastomeric matrix.

Imparting Endopore Features

Within pores 20, elastomeric matrix 10 may, optionally, have features in addition to the void or gas-filled volume described above. In one embodiment, elastomeric matrix 10 may have what are referred to herein as "endopore" features as part of its microstructure, i.e., features of elastomeric matrix 10 that are located "within the pores". In one embodiment, the internal surfaces of pores 20 may be "endoporously coated", i.e., coated or treated to impart to those surfaces a degree of a desired characteristic.

Furthermore, one or more coatings may be applied endoporously by contacting with a film-forming biocompatible polymer either in a liquid coating solution or in a melt state under conditions suitable to allow the formation of a biocompatible polymer film. In one embodiment, the polymers that can be used for such coatings are film-forming biocompatible polymers with sufficiently high molecular weight so as not to be waxy or tacky. The polymers should also adhere to the solid phase 12. In another embodiment, the bonding strength is such that the polymer film does not crack or dislodge during handling or deployment of reticulated elastomeric matrix 10.

Suitable biocompatible polymers include polyamides, polyolefins, nonabsorbable polyesters, and preferably bioabsorbable aliphatic polyesters (e.g., homopolymers and copolymers of lactic acid, glycolic acid, lactide, glycolide, para-dioxanone, trimethylene carbonate, $\epsilon$-caprolactone or a mixture thereof). Further, biocompatible polymers include film-forming bioabsorbable polymers; these include aliphatic bioabsorbable polyesters, poly(amino acids), copoly(ether-esters), polyalkylenes oxalates, polyamides, poly(iminocarbonates), polyorthoesters, polyoxaesters including polyoxaesters containing amido groups, polyamidoesters, polyanhydrides, polyphosphazenes, biomolecules or a mixture thereof. For the purpose of embodiments of this invention bioabsorbable aliphatic polyesters include polymers and copolymers of lactide (which includes lactic acid d-, l- and meso lactide), $\epsilon$-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one or a mixture thereof. In one embodiment, the reinforcement can be made from biopolymer, such as collagen, elastin, and the like. The biopolymer can be biodegradable or bioabsorbable.

Biocompatible polymers further include film-forming biodurable polymers with relatively low chronic tissue response, such as polyurethanes, silicones, poly(meth)acrylates, polyesters, polyalkyl oxides (e.g., polyethylene oxide), polyvinyl alcohols, polyethylene glycols and polyvinyl pyrrolidone, as well as hydrogels, such as those formed from cross-linked polyvinyl pyrrolidinone and polyesters. Other polymers can also be used as the biocompatible polymer provided that they can be dissolved, cured or polymerized. Such polymers and copolymers include polyolefins, polyisobutylene and ethylene-$\alpha$-olefin copolymers; acrylic polymers (including methacrylates) and copolymers; vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile; polyvinyl ketones; polyvinyl aromatics such as polystyrene; polyvinyl esters such as polyvinyl acetate; copolymers of vinyl monomers with each other and with $\alpha$-olefins, such as etheylene-methyl methacrylate copolymers and ethylene-vinyl acetate copolymers; acrylonitrile-styrene copolymers; ABS resins; polyamides, such as nylon 66 and polycaprolactam; alkyd resins; polycarbonates; polyoxymethylenes; polyimides; polyethers; epoxy resins; polyurethanes; rayon; rayon-triacetate; cellophane; cellulose and its derivatives such as cellulose acetate, cellulose acetate butyrate, cellulose nitrate, cellulose propionate and cellulose ethers (e.g., carboxymethyl cellulose and hydroxyalkyl celluloses); or a mixture thereof. In one embodiment, biocompatible polymers further include hydrophilic synthetic and natural materials including but not limited to polyvinyl alcohols, polyethylene glycols, collagen, chitosan, Hyaluronic acid, etc.

A device that is made from reticulated elastomeric matrix 10 generally is coated by simple dip or spray coating with a polymer, optionally comprising a pharmaceutically-active agent, such as a therapeutic agent or drug. In one embodiment, the coating is a solution and the polymer content in the coating solution is from about 1% to about 40% by weight. In another embodiment, the polymer content in the coating solution is from about 1% to about 20% by weight. In another embodiment, the polymer content in the coating solution is from about 1% to about 10% by weight.

The solvent or solvent blend for the coating solution is chosen with consideration given to, inter alia, the proper balancing of viscosity, deposition level of the polymer, wetting rate and evaporation rate of the solvent to properly coat solid phase 12. In one embodiment, the solvent is chosen such that the polymer is soluble in the solvent. In another embodiment, the solvent is substantially completely removed from the coating. In another embodiment, the solvent is non-toxic, non-carcinogenic and environmentally benign. Mixed solvent systems can be advantageous for controlling the viscosity and evaporation rates. In all cases, the solvent should not react with the coating polymer. Solvents include by are not limited to: acetone, N-methylpyrrolidone ("NMP"), DMSO, toluene, methylene chloride, chloroform, 1,1,2-trichloroethane ("TCE"), various freons, dioxane, ethyl acetate, THF, DMF and DMAC.

In another embodiment, the film-forming coating polymer is a thermoplastic polymer that is melted, enters the pores 20 of the elastomeric matrix 10 and, upon cooling or solidifying, forms a coating on at least a portion of the solid material 12 of the elastomeric matrix 10. In another embodiment, the processing temperature of the thermoplastic coating polymer in its melted form is above about 60° C. In another embodiment, the processing temperature of the thermoplastic coating polymer in its melted form is above about 90° C. In another embodiment, the processing temperature of the thermoplastic coating polymer in its melted form is above about 120° C. In another embodiment, the processing temperature of the thermoplastic coating polymer in its melted form is above about 140° C.

In a further embodiment of the invention, described in more detail below, some or all of the pores 20 of elastomeric matrix 10 are coated or filled with a cellular ingrowth promoter. In another embodiment, the promoter can be foamed. In another embodiment, the promoter can be present as a film. The promoter can be a biodegradable or absorbable material to promote cellular invasion of elastomeric matrix 10 in vivo. Promoters include naturally occurring materials that can be enzymatically degraded in the human body or are hydrolytically unstable in the human body, such as fibrin, fibrinogen, collagen, elastin, hyaluronic acid and absorbable biocompatible polysaccharides, such as chitosan, starch, fatty acids (and esters thereof), glucoso-glycans and hyaluronic acid. In some embodiments, the pore surface of elastomeric matrix 10 is coated or impregnated, as described in the previous section but substituting the promoter for the biocompatible polymer or adding the promoter to the biocompatible polymer, to encourage cellular ingrowth and proliferation.

In one embodiment, the coating or impregnating process is conducted so as to ensure that the product "composite elastomeric implantable device", i.e., a reticulated elastomeric matrix and a coating, as used herein, retains sufficient resiliency after compression such that it can be delivery-device delivered, e.g., catheter, syringe or endoscope delivered. Some embodiments of such a composite elastomeric implantable device will now be described with reference to collagen, by way of non-limiting example, with the understanding that other materials may be employed in place of collagen, as described above.

One embodiment of the invention is a process for preparing a composite elastomeric implantable device comprising:
a) infiltrating an aqueous collagen slurry into the pores of a reticulated, porous elastomer, such as elastomeric matrix 10, which is optionally a biodurable elastomer product or optionally at least partially degradable elastomeric product; and
b) removing the water, optionally by lyophilizing, to provide a collagen coating, where the collagen coating optionally comprises an interconnected network of pores, on at least a portion of a pore surface of the reticulated, porous elastomer.
c) Optionally, the lyophilized collagen can be cross-linked to control the rate of in vivo enzymatic degradation of the collagen coating and/or to control the ability of the collagen coating to bond to elastomeric matrix 10.

Collagen may be infiltrated by forcing, e.g., with pressure, an aqueous collagen slurry, suspension or solution into the pores of an elastomeric matrix. The collagen may be Type I, II or III or a mixture thereof. In one embodiment, the collagen type comprises at least 90% collagen I. The concentration of collagen is from about 0.3% to about 2.0% by weight and the pH of the slurry, suspension or solution is adjusted to be from about 2.6 to about 5.0 at the time of lyophilization. Alternatively, collagen may be infiltrated by dipping an elastomeric matrix into a collagen slurry.

Coated Implantable Devices

One or more coatings may be applied endoporously by contacting with a film-forming biocompatible polymer either in a liquid coating solution or in a melt state under conditions suitable to allow the formation of a biocompatible polymer film. In one embodiment, the polymers that can be used for such coatings are film-forming biocompatible polymers with sufficiently high molecular weight so as not to be waxy or tacky. The polymers should also preferably adhere to the solid phase or the struts. Suitable biocompatible polymers include, but are not limited to, non-degradable polymers such as polyamides, polyolefins, nonabsorbable polyesters and preferably bioabsorbable aliphatic polyesters such as homopolymers and copolymers of lactic acid, glycolic acid, lactide, glycolide, para-dioxanone, trimethylene carbonate, ε-caprolactone or a mixture thereof. In one embodiment, the coatings can be made from biopolymer, such as collagen, elastin, and the like. The biopolymer can be biodegradable or bioabsorbable. Biocompatible polymers further include film-forming at least partially degradable polymers with relatively low chronic tissue response, such as polyurethanes, silicones, poly(meth)acrylates, polyesters, polyalkyl oxides (e.g., polyethylene oxide), polyvinyl alcohols, polyethylene glycols and polyvinyl pyrrolidone, as well as hydrogels, such as those formed from cross-linked polyvinyl pyrrolidinone and polyesters.

The implants, with reticulated structure with sufficient and required liquid permeability, can permit blood or another appropriate bodily fluid to access interior surfaces of the implants, which surfaces are optionally drug-bearing. This can happen due to the presence of inter-connected, reticulated open pores that form fluid passageways or fluid permeability providing fluid access all through and to the interior of the matrix for elution of pharmaceutically-active agents, e.g., a drug, or other biologically useful materials.

In a further embodiment of the invention, the pores of at least partially degradable reticulated elastomeric matrix that are used to fabricate the implants of this invention are coated or filled with a cellular ingrowth promoter. In another embodiment, the promoter can be foamed. In another embodiment, the promoter can be present as a film. The promoter can be a biodegradable material to promote cellular invasion of pores at least partially degradable reticulated elastomeric matrix that are used to fabricate the implants of this invention in vivo. Promoters include naturally occurring materials that can be enzymatically degraded in the human body or are hydrolytically unstable in the human body, such as fibrin, fibrinogen, collagen, elastin, hyaluronic acid and absorbable biocompatible polysaccharides, such as chitosan, starch, fatty acids (and esters thereof), glucoso-glycans and hyaluronic acid. In some embodiments, the pore surface of the at least partially degradable reticulated elastomeric matrix that are used to fabricate the implants of embodiments of this invention is coated or impregnated, as described in the previous section but substituting the promoter for the biocompatible polymer or adding the promoter to the biocompatible polymer, to encourage cellular ingrowth and proliferation.

Elastin, fibrin, collagen or other suitable clot-inducing material can also be coated onto an implant to provide an additional route of clot formation and these are internal coatings provided within and preferably throughout the pores of reticulated elastomeric matrix used. The functional agents can be coated, during the fabrication of the elastomeric matrix or during manufacturing of specific devices or implants and include synthetic and naturally derived drugs or pharmacological agents and/or other agents to promote fibroblast growth and other growth factors If desired, the outer surfaces of the elastomeric matrix or device can be coated with functional agents, such as those described herein, optionally employing an adjuvant that secures the functional agents to the surfaces and to reticulated elastomeric matrix pores adjacent the outer surfaces, where the agents will become quickly available. The functional agents can be coated, during the fabrication of the elastomeric matrix or during manufacturing of specific devices or implants. Such external coatings, which may be distinguished from internal coatings provided within and preferably throughout the pores of reticulated elastomeric matrix used, may comprise fibrin, elastin, collagen, synthetic and naturally derived drugs or pharmacological agents and/or other agents to promote fibroblast growth and other growth factors.

In one embodiment, the surfaces (internal and external) of the at least partially degradable reticulated elastomeric matrix are coated or treated to render them passive or relatively non-adhesive to certain plasma and extracellular matrix proteins with the goal to mask the foreign body response to the material in vivo.

In another embodiment, the surfaces (internal and external) of the at least partially degradable reticulated elastomeric matrix are coated or treated to promote adhesion, adsorption, and/or absorption of desirable extracellular matrix proteins, with the end goal to promote cellular migration, proliferation, attachment, and synthetic activity.

With regard to bio-passivating strategies for embodiments of the invention, surface modifications that can be considered to passivate the elastomeric matrix in terms of its biologic response include, for example, albumin (i.e., plasma protein which functions as an anti-adhesion layer, heparin which functions as an anti-coagulant, prostaglandin which functions as an inhibitor of macrophage activity thus limiting foreign body response, corticosteroid which functions as an inhibitor of macrophage activity thus limiting foreign body response and inflammation, plasma treatment and deposition, and self assembling peptides).

With regard to bioactivation strategies for embodiments of the invention, coatings and techniques that can be used to functionalize the reticulated elastomeric matrix to promote cell adhesion, proliferation, and synthetic activity include, for example, fibronectin, cell adhesion molecules (CAMS) that contain peptides, fibronectin, laminin, heparin, fibrin glue, and fibroblast growth factors, REDV (Arginine-glutamic-acid-aspartic-acid-valine), RGD (arginine-glycine-aspartic acid), growth factors (TGF-b family, PDGF, VEGF), platelet rich plasma (PRP), platelet Rich Fibrin Matrix (PRFM), antimicrobial agents, and pro-nectin.

Various methods that have been used for coating and surface modifications include, for example:
a) Surface graft polymerization—using plasma/corona discharge, gamma as well as UV radiation techniques. This will allow coarse thickness and molecular weight control, and may leave behind unreacted monomers;
b) Condensation reactions—biomolecules can be bound to functional groups on the surface of the reticulated elastomeric matrix material (COOH, $NH_2$, and OH);
c) Adsorption from solutions—many methods here, typically polyelectrolyte multilayer and self assembling peptide techniques; and
d) Surface segregation techniques.

In some applications, a device made from elastomeric matrix 10 can have at least a portion of the outermost or macro surface coated or fused in order to present a smaller macro surface area, because the internal surface area of pores below the surface is no longer accessible. In another embodiment a device made from elastomeric matrix 10 or composite mesh comprising reticulated elastomeric matrix 10 or the reinforced elastomeric matrix can have at least a portion of the outermost or macro surface coated with a film of biocompatible polymer. In another embodiment a device made from elastomeric matrix 10 or composite mesh comprising reticulated elastomeric matrix 10 the reinforced elastomeric matrix can have a significant portion of the outermost or macro surface coated with a film of biocompatible polymer. In another embodiment a device made from elastomeric matrix 10 or composite mesh comprising reticulated elastomeric matrix 10 the reinforced elastomeric matrix can have all of the outermost or macro surface coated with a film of biocompatible polymer. Without being bound by any particular theory, it is thought that this decreased surface area provides more predictable and easier delivery and transport through long tortuous channels inside delivery-devices. More importantly, the coating or the film can act as or impart anti-adhesion functionality in repair of some soft tissue defects such as in a number of hernia applications. In one embodiment, the coating or with a film of biocompatible polymer is the preferred embodiment because of the smoother surface of the coating or with a film of biocompatible polymer in comparison to the fused surface. The coating or the film is important to impart anti-adhesion functionality, and is especially important in anatomic sites such as abdominal wall wherein adhesions are likely to form between internal organ structures and the exposed mesh surface. In one embodiment, the surface coating or the film of biocompatible polymer preferably needs to be flexible that it provides ease of delivery through trocar and endoscopes and conform to the soft tissue healing site.

Surface coating or fusion film of biocompatible polymer alters the "porosity of the surface", i.e., at least partially reduces the percentage of pores open to the surface, or, in the limit, completely closes-off the pores of a coated or fused surface, i.e., that the surface is nonporous because it has substantially no pores remaining on the coated or fused surface. In one embodiment, surface coating or fusion or film of biocompatible polymer completely closes-off the pores of a coated or fused surface and makes it substantially or preferably totally impermeable to liquid or body fluid. However, surface coating or fusion or film of biocompatible polymer.

However, surface coating or fusion film of biocompatible polymer still allows the internal interconnected porous structure of elastomeric matrix 10 to remain open internally and on other non-coated or non-fused surfaces; e.g., the portion of a coated or fused pore not at the surface remains interconnected to other pores, and those remaining open surfaces can be used to foster cellular ingrowth and proliferation. In one embodiment, a coated and uncoated surface are orthogonal to each other. In another embodiment, a coated and uncoated surface are at an oblique angle to each other. In another embodiment, a coated and uncoated surface are adjacent. In another embodiment, a coated and uncoated surface are nonadjacent. In another embodiment, a coated and uncoated surface are in contact with each other. In another embodiment, a coated and uncoated surface are not in contact with each other.

In embodiment, there is one or two or three dimensional reinforcements between the surface coating or film of biocompatible polymer and the internal interconnected and inter-communicating reticulated structure of elastomeric matrix 10 containing the uncoated surface. In another embodiment, there is one or two dimensional reinforcements between the surface coating or film of biocompatible polymer and the internal interconnected and inter-communicating reticulated structure of elastomeric matrix 10 containing the uncoated surface. In another embodiment, there reinforcement between the surface coating or film of biocompatible polymer and the internal interconnected and inter-communicating reticulated structure of elastomeric matrix 10 containing the uncoated surface and the reinforcement is a two-dimensional reinforcement, and the two-dimensional reinforcement may further comprise a grid of a plurality of one-dimensional reinforcement elements, wherein the one-dimensional reinforcement elements cross each other's paths. In further embodiments, the two-dimensional reinforcement may be a two-dimensional mesh made up of intersecting one-dimensional reinforcement elements. In one embodiment, the composite mesh comprising reticulated elastomeric matrix 10 is a multi-layered structure in which there is two dimensional reinforcements between the surface coating or film of biocompatible polymer and the internal interconnected and inter-communicating reticulated structure of elastomeric matrix 10 containing the uncoated surface. In another embodiment, the composite mesh comprising reticulated elastomeric matrix 10 is a multi-layered structure in which there is two dimensional reinforcements comprising a grid of a plurality of one-dimensional reinforcement elements between the surface coating or film of biocompatible polymer and the internal interconnected and inter-communicating reticulated structure of elastomeric matrix 10 containing the uncoated surface.

In other applications, one or more planes of the macro surface of an implantable device made from at least partially degradable reticulated elastomeric matrix 10 may be coated, fused or melted to improve its attachment efficiency to attaching means, e.g., anchors or sutures, so that the attaching means does not tear-through or pull-out from the implantable device. Without being bound by any particular theory, creation of additional contact anchoring macro surface(s) on the implantable device, as described above, is thought to inhibit tear-through or pull-out by providing fewer voids and greater resistance.

The fusion and/or selective melting of the macro surface layer of elastomeric matrix 10 can be brought about in several different ways. In one embodiment, a knife or a blade can be used to cut a block of elastomeric matrix 10 into sizes and shapes for making final implantable devices can be heated to an elevated temperature. In another embodiment, a device of desired shape and size is cut from a larger block of elastomeric matrix 10 by using a laser cutting device and, in the process, the surfaces that come into contact with the laser beam are fused. In another embodiment, a cold laser cutting device is used to cut a device of desired shape and size. In yet another embodiment, a heated mold can be used to impart the desired size and shape to the device by the process of heat compression. A slightly oversized elastomeric matrix 10, cut from a larger block, can be placed into a heated mold. The mold is closed over the cut piece to reduce its overall dimensions to the desired size and shape and fuse those surfaces in contact with the heated mold. In each of the aforementioned embodiments, the processing temperature for shaping and sizing is greater than about 15° C. in one embodiment. In another embodiment, the processing temperature for shaping and sizing is in excess of about 100° C. In another embodiment, the processing temperature for shaping and sizing is in excess of about 130° C. In another embodiment, the layer(s) and/or portions of the macro surface not being fused are protected from exposure by covering them during the fusing of the macro surface.

The coating on the macro surface or the film of biocompatible polymer on the macro surface can be made from a biocompatible polymer, which can include be both biodegradable or absorbable and non-biodegradable or non-absorbable polymers or non-absorbable polymers or permanent polymers. Suitable absorbable, biodegradable, non-biodegradable, non-absorbable polymers or permanent polymers include those biocompatible polymers disclosed in the section titled "Imparting Endopore Features". Exemplary biodegradable polymers that can be used as coatings include but not limited to copolymers of caprolactone, lactic acid, glycolic acid, acid d-, l- and meso lactide and para-dioxanone, etc. or mixtures thereof. In another embodiment, biodegradable or bioabsorbable coatings made from copolymers of caprolactone with lactic acid, glycolic acid, acid d-, l- and meso lactide and para-dioxanone para-dioxanone are considered favorable for coating applications for providing anti-adhesion properties with copolymers of caprolactone with lactic acid in the ratio of 40/60, 30/70 or 20/80 polycaprolactone to polylactic acid being preferred for anti-adhesion properties. Further, the thermoplastic biodegradable or bioabsorbable polymer used for coating may comprise an $\epsilon$-caprolactone copolymer, and optionally an $\epsilon$-caprolactone-lactic acid copolymer or an $\epsilon$-caprolactone-lactide copolymer. In another embodiment, biodurable or permanent biocompatible polymers further include polymers with relatively low chronic tissue response, such polyurethane such as polycarbonate polyurethanes, polysiloxane polyurethanes, poly(siloxane-co-ether)polyurethanes, polycarbonate polysiloxane polyurethanes, polycarbonate urea-urethanes, polycarbonate polysiloxane urea-urethanes and the like and their mixtures. In another embodiment, biodurable or permanent biocompatible polymers include silicone. Biologically derived biomaterials are utilized as anti-adhesion coatings in other embodiments of the invention. Examples of suitable biologically derived biomaterials include reprocessed collagen, Hyaluronic acid (HA) or functionalized proteoglycans, and any of these combined with PEG. It is to be understood that that listing of materials is illustrative but not limiting. In one embodiment, surface pores are closed by applying an absorbable polymer melt coating onto a shaped elastomeric matrix. Together, the elastomeric matrix and the coating form the device. In another embodiment, surface pores are closed by applying an absorbable polymer solution coating onto a shaped elastomeric matrix to form a device. In another embodiment, the coating and the elastomeric matrix, taken together, can occupy a larger volume than the uncoated elastomeric matrix alone.

The coating or the film coating on elastomeric matrix 10 can be applied to the elastomeric matrix or to the reinforcements by use of an adhesive or bonding material that can be applied in various fashion such as by, e.g., dipping or spraying a coating solution comprising a polymer or a polymer and in embodiment that solution can be admixed with a pharmaceutically-active agent. In one embodiment, the polymer content in the coating solution is from about 1% to about 40% by weight. In another embodiment, the polymer content in the coating solution is from about 1% to about 20% by weight. In another embodiment, the polymer content in the coating solution is from about 1% to about 10% by weight. In another embodiment, the polymer content in the coating solution is from about 1% to about 10% by weight. In another embodiment, the coating may be applied as a solution in a solvent for the polymer, for example, with a polymer content in the coating solution of from about 1% to about 40% by weight. According to other embodiments, the coating solution may be applied by dip coating or spray coating the solution onto the reticulated elastomeric matrix, the solvent can be substantially or completely removed from the coating, and/or the solvent may be non-toxic and non-carcinogenic. In another embodiment, the layer(s) and/or portions of the macro surface not being solution-coated are protected from exposure by covering them during the solution-coating of the macro surface. The solvent or solvent blend for the coating solution is chosen, e.g., based on the considerations discussed in the previous section (i.e., in the "Imparting Endopore Features" section). In one embodiment, the coating or bonding material can be cured between 50° C. and 150° C. and in another embodiment between 60° C. and 120° C. In one embodiment, the adhesive or bonding material can be cured between 10 minutes and 3 hours and in another embodiment between 15 minutes and 2 hours.

In one embodiment, the coating on elastomeric matrix 10 may be applied by melting a film-forming coating polymer and applying the melted polymer onto the elastomeric matrix 10. In another embodiment, the film-forming coating polymer is a thermoplastic polymer that is melted, enters the pores 20 of the elastomeric matrix 10 or composite mesh comprising reticulated elastomeric matrix 10 and, upon cooling or solidifying, forms a coating on at least a portion of the solid material 12 of the elastomeric matrix 10. In other embodiments, a thermoplastic polymer is melted and applied to coat the reticulated elastomeric matrix. In another embodiment, the coating on elastomeric matrix 10 may be applied by melting the film-forming coating polymer and applying the melted polymer through a die, in a process such as extrusion or coextrusion, as a thin layer of melted polymer onto a mandrel formed by elastomeric matrix 10. In either of these embodiments, the melted polymer coats the macro surface and bridges or plugs pores of that surface but does not penetrate into the interior to any significant depth. Without being bound by any particular theory, this is thought to be due to the high viscosity of the melted polymer. Thus, the reticulated nature of portions of the elastomeric matrix removed from the macro surface, and portions of the elastomeric matrix's macro surface not in contact with the melted polymer, is maintained. Upon cooling and solidifying, the melted polymer forms a layer of solid coating on the elastomeric matrix 10. In one embodiment, the processing temperature of the melted thermoplastic coating polymer is at least about 60° C. In another embodiment, the processing temperature of the melted thermoplastic coating polymer is at least above about 90° C. In another embodiment, the processing temperature of the melted thermoplastic coating polymer is at least above about 120° C. In another embodiment, the processing temperature of the melted thermoplastic coating polymer is at least above about 140° C. The melt can be applied by extruding or coextruding or injection molding or compression molding or compressive molding the melt onto the reticulated elastomeric matrix. In another embodiment, the layer(s) and/or portions of the macro surface not being melt-coated are protected from exposure by covering them during the melt-coating of the macro surface.

Another embodiment of the invention employs a collagen-coated composite elastomeric implantable device, as described above, configured as a sleeve extending around the implantable device. The collagen matrix sleeve can be implanted at a tissue repair and regeneration site, either adjacent to and in contact with that site. So located, the collagen matrix sleeve can be useful to help retain the elastomeric matrix 10, facilitate the formation of a tissue seal and help prevent leakage. The presence of the collagen in elastomeric matrix 10 can be used to enhance cellular ingrowth and proliferation and improve mechanical stability, in one embodiment, by enhancing the attachment of fibroblasts to the collagen. The presence of collagen can be used to stimulate earlier and/or more complete infiltration of the interconnected pores of elastomeric matrix 10.

In one embodiments, the film of biocompatible polymer that is to be used as coating is first formed by extrusion, injection molding compression molding or solvent casting. The film of biocompatible polymer is then bonded to the implantable device using an adhesive. The adhesive can be applied between the reinforcement and elastomeric matrix and cured. In another embodiment, the adhesive can be applied either to reinforcement or the elastomeric matrix or both before being cured. The adhesive can be applied by dip or spray coating, painted with a brush, by use of customized coating fixtures that can lay down or deliver a thin layer of adhesive using blades with adjustable heights followed by transfer of the thin layer of adhesive on to the reinforcement or the elastomeric matrix or both. In one embodiment, the film of biocompatible polymer is bonded by an adhesive applied by dip coating. Exemplary adhesives include but not limited to Nusil™, Chronoflex™, Elast-Eon™ or a biodegradable polymer.

In another embodiment of the composite mesh comprising reticulated elastomeric matrix 10, the film of biocompatible polymer is first melt bonded to the one or two dimensional reinforcements which in turn is then bonded to reticulated elastomeric matrix the using an adhesive. In another embodiment of the composite mesh comprising reticulated elastomeric matrix 10, the film of biocompatible polymer is first melt bonded to one side of the one or two dimensional reinforcements whose other side in turn is then bonded to reticulated elastomeric matrix the using an adhesive. In another embodiment of the composite mesh comprising reticulated elastomeric matrix 10, the film of biocompatible polymer is first melt bonded to the one or two dimensional reinforcements which in turn is then bonded to reticulated elastomeric matrix containing the uncoated surface the using an adhesive. In another embodiment of the composite mesh comprising reticulated elastomeric matrix 10, the film of biocompatible polymer is first melt bonded to the one or two dimensional reinforcements which in turn is then bonded to reticulated elastomeric matrix surface the using an adhesive. Exemplary adhesives include but not limited to Nusil™, Chronoflex™, Elast-Eon™ or a biodegradable polymer.

In another embodiment of the composite mesh comprising reticulated elastomeric matrix 10, the film of biocompatible polymer is first melt bonded to the one or two dimensional reinforcements which in turn is then again melt bonded to reticulated elastomeric matrix. In another embodiment of the composite mesh comprising reticulated elastomeric matrix 10, the film of biocompatible polymer is first melt bonded to one side of the one or two dimensional reinforcements whose other side in turn is then again melt bonded to reticulated elastomeric matrix. In another embodiment of the composite mesh comprising reticulated elastomeric matrix 10, the film of biocompatible polymer is first melt bonded to the one or two dimensional reinforcements which in turn is then again melt bonded to reticulated elastomeric matrix containing the uncoated surface. In another embodiment of the composite mesh comprising reticulated elastomeric matrix 10, the film of biocompatible polymer is first melt bonded to the one or two dimensional reinforcements which in turn is then again melt bonded to reticulated elastomeric matrix surface. The melt bonding can take place by either melting or partially melting the film of biocompatible polymer. In another embodiment, the melt bonding can take place by either melting or partially melting the a second film forming biocompatible coating polymer that can include be both biodegradable or absorbable and non-biodegradable or non-absorbable polymers or permanent polymers. In one embodiment, the melt bonding processing temperature is at least about 60° C. In another embodiment, the melt bonding processing temperature is at least about 90° C. In another embodiment, the melt bonding processing temperature is at least about 120° C. In another embodiment, the melt bonding processing temperature is at least about 140° C.

Embodiments of the invention composite mesh comprising reticulated elastomeric and a coating include possible alternative designs and configurations. In embodiment, there is one or two or three dimensional reinforcements between the surface coating or film of biocompatible polymer and one layer of elastomeric matrix with internal structure that is reticulated. In embodiment, there is one or two dimensional reinforcements between the surface coating or film of biocompatible and one layer of elastomeric matrix with internal structure that is reticulated. In both of these cases, only one layer of reticulated structure of elastomeric matrix comprising interconnected and inter-communicating is being reinforced and using reinforcing elements that can preferably be one or two dimensional. In one embodiment, the reinforcement is a two-dimensional reinforcement, and the two-dimensional reinforcement may further comprise a grid of a plurality of one-dimensional reinforcement elements, wherein the one-dimensional reinforcement elements cross each other's paths. In another embodiment, the surface coating or film of biocompatible polymer is placed, attached, adhesive bonded, melt bonded to the reticulated elastomeric matrix that is being reinforced. In another embodiment, the surface coating or film of biocompatible polymer is placed, attached, adhesive bonded, melt bonded to the one or two or three dimensional reinforcements.

In one embodiment, the surface coating or film of biocompatible polymer is applied or incorporated on to a composite where the reinforcement is incorporated between two layers of the elastomeric matrix. In another embodiment, the surface coating or film of biocompatible polymer is applied or incorporated on to a composite where the reinforcement is incorporated between two layers of the elastomeric matrix such as a sandwich design. The surface coating or film of biocompatible polymer is placed, attached, adhesive bonded, melt bonded to one of the two sides the reticulated elastomeric matrix that is being reinforced with one or two or three dimensional reinforcements. In another embodiment, the surface coating or film of biocompatible polymer is placed, attached, adhesive bonded, melt bonded to both sides the reticulated elastomeric matrix that is being reinforced with one or two or three dimensional reinforcements.

In one embodiment, the surface coating or film of biocompatible polymer is applied or incorporated on to a composite containing multiple layers of reinforcement and elastomeric matrix can be stacked in an alternating fashion.

Pharmaceutically-Active Agent Delivery

In another embodiment, the film-forming polymer used to coat at least partially degradable reticulated elastomeric matrix 10 can provide a vehicle for the delivery of and/or the controlled release of a pharmaceutically-active agent, for example, a drug, such as is described in the applications to which priority is claimed in U.S. Patent Application Publication No. 2007/019108, the disclosures of which are incorporated herein by this reference. In another embodiment, the pharmaceutically-active agent is admixed with, covalently bonded to, adsorbed onto and/or absorbed into the coating of elastomeric matrix 10 to provide a pharmaceutical composition. In another embodiment, the components, polymers and/or blends that are used to form the foam comprise a pharmaceutically-active agent. To form these foams, the previously described components, polymers and/or blends are admixed with the pharmaceutically-active agent prior to forming the foam or the pharmaceutically-active agent is loaded into the foam after it is formed.

In one embodiment, the coating polymer and pharmaceutically-active agent can have a common solvent. This can provide a coating that is a solution. In another embodiment, the pharmaceutically-active agent can be present as a solid dispersion in a solution of the coating polymer in a solvent.

An at least partially degradable reticulated elastomeric matrix 10 comprising a pharmaceutically-active agent may be formulated by mixing one or more pharmaceutically-active agents with the polymer used to make the foam, with the solvent or with the polymer-solvent mixture and foamed. Alternatively, a pharmaceutically-active agent can be coated onto the foam, in one embodiment, using a pharmaceutically-acceptable carrier. If melt-coating is employed, then, in another embodiment, the pharmaceutically-active agent withstands melt processing temperatures without substantial diminution of its efficacy.

Formulations comprising a pharmaceutically-active agent can be prepared from one or more pharmaceutically-active agents by admixing, covalently bonding, adsorbing onto and/or absorbing into the same with the coating of the at least partially degradable reticulated elastomeric matrix 10 or by incorporating the pharmaceutically-active agent into additional hydrophobic or hydrophilic coatings. The pharmaceutically-active agent may be present as a liquid, a finely divided solid or another appropriate physical form. Typically, but optionally, the matrix can include one or more conventional additives, such as diluents, carriers, excipients, stabilizers and the like.

In another embodiment, a top coating can be applied to delay release of the pharmaceutically-active agent. In another embodiment, a top coating can be used as the matrix for the delivery of a second pharmaceutically-active agent. A layered coating, comprising respective layers of fast- and slow-hydrolyzing polymer, can be used to stage release of the pharmaceutically-active agent or to control release of different pharmaceutically-active agents placed in the different layers. Polymer blends may also be used to control the release rate of different pharmaceutically-active agents or to provide a desirable balance of coating characteristics (e.g., elasticity, toughness) and drug delivery characteristics (e.g., release profile). Polymers with differing solvent solubilities can be used to build-up different polymer layers that may be used to deliver different pharmaceutically-active agents or to control the release profile of a pharmaceutically-active agents.

The amount of pharmaceutically-active agent present depends upon the particular pharmaceutically-active agent employed and medical condition being treated. In one embodiment, the pharmaceutically-active agent is present in an effective amount. In another embodiment, the amount of pharmaceutically-active agent represents from about 0.01% to about 60% of the coating by weight. In another embodiment, the amount of pharmaceutically-active agent represents from about 0.01% to about 40% of the coating by weight. In another embodiment, the amount of pharmaceutically-active agent represents from about 0.1% to about 20% of the coating by weight.

Many different pharmaceutically-active agents can be used in conjunction with the at least partially degradable reticulated elastomeric matrix. In general, pharmaceutically-active agents that may be administered via pharmaceutical compositions of this invention include, without limitation, any therapeutic or pharmaceutically-active agent (including but not limited to nucleic acids, proteins, lipids, and carbohydrates) that possesses desirable physiologic characteristics for application to the implant site or administration via a pharmaceutical compositions of the invention. Therapeutics include, without limitation, antiinfectives such as antibiotics and antiviral agents; chemotherapeutic agents (e.g., anticancer agents); anti-rejection agents; analgesics and analgesic combinations; anti-inflammatory agents; hormones such as steroids; growth factors (including but not limited to cytokines, chemokines, and interleukins) and other naturally derived or genetically engineered proteins, polysaccharides, glycoproteins and lipoproteins. These growth factors are described in The Cellular and Molecular Basis of Bone Formation and Repair by Vicki Rosen and R. Scott Thies, published by R. G. Landes Company, hereby incorporated herein by reference. Additional therapeutics include thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroids, non-steroidal anti-inflammatory agents, immunosuppressive agents, growth hormone antagonists, growth factors, dopamine agonists, radiotherapeutic agents, peptides, proteins, enzymes, extracellular matrix components, angiotensin-converting enzyme (ACE) inhibitors, free radical scavengers, chelators, antioxidants, anti polymerases, antiviral agents, photodynamic therapy agents and gene therapy agents.

Additionally, various proteins (including short chain peptides), growth agents, chemotactic agents, growth factor receptors or ceramic particles can be added to the foams during processing, adsorbed onto the surface or back-filled into the foams after the foams are made. For example, in one embodiment, the pores of the foam may be partially or completely filled with biocompatible resorbable synthetic polymers or biopolymers (such as collagen or elastin), biocompatible ceramic materials (such as hydroxyapatite), and combinations thereof, and may optionally contain materials that promote tissue growth through the device. Such tissue-growth materials include but are not limited to autograft, allograft or xenograft bone, bone marrow and morphogenic proteins. Biopolymers can also be used as conductive or chemotactic materials, or as delivery vehicles for growth factors. Examples include recombinant collagen, animal-derived collagen, elastin and hyaluronic acid. Pharmaceutically-active coatings or surface treatments could also be present on the surface of the materials. For example, bioactive peptide sequences (RGD's) could be attached to the surface to facilitate protein adsorption and subsequent cell tissue attachment.

Bioactive molecules include, without limitation, proteins, collagens (including types IV and XVIII), fibrillar collagens (including types I, II, III, V, XI), FACIT collagens (types IX, XII, XIV), other collagens (types VI, VII, XIII), short chain collagens (types VIII, X), elastin, entactin-1, fibrillin, fibronectin, fibrin, fibrinogen, fibroglycan, fibromodulin, fibulin, glypican, vitronectin, laminin, nidogen, matrilin, perlecan, heparin, heparan sulfate proteoglycans, decorin, filaggrin, keratin, syndecan, agrin, integrins, aggrecan, biglycan, bone sialoprotein, cartilage matrix protein, Cat-301 proteoglycan, CD44, cholinesterase, HB-GAM, hyaluronan, hyaluronan binding proteins, mucins, osteopontin, plasminogen, plasminogen activator inhibitors, restrictin, serglycin, tenascin, thrombospondin, tissue-type plasminogen activator, urokinase type plasminogen activator, versican, von Willebrand factor, dextran, arabinogalactan, chitosan, polyactideglycolide, alginates, pullulan, gelatin and albumin.

Additional bioactive molecules include, without limitation, cell adhesion molecules and matricellular proteins, including those of the immunoglobulin (Ig; including monoclonal and polyclonal antibodies), cadherin, integrin, selectin, and H-CAM superfamilies. Examples include, without limitation, AMOG, CD2, CD4, CD8, C-CAM (CELL-CAM 105), cell surface galactosyltransferase, connexins, desmocollins, desmoglein, fasciclins, F11, GP Ib-IX complex, intercellular adhesion molecules, leukocyte common antigen protein tyrosine phosphate (LCA, CD45), LFA-1, LFA-3, mannose binding proteins (MBP), MTJC18, myelin associated glycoprotein (MAG), neural cell adhesion molecule (NCAM), neurofascin, neruoglian, neurotactin, netrin, PECAM-1, PH-20, semaphorin, TAG-1, VCAM-1, SPARC/osteonectin, CCN1 (CYR61), CCN2 (CTGF; Connective Tissue Growth Factor), CCN3 (NOV), CCN4 (WISP-1), CCN5 (WISP-2), CCN6 (WISP-3), occludin and claudin. Growth factors include, without limitation, BMP's (1-7), BMP-like Proteins (GFD-5, -7, -8), epidermal growth factor (EGF), erythropoietin (EPO), fibroblast growth factor (FGF), growth hormone (GH), growth hormone releasing factor (GHRF), granulocyte colony-stimulating factor (G-CSF), granulocyte-macrophage colony-stimulating factor (GM-CSF), insulin, insulin-like growth factors (IGF-I, IGF-II), insulin-like growth factor binding proteins (IGFBP), macrophage colony-stimulating factor (M-CSF), Multi-CSF (Il-3), platelet-derived growth factor (PDGF), tumor growth factors (TGF-alpha, TGF-beta), tumor necrosis factor (TNF-alpha), vascular endothelial growth factors (VEGF's), angiopoietins, placenta growth factor (PIGF), interleukins, and receptor proteins or other molecules that bind with the aforementioned factors. Short-chain peptides include, without limitation (designated by single letter amino acid code), RGD, EILDV, RGDS, RGES, RFDS, GRDGS, GRGS, GRGDTP and QPPRARI.

Tissue Culture

The at least partially degradable reticulated elastomeric matrix of embodiments of this invention can support cell types including cells secreting structural proteins and cells that produce proteins characterizing organ function. The ability of the elastomeric matrix to facilitate the co-existence of multiple cell types together and its ability to support protein secreting cells demonstrate the applicability of the elastomeric matrix in organ growth in vitro or in vivo and in organ reconstruction. In addition, the at least partially degradable reticulated elastomeric matrix may also be used in the scale up of human cell lines for implantation to the body for many applications including implantation of fibroblasts, chondrocytes, osteoblasts, osteoclasts, osteocytes, synovial cells, bone marrow stromal cells, stem cells, fibrocartilage cells, endothelial cells, smooth muscle cells, adipocytes, cardiomyocytes, myocytes, keratinocytes, hepatocytes, leukocytes, macrophages, endocrine cells, genitourinary cells, lymphatic vessel cells, pancreatic islet cells, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, epithelial cells, nerve cells, stem cells, progenitor cells, myoblasts and intestinal cells.

The approach to engineer new tissue can be obtained through implantation of cells seeded in elastomeric matrices (either prior to or concurrent to or subsequent to implantation). In this case, the elastomeric matrices may be configured either in a closed manner to protect the implanted cells from the body's immune system, or in an open manner so that the new cells can be incorporated into the body. Thus in another embodiment, the cells may be incorporated, i.e. cultured and proliferated, onto the elastomeric matrix prior, concurrent or subsequent to implantation of the elastomeric matrix in the patient.

In one embodiment, the implantable device made from at least partially degradable reticulated elastomeric matrix can be seeded with a type of cell and cultured before being inserted into the patient, optionally using a delivery-device, for the explicit purpose of tissue repair or tissue regeneration. It is necessary to perform the tissue or cell culture in a suitable culture medium with or without stimulus such as stress or orientation. The cells include fibroblasts, chondrocytes, osteoblasts, osteoclasts, osteocytes, synovial cells, bone marrow stromal cells, stem cells, fibrocartilage cells, endothelial cells and smooth muscle cells.

Surfaces on the at least partially degradable reticulated elastomeric matrix possessing different pore morphology, size, shape and orientation may be cultured with different types of cells to develop cellular tissue engineering implantable devices that are specifically targeted towards orthopedic applications, especially in soft tissue attachment, repair, regeneration, augmentation and/or support encompassing the spine, shoulder, knee, hand or joints, and in the growth of a prosthetic organ. In another embodiment, all the surfaces on the at least partially degradable reticulated elastomeric matrix possessing similar pore morphology, size, shape and orientation may be so cultured.

In other embodiments, the at least partially degradable reticulated elastomeric matrix of embodiments of this invention may have applications in the areas of mammary prostheses, pacemaker housings, LVAD bladders or as a tissue bridging matrix.

Compressive Molding

In addition to varying the chemistry and/or processing of degradable elastomeric matrix in order to obtain a range of desirable or targeted implantable device performance, post-reticulation steps, such as imparting endopore features (already discussed above) can also be used to obtain a range of desirable or targeted implantable device performance. In another post-reticulation embodiment, the degradable reticulated elastomeric matrix is compressed in at least one dimension, e.g., 1-dimensional compression, 2-dimensional compression, or 3 dimensional compression, in a compressive molding process and, if reinforced with a reinforcement as discussed in detail below, remains compressed during the inclusion of the reinforcement.

In one secondary processing method, referred to herein as compressive molding, desirable enhanced performance is obtained by densification and/or orientation in one dimension, two dimensions or three dimensions using different temperatures. In one embodiment, the densification and/or orientation can be effected without the use of a mold. In another embodiment, the densification and/or orientation is facilitated by using a mold. As discussed below, the densification and/or orientation is usually carried out at elevated temperatures above over a period of time where the length of time depends on the temperature(s) used. In another embodiment, the compressive molding process is conducted in a batch process. In another embodiment, the compressive molding process is conducted in a continuous process.

A "preform" is a shaped uncompressed reticulated elastomeric matrix that has been cut or machined from a block of degradable reticulated elastomeric matrix for use in secondary processing, such as compressive molding. The preform can have a predetermined size and shape. In one embodiment, the size and shape of the preform is determined by the final or desired compression ratio that will be imparted during compressive molding.

When a mold is used, the mold cavity can have a fixed shape, such as a cylinder, cube, sphere or ellipsoid, or it can have an irregular shape. The reticulated cross-linked at least partially degradable elastomeric polycaprolactone urea-urethane matrix, upon being compressive molded, conforms to a great degree to the geometry of the mold at the end of the densification and/or orientation step.

Compressive molding can also be carried out in a mold the contours of which can change during the compressive molding process, e.g., from an initial shape and/or size to a final shape and/or size. The change in the dimension of this mold can be initiated or activated by application of heat or application of load. In one such example, a cylindrically-shaped preform of degradable reticulatedelastomeric matrix having diameter $d3$ can be placed inside a thin-walled PTFE (polytetrafluoroethylene) shrink-wrap tube having initial diameter, $d1$, greater than $d3$. Upon application of external heat and/or load, the PTFE shrink-wrap tube can shrink from its initial diameter $d1$ to a smaller final diameter of $d2$. The cylindrical preform with diameter $d3$ can be compressed to a final diameter substantially equal to or equal to $d2$. The compressed degradable reticulatedelastomeric matrix can conform to a great degree to the geometry of the mold which, in this embodiment, is the heat-shrunk PTFE tubing.

In one embodiment, the densification and/or orientation believed to be imparted to the reticulated elastomeric matrix by compressive molding results in property enhancement and/or performance enhancement for the compressed reticulated elastomeric matrix, such as in its mechanical properties, e.g., tensile strength, tensile modulus, compressive strength, compressive, modulus and/or tear strength. In another embodiment, the densification and/or orientation believed to be imparted to the reticulated elastomeric matrix by compressive molding results in performance enhancement related to delivery, conformability, handling and/or filling at the tissue healing site.

During compressive molding, in one embodiment at least one dimension of the preform, e.g., the length and/or diameter of a cylindrical preform, is reduced in size. In another embodiment, during compressive molding one dimension of a preform, such as the thickness dimension of a cube, is reduced while its other two dimensions remain substantially unchanged. During this compressive molding process, each face is believed to be approximately motionless or fixed relative to the outside surface of the preform in contact with a face as the faces are pushed closer together; therefore, this process of compressive molding can also be described as a "fixed mold wall" compressive molding process.

In another embodiment, substantially all of the changes in preform volume occurring upon compressive molding can be accounted for by the dimensional change occurring only in one dimension. In another embodiment, all of the changes in preform volume occurring upon compressive molding can be accounted for by the dimensional change occurring only in one dimension. In another embodiment, substantially all of the changes in preform volume occurring upon compressive molding can be accounted for by the dimensional change occurring only in the thickness dimension.

The linear compression ratio, defined herein as the ratio of the original magnitude of the dimension that is reduced during compressive molding to the magnitude of the final dimension after compressive molding, is from about 1.15 to about 9.0. In another embodiment, the linear compression ratio is from about 2.5 to about 7.0. In another embodiment, the linear compression ratio is from about 2.0 to about 6.0.

If the reduction in the dimension that is reduced during compressive molding is expressed in terms of linear compressive strain, i.e., the change in a dimension over that original dimension, the linear compressive strain is from about 15% to about 90%. In another embodiment, the linear compressive strain is from about 25% to about 90%. In another embodiment, the linear compressive strain is from about 30% to about 85%. In another embodiment, the linear compressive strain is from about 40% to about 75%.

In another embodiment, during compressive molding the radius dimension of a cylindrical preform is reduced, i.e., the circumference is reduced, such that the dimensional reduction occurs in two directions, while, in the other direction, the cylinder's height remains substantially unchanged. In another embodiment, during compressive molding the radius dimension of a cylindrical preform is reduced, while, in the other direction, the cylinder's height remains unchanged.

In another embodiment, substantially all of the changes in preform volume occurring upon compressive molding can be accounted for by the dimensional change occurring only in two dimensions. In another embodiment, all of the changes in preform volume occurring upon compressive molding can be accounted for by the dimensional change occurring only in two dimensions. In another embodiment, substantially all of the changes in preform volume occurring upon compressive molding can be accounted for by the dimensional change occurring only in the radial dimension. In another embodiment, all of the changes in preform volume occurring upon compressive molding can be accounted for by the dimensional change occurring only in the radial dimension.

The radial compression ratio, defined herein as the ratio of the original magnitude of the cylindrical preform's radius to the magnitude of the final radius after compressive molding, can be from about 1.2 to about 6.7. In another embodiment, the radial compression ratio is from about 1.5 to about 6.0. In another embodiment, the radial compression ratio is from about 2.5 about 6.0. In another embodiment, the radial compression ratio is from about 2.0 to about 5.0.

In another embodiment, the cross-sectional compression ratio, defined herein as the ratio of the original magnitude of the cylindrical preform's cross-sectional area to the magnitude of the final cross-sectional area after compressive molding, is from about 1.5 to about 47. In another embodiment, the cross-sectional compression ratio is from about 1.5 to about 25. In another embodiment, the cross-sectional compression ratio is from about 2.0 to about 9.0. In another embodiment, the cross-sectional compression ratio is from about 2.0 to about 7.0.

If the reduction in the cross-sectional area during compressive molding of a cylindrical preform is expressed in terms of cross-sectional compressive strain, i.e., the change in a cross-sectional area over that original cross-sectional area, the cross-sectional compressive strain can be from about 25% to about 90%. In another embodiment, the cross-sectional compressive strain is from about 33% to about 90%. In another embodiment, the cross-sectional compressive strain is from about 50% to about 88%.

Compressive molding of the at least partially degradable reticulated elastomeric matrix materials of the present invention is conducted at temperatures above 25° C. and can be carried out from about 80° C. to about 150° C. in one embodiment, from about 100° C. to about 150° C. in another embodiment, or from about 110° C. to about 145° C. in another embodiment. In another embodiment, as the temperature at which the compressive molding process is carried out increases, the time at which the compressive molding process is carried out decreases. The time for compressive molding is usually from about 10 seconds to about 10 hours. In another embodiment, the compressive molding time is from about 30 seconds to about 5 hours. In another embodiment, the compressive molding time is from about 30 seconds to about 3 hours. As the temperature at which the compressive molding process is conducted is raised, the time for compressive molding decreases. At higher temperatures, the time for compressive molding must be short, as a long compressive molding time may cause the degradable reticulatedelastomeric matrix to thermally degrade. For example, in one embodiment, at temperatures of about 140° C., the time for compressive molding is about 30 minutes or less in one embodiment, about 10 minutes or less in another embodiment, or about 5 minutes or less in another embodiment. In another embodiment, at a temperature of about 130° C., the time for compressive molding is about 60 minutes or less in one embodiment, about 20 minutes or less in another embodiment, or about 10 minutes or less in another embodiment. In another embodiment, at temperatures of about 110° C., the time for compressive molding is about 240 minutes or less in one embodiment, about 120 minutes or less in another embodiment, or about 30 minutes or less in another embodiment.

After compressive molding, the permeability of the compressed degradable reticulated elastomeric matrix usually decreases and, thereby, potentially reduces the ability of the compressed degradable reticulatedelastomeric matrix to provide for tissue ingrowth and proliferation. Therefore, it is important to maintain good fluid permeability after compressive molding even after the cross-sectional area is reduced by about 50% or in another embodiment, the cross-sectional area is reduced by about 60% or in another embodiment, the cross-sectional area is reduced by about 80%.

Reinforcement Incorporation

Degradable elastomeric matrix can undergo a further post-reticulation processing step or steps, in addition to reticulation, imparting endopore features and compressive molding already discussed above. For example, in another embodiment, the degradable reticulatedelastomeric matrix is reinforced with a reinforcement to create composite mesh comprising degradable reticulatedelastomeric matrix. In this case, the composite mesh comprises at least one functional element, i.e. the reinforcement, designed to enhance the mechanical load bearing functions such as strength, stiffness, tear resistance, burst strength, suture pull out strength etc. In other embodiments, the reinforcement is in at least one dimension, e.g., a 1 dimensional reinforcement (such as a fiber), a 2-dimensional reinforcement (such as a 2-dimensional mesh made up of intersecting 1 dimensional reinforcement elements), or a 3 dimensional reinforcement (such as a 3-dimensional grid). In other embodiments, the reinforcement is a medical grade textile.

The reinforced elastomeric matrix and/or composite mesh comprising degradable reticulatedelastomeric matrix can be made more functional for specific uses in various implantable devices by including or incorporating a reinforcement, e.g., fibers, into the degradable reticulatedcross-linked elastomeric urea-urethane matrix. In one embodiment elastomeric matrix is compressed. The enhanced functionalities that can be imparted by using a reinforcement include but are not limited to enhancing the ability of the device to withstand pull out loads associated with suturing during surgical procedures, the device's ability to be positioned at the repair site by suture anchors during a surgical procedure, and holding the device at the repair site after the surgery when the tissue healing takes place. In another embodiment, the enhanced functionalities provide additional load bearing capacities to the device during surgery in order to facilitate the repair or regeneration of tissues. In another embodiment, the enhanced functionalities provide additional load bearing capacities to the device, at least through the initial days following surgery, in order to facilitate the repair or regeneration of tissues. In another embodiment, the enhanced functionalities provide additional load bearing capacities to the device following surgery in order to facilitate the repair or regeneration of tissues. In one embodiment, the reinforcement used does not interfere with the matrix's capacity to accommodate tissue ingrowth and proliferation.

One way of obtaining enhanced functionalities is by incorporating a reinforcement, e.g., fibers, fiber meshes, wires and/or sutures, into the elastomeric matrix. Another exemplary way of obtaining enhanced functionalities is by reinforcing the matrix with at least one reinforcement. The incorporation of the reinforcement into the matrix can be achieved by various ways, including but not limited use of an adhesive such as silicone, polyurethanes, permanent polymers and preferably biodegradable polymers. Exemplary biodegradable polymers that can be used as adhesives include not limited to copolymers of polycaprolactone, polylactic acid, polyglycolic acid, acid d-, 1- and meso lactide and poly para-dioxanone, etc. or mixtures thereof. In another embodiment, biodegradable polymers that can be used as adhesives comprise copolymers of caprolactone with polylactic acid, polyglycolic acid, acid d-, 1- and meso lactide and poly para-dioxanone, etc. or mixtures thereof. Exemplary polyurethane that can be used as adhesives include not limited to polycarbonate polyurethanes, polysiloxane polyurethanes, poly(siloxane-co-ether)polyurethanes, polycarbonate polysiloxane polyurethanes, polycarbonate urea-urethanes, polycarbonate polysiloxane urea-urethanes and the like and their mixtures.

The adhesive can be applied between the reinforcement and elastomeric matrix and cured. In another embodiment, the adhesive can be applied either to reinforcement or the elastomeric matrix or both before being cured. The adhesive can be applied by dip or spray coating, painted with a brush, by use of customized coating fixtures that can lay down or deliver a thin layer of adhesive using blades with adjustable heights followed by transfer of the thin layer of adhesive on to the reinforcement or the elastomeric matrix. Or both. In one embodiment, the adhesive is a solution and the polymer content in the adhesive solution is from about 1% to about 40% by weight. In another embodiment, the polymer content in the adhesive solution is from about 1% to about 20% by weight. In another embodiment, the polymer content in the adhesive solution is from about 1% to about 10% by weight. In one embodiment, the adhesive does not contain any solvents. The solvent or solvent blend for the coating solution is chosen, e.g., based on the considerations discussed in the previous section (i.e., in the "Imparting Endopore Features" section). In one embodiment, the adhesive can be cured between 50° C. and 150° C. and in another embodiment between 60° C. and 120° C. In one embodiment, the adhesive can be cured between 10 minutes and 3 hours and in another embodiment between 15 minutes and 2 hours.

The adhesive can be applied between the reinforcement and elastomeric matrix by melt-bonding the adhesive the reinforcement and elastomeric matrix. In another embodiment, the adhesive can be applied either to reinforcement or the elastomeric matrix. In another embodiment, the adhesive may be applied by melting the film-forming adhesive polymer and applying the melted polymer through a die, in a process such as extrusion or coextrusion, as a thin layer of melted. In these embodiments, the melted polymer either coats the reinforcement or coats the elastomeric matrix macro surface but does not penetrate into the interior to any significant depth or bridges or plugs pores of that surface. Thus, the reticulated nature of portions of the elastomeric matrix removed from the macro surface, and portions of the elastomeric matrix's macro surface not in contact with the melted polymer, is maintained. Upon applying pressure to create contact between elastomeric matrix and reinforcement, cooling and solidifying, the melted polymer forms a layer of solid coating on the elastomeric matrix and the reinforcement and in the interface between them. In one embodiment, the processing temperature of the melted thermoplastic adhesive polymer is at least about 60° C. In another embodiment, the processing temperature of the melted thermoplastic adhesive polymer is at least above about 90° C. In another embodiment, the processing temperature of the melted thermoplastic adhesive polymer is at least above about 120° C. and in yet another embodiment, the processing temperature of the melted thermoplastic adhesive polymer is at least above about 140° C. The melt can be applied by extruding or coextruding or injection molding or compression molding or compressive molding the melt onto the degradable reticulatedelastomeric matrix.

Embodiments of the invention composite mesh comprising degradable reticulatedelastomeric include a "sandwich design" wherein the reinforcement can be incorporated between two layers of the elastomeric matrix, and an "open face sandwich design" wherein the medical grade textile is incorporated with a single layer of elastomeric matrix. In another embodiment, multiple layers of reinforcement and elastomeric matrix can be stacked in an alternating fashion and an adhesive can be used to incorporate the alternating layer. Without being bound by any particular theory, too little adhesive may prevent adequate bonding while too much adhesive may lad to partial or full clogging of the pores of the degradable reticulated elastomeric matrix or can also lead to loss of flexibility during delivery and placement.

The elastomeric matrix that incorporates the fibers into the degradable reticulatedcross-linked partially degradable and fully degradable elastomeric polycarbonate urea-urethane matrix can vary in its orientation. Orientation can occur during initial formation of foam, during reticulation, or during secondary processing that may occur after reticulation and thermal curing of the foam. The results of orientation are manifested by enhanced properties and/or enhanced performance in the direction of orientation. In one embodiment, a device made from a reinforced degradable reticulatedelastomeric matrix is positioned in the tissue being repaired in such a way that the enhanced properties and/or enhanced performance of the oriented matrix is aligned in the direction to resist the higher load bearing direction. Incorporation of the reinforcement may lead to enhanced performance of the matrix, which is superior to that which would be obtained by orienting the reinforced matrix in one or more directions.

The reinforcement can comprise mono-filament fiber, multi-filament yarn, braided multi-filament yarns, commingled mono-filament fibers, commingled multi-filament yarns, bundled mono-filament fibers, bundled multi-filament yarns, and the like. The reinforcement can comprise an amorphous polymer, semi-crystalline polymer, e.g., polyester or nylon, carbon, e.g., carbon fiber, bio-glass, glass, e.g., glass fiber, ceramic, cross-linked polymer fiber and the like or any mixture thereof. The fibers can be made from absorbable or non-absorbable materials. In one embodiment, the fiber reinforcement of the present invention is made from a biocompatible material(s).

In one embodiment, the reinforcement can be made from at least one non-absorbable material, such as a non-biodegradable or non-absorbable polymer. Examples of suitable non-absorbable polymers include but are not limited to polyesters, polyolefins and blends thereof as well as, polyamides; polycarbonates; polyoxymethylenes; polyimides; polyethers; epoxy resins; polyurethanes; and any mixture thereof.

In another embodiment, the reinforcement can be made preferably from at least one biodegradable, bioabsorbable or absorbable polymer. Examples of suitable absorbable polymers include but are not limited to aliphatic polyesters, e.g., homopolymers and copolymers of lactic acid, glycolic acid, lactide, glycolide, para-dioxanone, trimethylene carbonate, $\epsilon$-caprolactone and blends thereof. Further exemplary biocompatible polymers include film-forming bioabsorbable polymers such as aliphatic polyesters, poly(amino acids), copoly(ether-esters), polyalkylenes oxalates, polyamides, poly(iminocarbonates), polyorthoesters, polyoxaesters including polyoxaesters containing amido groups, polyamidoesters, polyanhydrides, polyphosphazenes, biomolecules, and any mixture thereof. Aliphatic polyesters, for the purpose of this application, include polymers and copolymers of lactide (which includes lactic acid d-, l- and meso lactide), $\epsilon$-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one, and any mixture thereof.

Such fiber(s)/yarn(s) can be made by melt extrusion, melt extrusion followed by annealing and stretching, solution spinning, electrostatic spinning, and other methods known to those in the art. Each fiber can be bi-layered, with an inner core and an outer sheath, or multi-layered, with inner core, an outer sheath and one or more intermediate layers. In bi- and multi-layered fibers, the core, the sheath or any layer(s) outside the core can comprise a degradable or dissolvable polymer. The fibers can be uncoated or coated with a coating that can comprise an amorphous polymer, semi-crystalline polymer, carbon, glass, ceramic, and the like or any mixture thereof.

The reinforcement can be made from carbon, glass, a ceramic, bioabsorbable glass, silicate-containing calcium-phosphate glass, or any mixture thereof. The calcium-phosphate glass, the degradation and/or absorption time in the human body of which can be controlled, can contain metals, such as iron, magnesium, sodium, potassium, or any mixture thereof.

In another embodiment, the 1-dimensional reinforcement and 2-dimensional reinforcement comprises intersecting 1 dimensional reinforcement elements comprises an amorphous polymer fiber, a semi-crystalline polymer fiber, a cross-linked polymer fiber, a biopolymer fiber, a collagen fiber, an elastin fiber, carbon fiber, glass fiber, bioabsorbable glass fiber, silicate-containing calcium-phosphate glass fiber, ceramic fiber, polyester fiber, nylon fiber, an amorphous polymer yarn, a semi-crystalline polymer yarn, a cross-linked polymer yarn, a biopolymer yarn, a collagen yarn, an elastin yarn, carbon yarn, glass yarn, bioabsorbable glass yarn, silicate-containing calcium-phosphate glass yarn, ceramic yarn, polyester yarn, nylon yarn, or any mixture thereof.

The reinforcement can be incorporated into the degradable reticulatedelastomeric matrix in different patterns. In one embodiment, the reinforcement is placed along the entire surface or the contact surface of the elastomeric matrix. In one embodiment, the reinforcement is placed along the border of the device, maintaining a fixed distance from the device's edges. In another embodiment, the reinforcement is placed along the border of the device, maintaining a variable distance from the device's edges. In another embodiment, the reinforcement is placed along the perimeter, e.g., circumference for a circular device, of the device, maintaining a fixed distance from the device's edges. In another embodiment, the reinforcement is placed along the perimeter of the device, maintaining a variable distance from the device's edges. In another embodiment, the reinforcement is present as a plurality of parallel and/or substantially parallel 1 dimensional reinforcement elements, e.g., as a plurality of parallel lines such as parallel fibers. In another embodiment, the reinforcement is placed as a 2- or 3 dimensional reinforcement grid in which the 1 dimensional reinforcement elements cross each other's path. In another embodiment, the reinforcement is placed as a 2- or 3 dimensional reinforcement grid in which the 1 dimensional reinforcement elements cross each other's path and there is no special reinforcement along the perimeter or the border. The grid can have one or multiple reinforcement elements. In 2- or 3 dimensional reinforcement grid embodiments, the elements of the reinforcement can be arranged in geometrically-shaped patterns, such as square, rectangular, trapezoidal, triangular, diamond, parallelogram, circular, elliptical, pentagonal, hexagonal, and/or polygons with seven or more sides. The reinforcement elements comprising a reinforcement grid can all be of the same shape and size or can be of different shapes and sizes. The reinforcement elements comprising a reinforcement grid can additionally include border, perimeter and/or parallel line elements. The performance or properties of the reinforcement grid incorporates the reinforcement into the matrix and the thus-reinforced matrix depends on the inherent properties of the reinforcement as well as the pattern, geometry and number of elements of the grid.

In other embodiments, the clearance or spacing between reinforcement elements, such as the clearance between adjacent linear reinforcement elements, can be from about 0.25 mm to about 20 mm in one embodiment, or from about 0.5 mm to about 15 mm in another embodiment. In other embodiments, the clearance between reinforcement elements is substantially the same between elements. In other embodiments, the clearance between reinforcement elements differs between different elements. In other multi-dimensional reinforcement embodiments, the clearance between reinforcement elements in one dimension is independent of the clearance(s) between reinforcement elements in any other dimension.

The diameter of a reinforcement element having a substantially circular cross-section can be from about 0.03 mm to about 0.50 mm in one embodiment, or from about 0.07 mm to about 0.30 mm in another embodiment, or from about 0.05 mm to about 1.0 mm in another embodiment, or from about 0.03 mm to about 1.0 mm in another embodiment. In another embodiment, the diameter of a reinforcement element having a substantially circular cross-section can be equivalent to a USP suture diameter from about size 8 0 to about size 0 in one embodiment, from about size 8 0 to about size 2 in another embodiment, from about size 8 0 to about size 2-0 in another embodiment.

The reinforcement layout or the distribution and pattern of reinforcement elements, e.g., fibers or sutures or grid in the matrix will depend on design requirement and/or the application for which the device will be used.

In one embodiment, the incorporation of the reinforcement into the matrix can be achieved by various ways, including but not limited to stitching, sewing, weaving and knitting. In one embodiment, the attachment of the reinforcement to the matrix can be through a sewing stitch. In another embodiment, the attachment of the reinforcement to the matrix can be through a sewing stitch that includes an interlocking feature. In another embodiment, the incorporation of the reinforcement into the matrix can be achieved by foaming of the elastomeric matrix ingredients around a pre-fabricated or pre-formed reinforcement element made from a reinforcement and reticulating the composite structure thus-formed to create an intercommunicating and interconnected pore structure. In one embodiment, the reinforcement used does not interfere with the matrix's capacity to accommodate tissue in-growth and proliferation. In an embodiment where sewing is used to incorporate the reinforcement into the matrix, the pitch of the stitch, i.e., the distance between successive stitches or attachment points within the same line, is from about 0.25 mm to about 4 mm in one embodiment or from about 1 mm to about 3 mm in another embodiment.

For a device of this invention comprising a reinforced degradable reticulated elastomeric matrix, the maximum dimension of any cross-section perpendicular to the device's thickness is from about 0.25 mm to about 100 mm in one embodiment. In another embodiment, the maximum thickness of the device is from about 0.25 mm to about 20 mm. The composite mesh comprising degradable reticulated elastomeric matrix or composite surgical mesh comprising degradable reticulated elastomeric matrix can be made available in various sizes. In certain embodiments of the composite mesh device comprising degradable reticulated elastomeric matrix or composite surgical mesh device comprising degradable reticulated elastomeric matrix can range from about 0.5 mm to about 4 mm in thickness and may be in any two-dimensional or three-dimensional shape. Exemplary embodiments of a two-dimensional shape may include regular and irregular shapes, such as, for example, triangular, rectangular, circular, oval, elliptical, trapezoidal, pentagonal, hexagonal and irregular configurations, including one that corresponds to the shape of the defect, and other shapes. Exemplary embodiments of a three-dimensional shape may include, plugs, cylinders, tubular structures, stent-like structures, and other configurations, including one that corresponds to the contours of the defect, and other configurations. The device may have a major axis having a length between about 2 cm to about 50 cm. The device may be in a square shape with a side having a length between about 2 cm to about 50 cm.

In one embodiment, the implantable device and/or its reinforcement can be coated with one or more bioactive molecules, such as the platelet rich plasma, proteins, collagens, elastin, entactin-1, fibrillin, fibronectin, cell adhesion molecules, matricellular proteins, cadherin, integrin, selectin, H-CAM superfamilies, and the like described in detail herein.

EXAMPLES

Example 1

Synthesis and Properties of Degradable Reticulated Elastomeric Matrix Containing Polycaprolactone Polyol A reticulated partially resorbable elastomeric matrix was made by the following procedure: The aromatic isocyanate MONDUR 1488 (from Bayer Material Science) was used as the isocyanate component. MONDUR 1488 is a liquid at 25° C. MONDUR 1488 contains 4,4'-diphenylmethane diisocyanate (4,4 MDI) and 2,4'-diphenylmethane diisocyanate (2,4 MDI) and has an isocyanate functionality of about 2.2 to 2.3. The ratio of (4,4 MDI) to 2,4-MDI) is approximately 2.5:1. A polycaprolactone diol with a molecular weight of about 2,000 Daltons was used as the polyol component and was a solid at 25° C. Distilled water was used as the blowing agent. The catalysts used were the amines triethylene diamine (33% by weight in dipropylene glycol; DABCO 33LV from Air Products) and bis(2-dimethylaminoethyl)ether (23% by weight in dipropylene glycol; NIAX A-133 from Momentive Performance Chemicals). Silicone-based surfactants TEGOSTAB BF 2370, TEGOSTAB B5055, AND TEGOSTAB B8300 (from Evonik Degussa) were used for cell stabilization. A cell-opener was used (ORTEGOL 501 from Evonik Degussa). Glycerine (99.7% USP Grade) and 1,4-butanediol (99.75% by weight purity, from Lyondell) were added to the mixture as, respectively, a cross-linking agent and a chain extender. The proportions of the ingredients that were used is given in Table A below.

TABLE A

| Ingredient | Parts by Weight |
| --- | --- |
| Polyol Component | 100.00 |
| Isocyanate Component | 45.58 |
| Isocyanate Index | 1.00 |
| Cell Opener | 3.00 |
| Distilled Water | 1.60 |
| BF2370 Surfactant | 1.20 |
| B8300 Surfactant | 0.60 |
| B5055 Surfactant | 0.60 |
| 33LV Catalyst | 0.40 |
| A-133 Catalyst | 0.15 |
| Glycerine | 1.00 |
| 1,4-Butanediol | 1.50 |

The isocyanate index, is the mole ratio of the number of isocyanate groups in a formulation available for reaction to the number of hydroxyl groups in the formulation that are able to react with those isocyanate groups, e.g., the reactive groups of diol(s), polyol component(s), chain extender(s), water and the like, when present. As seen above, the isocyanate index was low and equal to 1.0; a stoichiometrically balanced ratio of isocyanate and hydroxyl groups was used to prevent formation of isocyanurate linkages, biuret linkages and allophanate linkages. The isocyanate component of the formulation was placed into the component A metering system of an Edge Sweets Bench Top model urethane mixing apparatus and maintained at a temperature of about 20-25° C.

The polyol was liquefied at about 70° C. in an oven and combined with the cell opener in the aforementioned proportions to make a homogeneous mixture. This mixture was placed into the component B metering system of the Edge Sweets apparatus. This polyol component was maintained in the component B system at a temperature of about 65-70° C.

The remaining ingredients consisting of the chain extender, cross-linker, cell opener, catalysts, surfactants from Table 1 were mixed in the aforementioned proportions into a single homogeneous batch and placed into the component C metering system of the Edge Sweets apparatus. This component was maintained at a temperature of about 20-25° C. During foam formation, the ratio of the flow rates, in grams per minute, from the supplies for component A: component B: component C was about 5:10:1.

Figure 2:
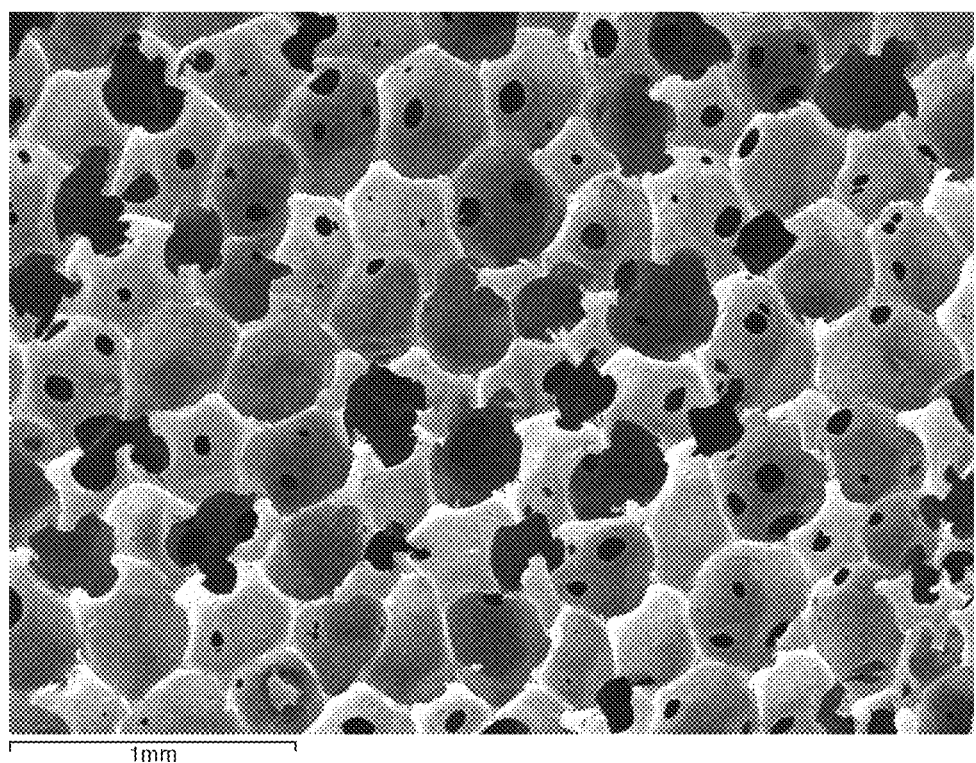
FIG. 2 presents electron micrographs of exemplary reticulated matrix of the invention.

The above components were combined in a continuous manner in the 250 cc mixing chamber of the Edge Sweets apparatus that was fitted with a 10 mm diameter nozzle placed below the mixing chamber. Mixing was promoted by a high-shear pin-style mixer operating in the mixing chamber. The mixed components exited the nozzle into a rectangular cross-section release-paper coated mold. Thereafter, the foam rose to substantially fill the mold. The resulting mixture began creaming about 10 seconds after contacting the mold and was at full rise within 120 seconds. The top of the resulting foam was trimmed off and the foam was allowed to cure at ambient temperature for 24 hours. FIG. 2 is a scanning electron micrograph (SEM) image of un-reticulated degradable elastomeric matrix 1 after foaming and ambient curing. It demonstrates a collection of cells whose walls though showing some pores do not show that the cells are interconnected via the open pores. It is porous with a few open pores but does not have the inter-connected natutre or possess the possibility of inter communication between the cells that are far from each other.

Following curing, the sides and bottom of the foam block were trimmed off then the foam was placed into a reticulator device comprising a pressure chamber, the interior of which was isolated from the surrounding atmosphere. The pressure in the chamber was reduced so as to remove substantially all the air in the cured foam. A mixture of hydrogen and oxygen gas, present at a molar ratio of 2.3:1 of Hydrogen to Oxygen, sufficient to support combustion, was introduced or charged into the chamber. A mixture of hydrogen and oxygen gas, present at a ratio of 2.3:1 $H_2:O_2$, sufficient to support combustion, was charged into the chamber. The pressure in the chamber was maintained above atmospheric pressure for a sufficient time to ensure gas penetration into the foam. The gas in the chamber was then ignited by a spark plug and the ignition exploded the gas mixture within the foam. To minimize contact with any combustion products and to cool the foam, the resulting combustion gases were removed from the chamber and replaced with about 25° C. nitrogen immediately after the explosion. Then, the above-described reticulation process was repeated one more time. Without being bound by any particular theory, the explosions were believed to have at least partially removed or more likely substantially removed many of the cell walls or "windows" between adjoining cells in the foam, thereby creating inter-connected cells via open pores and leading to a reticulated elastomeric matrix structure.

Figure 3:
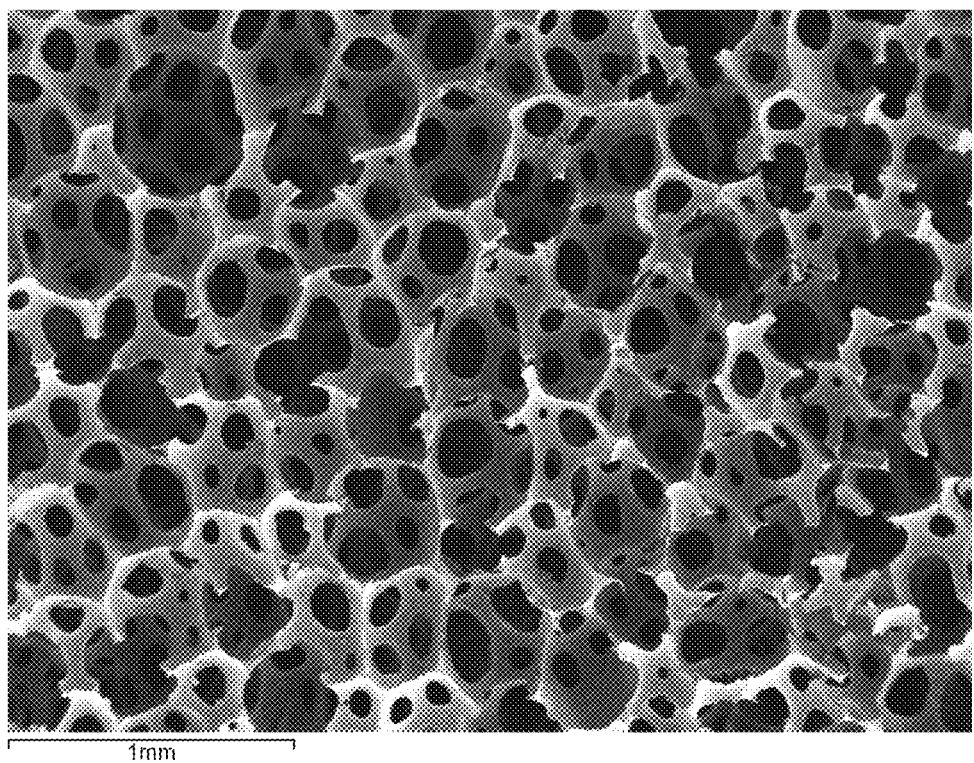
FIG. 3 presents electron micrographs of an unreticulated matrix

The average cell diameter or other largest transverse dimension of Degradable Reticulated Elastomeric Matrix 1, as determined from optical microscopy observations, was about 379 μm. FIG. 3 is a scanning electron micrograph (SEM) image of Reticulated Elastomeric Matrix 1 demonstrating, e.g., the network of cells interconnected via the open pores therein and the communication and interconnectivity thereof. The cells from different regions in the scans are interconnected and can communicate with each other for fluid flow or tissue ingrowth; the network of interconnected cells creates a continuous void phase. The scale bar at the bottom edge of FIG. 10 corresponds to about 1000 μm.

The following tests were carried out on the thus-formed Degradable Reticulated Elastomeric Matrix, obtained from reticulating the foam, using test methods based on ASTM Standard D3574. Bulk density was measured using Reticulated Elastomeric Matrix 1 specimens of dimensions 5.0 cm×5.0 cm×2.5 cm. The post-reticulation density was calculated by dividing the weight of the specimen by the volume of the specimen. A density value of 3.2 lbs/ft$^3$ (0.051 g/cc) was obtained.

Tensile tests were conducted on Reticulated Elastomeric Matrix 1 specimens that were cut either parallel to or perpendicular to the foam-rise direction. The dog-bone shaped tensile specimens were cut from blocks of reticulated elastomeric matrix. Each test specimen measured about 1.25 cm thick, about 2.54 cm wide, and about 14 cm long. The gage length of each specimen was 3.5 cm and the gage width of each specimen was 6.5 mm. Tensile properties (tensile strength and elongation at break) were measured using an INSTRON Universal Testing Instrument Model 3342 with a cross-head speed of 50 cm/min (19.6 inches/min). The average post-reticulation tensile strength parallel to the foam-rise direction was determined to be about 43 psi (30,230 kg/m$^2$). The post-reticulation elongation to break parallel to the foam-rise direction was determined to be about 246%. The average post-reticulation tensile strength perpendicular to the foam-rise direction was determined to be about 31 psi (21,790 kg/m$^2$). The post-reticulation elongation to break perpendicular to the foam-rise direction was determined to be about 278%.

Compressive tests were conducted using Reticulated Elastomeric Matrix 1 specimens measuring 5.0 cm×5.0 cm×2.5 cm. The tests were conducted using an INSTRON Universal Testing Instrument Model 1122 with a cross-head speed of 1 cm/min (0.4 inches/min). The post-reticulation compressive strength at 50% compression, parallel to the foam-rise direction, was determined to be about 0.4 psi (281 kg/m$^2$).

The static recovery of Reticulated Elastomeric Matrix 1 was measured by subjecting cylindrcular specimens, each 12 mm in diameter and 6 mm in thickness, to a 50% uniaxial compression in the foam-rise direction using the standard compressive fixture in a Q800 Dynamic Mechanical Analyzer (TA Instruments, New Castle, Del.) for 120 minutes followed by 120 minutes of recovery time. The time required for recovery to 90% of the specimen's initial thickness of 6 mm ("t-90%") was measured and the average determined to be 6 seconds. The time required for recovery to 90% of the specimen's initial thickness of 6 mm ("t-95%") was measured and the average determined to be 44 seconds.

Fluid, e.g., liquid, permeability through of reticulated degradable elastomeric was measured in the foam-rise direction using the method described in Example 2. and was determined to have an average of 345 Darcy. The thermal reticulation led to higher permeability brought about by the presence of a continuous void phase which itself is a result the network of cells interconnected via the open pores therein and the subsequent communication and interconnectivity. The permeability of the unreticulated foam matrix was below 5 Darcy.

Example 2

Synthesis and Properties of Degradable Reticulated Elastomeric Matrix Containing Polycaprolactone Polyol A reticulated partially resorbable elastomeric matrix was made by the following procedure: The aromatic isocyanate MONDUR 1488 (from Bayer Material Science) was used as the isocyanate component. MONDUR 1488 is a liquid at 25° C. MONDUR 1488 contains 4,4'-diphenylmethane diisocyanate (MDI) and 2,4'-MDI and has an isocyanate functionality of about 2.2 to 2.3. A polycaprolactone diol, POLY-T220 from Arch Chemicals, with a molecular weight of about 2,000 Daltons, was used as the polyol component and was a solid at 25° C. Distilled water was used as the blowing agent. The catalysts used were the amines triethylene diamine (33% by weight in dipropylene glycol; DABCO 33LV from Air Products) and bis(2-dimethylaminoethyl)ether (23% by weight in dipropylene glycol; NIAX A-133 from Momentive Performance Chemicals). Silicone-based surfactants TEGOSTAB BF 2370, TEGOSTAB B5055, AND TEGOSTAB B8300 (from Evonik Degussa) were used for cell stabilization. A cell-opener was used (ORTEGOL 501 from Evonik Degussa). Glycerine (99.7% USP Grade) and 1,4-butanediol (99.75% by weight purity, from Lyondell) were added to the mixture as, respectively, a cross-linking agent and a chain extender. The proportions of the ingredients that were used is given in Table B below.

TABLE B

| Ingredient | Parts by Weight |
|---|---|
| Polyol Component | 100.00 |
| Isocyanate Component | 45.58 |
| Isocyanate Index | 1.00 |
| Cell Opener | 3.00 |
| Distilled Water | 1.60 |
| BF2370 Surfactant | 1.20 |
| B8300 Surfactant | 0.60 |
| B5055 Surfactant | 0.60 |
| 33LV Catalyst | 0.40 |
| A-133 Catalyst | 0.15 |
| Glycerine | 1.00 |
| 1,4-Butanediol | 1.50 |

The isocyanate index, is the mole ratio of the number of isocyanate groups in a formulation available for reaction to the number of hydroxyl groups in the formulation that are able to react with those isocyanate groups, e.g., the reactive groups of diol(s), polyol component(s), chain extender(s), water and the like, when present. As seen above, the isocyanate index was low and equal to 1.0; a stoichiometrically balanced ratio of isocyanate and hydroxy groups was used to prevent formation of isocyanurate linkages, biuret linkages and allophanate linkages.

The polyol component was liquefied at 70° C. in a circulating-air oven, and 300 g thereof was weighed out into a polyethylene cup. The remaining ingredients excluding the isocyante and consisting of the chain extender, cross-linker, cell opener, catalysts, surfactants from Table 2 were added to the polyol component at their proportional weights based on the aforementioned formulation. These components were mixed together with a pin style high sheer mixer attached to a motor for 60 seconds.

The required amount of isocyante was weighed into a polyethylene cup and then added to the polyol mixture during high speed mixing. The total formulation was mixed vigorously with the drill mixer as described above for 10 seconds then poured into a cardboard box with its inside surfaces covered by polyethylene coated paper. The foaming profile was as follows: 10 seconds mixing time, 25 seconds cream time, and 90 seconds rise time. The block was allowed to cure for 24 hours at ambient conditions.

The average cell diameter or other largest transverse dimension of Degradable Reticulated Elastomeric Matrix, as determined from optical microscopy observations, was about 759 μm. The following tests were carried out on the thus-formed Degradable Reticulated Elastomeric Matrix, obtained from reticulating the foam, using test methods based on ASTM Standard D3574. Bulk density was measured using Degradable Reticulated Elastomeric Matrix specimens of dimensions 5.0 cm×5.0 cm×2.5 cm. The post-reticulation density was calculated by dividing the weight of the specimen by the volume of the specimen. A density value of 3.60 (±0.12) lbs/ft$^3$ (0.058 g/cc) was obtained.

Fluid, e.g., liquid, permeability through of un-reticulated degradable elastomeric matrix 1 after foaming and ambient curing was measured in the foam-rise direction using a Porous Materials Inc. Automated Liquid Permeameter (Model LP-101-A, Serial No. 2162006-1489). The cylindrical un-reticulated degradable elastomeric matrix specimens tested were between 7.0-7.0 mm in diameter and 13 mm in length or thickness. The sample was crushed by putting one end of the cylindrical test specimen on a flat surface, placing a flat steel plate on top of the other cylindrical end and pushing the upper flat steel plate vertically down and bringing it up at least 5 times. The upper plate was pushed all the way down till the unreticulated matrix was flat. After the crushing operation, A flat end of a specimen was placed in the center of a Stainless steel sample holder with opening diameter of 6.37 mm that was placed at the bottom of the Liquid Permeameter apparatus. To measure liquid permeability, water was allowed to extrude upward, driven by pressure from a fluid reservoir, from the specimen's end through the specimen along its axis. The operations associated with permeability measurements were fully automated and controlled by a Capwin Automated Liquid Permeameter (version 6.71.92) which, together with Microsoft Excel software, performed all the permeability calculations. The permeability of Reticulated Elastomeric Matrix using water was determined to be 15 Darcy in the foam-rise direction.

Following curing, the sides and bottom of the foam block were trimmed off then the foam was placed into a reticulator device comprising a pressure chamber, the interior of which was isolated from the surrounding atmosphere. The pressure in the chamber was reduced so as to remove substantially all the air in the cured foam. A mixture of hydrogen and oxygen gas, present at a ratio of 2.3:1 $H_2$:$O_2$, sufficient to support combustion, was charged into the chamber. The pressure in the chamber was maintained above atmospheric pressure for a sufficient time to ensure gas penetration into the foam. The gas in the chamber was then ignited by a spark plug and the ignition exploded the gas mixture within the foam. To minimize contact with any combustion products and to cool the foam, the resulting combustion gases were removed from the chamber and replaced with gaseous nitrogen immediately after the explosion. Then, the above-described reticulation process was repeated one more time. Without being bound by any particular theory, the explosions were believed to have at least partially removed or more likely substantially removed many of the cell walls or "windows" between adjoining cells in the foam, thereby creating inter-connected cells via open pores and leading to a reticulated elastomeric matrix structure and this process is known as thermal reticulation.

The average cell diameter or other largest transverse dimension of Degradable Reticulated Elastomeric Matrix is expected to be about the same (759 μm) as the unreticulated matrix; and the post-reticulation density was 3.60 lbs/ft³ (0.058 g/cc).

Fluid, e.g., liquid, permeability using water through Reticulated Degradable Elastomeric Matrix was measured in the foam-rise direction and was determined to have an average of 619 Darcy. The permeability increased by about 45 times from the unreticulated foam matrix that was crushed to the thermally reticulated biodegradable matrix showing that crushing did not produce high permeability while thermal reticulation led to much higher permeability brought about by the presence of a continuous void phase which itself is a result the network of cells interconnected via the open pores therein and the subsequent communication and interconnectivity.

The glass transition of the degradable elastomeric matrix was measured by a temperature ramp between –80 C to 180 C at 2° C./minute using a Q 20 DSC (TA Instruments, New Castle, Del.). The sample weights were about 6 mg.

Resilient recovery time of the scaffold was measured by Dynamical Mechanical Analyzer (DMA Q 800 made by TA Instruments) where the specimen was held under 75% compression for 10 minutes before the load is removed to report 90% recovery times. The 90% recovery time following 75% compression for 10 minutes is 4 seconds. In another case, 90% recovery time following 50% compression for 2 hours is 5 seconds.

Example 3

Synthesis and Properties of Degradable Reticulated Elastomeric Matrix Containing Polycaprolactone/Polyglycolide Copolymer Polyol, Polycaprolactone/Polylactide Copolymer Polyol and Polycaprolactone/d-l Lactide Copolymer Polyol A number of reticulated partially resorbable reticulated elastomeric matrices using different caprolactone copolymer polyols (custom prepared by Bezwada Biomedical, NJ) were made by the procedure described in Example 2. The proportions of the ingredients that were used for the various formulations and the measured T=0 properties (using methods described in Examples 1 and 2) are provided in Table C below:

TABLE C

| Formulation | MDI-PCL/PGA | | MDI-PCL/PDLA | MDI-PCL/PLLA | |
| --- | --- | --- | --- | --- | --- |
| | Form C1 | Form C2 | Form C3 | Form C4 | Form C5 |
| Polyol Composition | Caprolactone/Glycolide 75/25 mole % | | Caprolactone/D,L-Lactide 75/25 mole % | Caprolactone/L-Lactide 80/20 mole % | |
| Polyol Mol. Wt. | About 2500 | | About 1980 | About 1963 | |
| Polyol | 100.00 | 100.00 | 100.00 | 100.00 | 100.00 |
| Aromatic Isocyante (MONDUR 1488) | 52.0 | 45.5 | 60.1 | 60.2 | 47.3 |
| Glycerin (external cross-linker) | 1.20 | 1.00 | 3.00 | 3.00 | 1.00 |
| Water | 2.00 | 2.00 | 2.00 | 2.00 | 2.00 |
| 1,4 BDO (chain xtender) | 1.50 | 0.00 | 1.50 | 1.50 | 0.00 |
| Cell Opener | 3.00 | 2.00 | 2.00 | 2.00 | 2.00 |
| Surfactant 1 | 0.50 | 1.00 | 0.50 | 0.50 | 0.50 |
| Surfactant 2 | 1.50 | 1.00 | 1.00 | 1.00 | 1.00 |
| Surfactant 3 | 1.50 | 1.00 | 1.00 | 1.00 | 1.00 |
| Catalyst 1 | 0.45 | 0.50 | 0.50 | 0.50 | 0.50 |
| Catalyst 2 | 0.15 | 0.25 | 0.15 | 0.15 | 0.15 |
| Properties at T = 0. | | | | | |
| % Hard Segment | 32.59% | 29.22% | 36.98% | 37.02% | 30.17% |
| Density (pcf) | 4.1 (0.17) | 4.2 (0.35) | 3.8 (0.18) | 4.3 (0.89) | 4.2 (0.35) |
| Cell Size (μm) | 1101 (174) | 720 (127) | 352 (51) | 509 (80) | 728 (89) |
| Permeability (Darcy) | 328 (8) | — | 632 (39) | 259 (96) | 17 (1) |
| Compressive Strength @ 50% strain (psi) | 0.4 (0.07) | — | 1.7 (0.76) | 2.5 (1.41) | 0.8 (0.15) |
| Tensile Max Load (N) | 12 (3) | 12 (4) | 17 (5) | 20 (4) | 13 (2) |
| Tensile Stress (psi) | 27.6 (6.9) | 27.6 (9.2) | 39.1 (11.5) | 46 (9.2) | 29.9 (4.6) |
| Elongation (%) | 323 (30) | 191 (33) | 205 (46) | 159 (20) | 341 (45) |
| DSC Analysis Tg (° C.) | −8 (2) | −15 (3) | 2 (1) | −8 (1) | −15 (0) |

Standard Deviations are provided in parenthesis. The high values of elongation to break (>150%) for all formulations demonstrate the elastomeric nature of these scaffolds.

The resorbable reticulated elastomeric matrices were subjected to in vitro aging. The in-vitro degradation characteristics were monitored by submerging scaffold test articles in a simulated in-vivo environment—Sorensen Buffer (phosphate buffer) with controlled pH (7.3+0.3) maintained at physiological or body temperature (37+0.2° C.). An accelerated in-vitro degradation process was developed to obtain an early estimate for the degradation profile. The use of temperatures higher than 37° C. has been reported to accelerate the in-vitro degradation process as long as the higher temperatures do not change the underlying morphology. A temperature of 60° C. was chosen for accelerated degradation. This temperature is expected to accelerate the degradation rates by approximately 5× to 7× due to the 20° C. difference between real time (37° C.) and accelerated conditions; the generally accepted theory is that a 10° C. increase in temperature doubles the rate of degradation rate reaction for thermoplastics and cross-linked structures degrade somewhat differently than thermoplastics.

At T=0, tensile load and elongation for MDI-PCL/PGA with 1.2 parts Glycerin and 1.5 parts BDO (Form C1) is 12N and 323% and drops to 0 for both load and elongation between 12 to 16 months in-vitro exposure at 37° C.

At T=0, tensile load and elongation for MDI-PCL/PGA with 1.0 parts Glycerin and 0 parts BDO (Form C2) is 12N and 191%. After 14 days in-vitro exposure at 60° C., tensile load drops to 9 N and elongation drops to 118% is and after 4 weeks in-vitro exposure at 60° C., both load and elongation drops to 0. Acknowledging the in vitro degradation acceleration factor (around 5× to 7×) between 37° C. and 60° C., lowering of chain extender and external cross-linker still speeded up the in vitro degradation rate for MDI-PCL/PGA reticulated matrix formulation.

At T=0, tensile load and elongation for MDI-PCL/PLLA with 3.0 parts Glycerin and 1.5 parts BDO (Form C4) is 20N and 159% and after 12 month in-vitro exposure at 37° C., the tensile load drops to 11N and elongation drops to 162%.

At T=0, tensile load and elongation for PCL/PLLA with 1.0 parts Glycerin and 0 parts BDO (Form C5) is 13N and 341%. After t=3 months in-vitro at 60° C., tensile load and elongation drops to 2 N and 25%, and after 4 months in-vitro at 60° C., both tensile load and elongation drops to 0. Acknowledging the in vitro degradation acceleration factor between 37° C. and 60° C., lowering of chain extender and external cross-linker still speeded up the in vitro degradation rate for MDI-PCL/PLLA reticulated matrix formulation.

Based on accelerated in-vitro data, the degradation times of for MDI-PCL/PGA with 1.0 parts Glycerin and 0 parts BDO (Form C2) matrix is expected to be 6 to 9 months for PCL/PLLA with 1.0 parts Glycerin and 0 parts BDO (Form C5) matrix is expected to be 12 to 15 months.

Degradation products (obtained for PCL/PGA-MDI (Form C2) and from PCL/PLA-MDI (Form C5) matrices subjected to accelerated in-vitro conditions) were analyzed using GC/MS (at Jirdi Labs, MA) and the degradation products were found to be biocompatible and the degradation products were as expected based on the starting matrix compositions and caprolactone copolymer polyols.

Small Angle X-ray (SAXS) measurements of partially degradable reticulated elastomeric matrices Form C2 and Form C5 conducted at Virginia Tech (Blacksburg, Va.) showed that the hard segment domains were below 100 angstroms (° A) and it complies with the generally reported measurement of hard segment observed in other polyester based polyurethanes. These are small particle sizes and with low solid concentrations in high void volume matrix (about 30 to 40% hard segment out of less than 5% solid in >90 or 95% void matrix), the remaining hard segments will erode or bio-erode away in a biocompatible manner from implantation site after the soft segments have degraded away. Or these small particle sizes is not expected to cause any bio-compatibility issue even if they stay at the original wound site. The impact of the low amount of residual MDI-based hard segments dispersed over the original implant space and its very low domain size are expected to be minimal on the biocompatibility of the residual scaffold and the final tissue remodeling.

Resilient recovery time of the scaffold was measured by Dynamical Mechanical Analyzer (DMA Q 800 made by TA Instruments) where the specimen was held under 75% compression for 10 minutes before the load is removed to report 90% recovery times. The 90% recovery time following 75% compression for 10 minutes for Form C2 PCL/PGA-MDI is 5 minutes and for Form C5 PCL/PLA-MDI is 9 minutes.

Example 4

Synthesis and Properties of Degradable Reticulated Elastomeric Matrix Containing Polycaprolactone and H12 MDI A reticulated partially resorbable reticulated elastomeric matrices using caprolactone polyol and H12MDI was made by the procedure described in Example 2. The proportions of the ingredients that were used for the various formulations and the measured T=0 properties (using methods described in Examples 1 and 2) are provided in Table D below:

TABLE D

| Formulation | Form C6 |
| --- | --- |
| Polyol Composition | Polycaprolactone |
| Polyol Mol. Wt. | 2000 |
| Polyol | 100.00 |
| H12 MDI | 74 |
| Glycerin (external cross-linker) | 3.00 |
| Water | 3.00 |
| 1,4 BDO (chain extender) | 0.0 |
| Cell Opener | |
| Surfactant 1 | 2.00 |
| Surfactant 2 | 2.00 |
| Surfactant 3 | |
| Catalyst 1 | 3.00 |
| Catalyst 2 | 2.50 |
| Catalyst 3 | 3.00 |
| Catalyst 4 | 2.50 |
| Properties at T = 0. | |
| % Hard Segment | 37.0% |
| Density (pcf) | 3.8 (0.18) |
| Cell Size (um) | 352 (51) |
| Permeability (Darcy) | 632 (39) |
| Compressive Strength @ 50% strain (psi) | 1.7 (0.76) |
| Tensile Max Load (N) | 17 (5) |
| Tensile Stress (psi) | 39.1 (11.5) |
| Elongation (%) | 205 (46) |
| DSC Analysis Tg (° C.) | 2 (1) |

Standard Deviations are provided in parenthesis. The high values of elongation to break (>150%) demonstrate the elastomeric nature of the scaffold.

The resorbable reticulated elastomeric matrices were subjected to in vitro aging at physiological pH of about 7.3 and at normal physiological temperature of 60° C. as described in Example 3.

At T=0, tensile load and elongation for H12MDI-PCL with 3.0 parts Glycerin and 0 parts BDO (Form C6) is 14 N and 130% and after 5 month in-vitro exposure at 60° C., the tensile load and elongation drops to 0.6 N and 29% showing degradation for the formulation.

Example 5

Synthesis and Properties of Degradable Reticulated Elastomeric Matrix Containing Polycaprolactone/Polyglycolide Copolymer Polyol and Two Degradable Aromatic Isocyanates Two reticulated resorbable reticulated elastomeric matrices using polycaprolactone/polyglycolide copolymer polyol and Two Degradable Aromatic isocyanates were made by the procedure described in Example 2. The proportions of the ingredients that were used for the various formulations and the measured T=0 properties (using methods described in Examples 1 and 2) are provided in Table E below:

TABLE E

| Formulation | Form C7 | Form C8 |
|---|---|---|
| Polyol | Caprolactone/Glycolide 75/25 mole % Polyol | |
| Polyol Mol. Wt. | 2602 | 2602 |
| Polyol | 100 | 100 |
| Aromatic Degradable Isocyante | PGA RSDI 159.1 | PLA RSDI 178.7 |
| Glycerin (external cross-linker) | 1.50 | 1.50 |
| Water | 4.00 | 4.00 |
| 1,4 BDO (chain xtender) | — | — |
| Cell Opener | — | — |
| Surfactant 1 | 1.00 | 1.00 |
| Surfactant 2 | 1.00 | 1.50 |
| Surfactant 3 | 1.00 | 1.50 |
| Catalyst 1 | 1.00 | 1.00 |
| Catalyst 2 | 0.60 | 0.60 |
| Catalyst 3 | 0.60 | 0.60 |
| Properties at T = 0. | | |
| % Hard Segment | 59.54% | 62.15% |
| Density (pcf) | 3.8 (3.05) | 3.9 (0.15) |
| Cell Size (um) | 2387 (407) | 1028 (173) |
| Permeability (Darcy) | 971 (284) | 427 (70) |
| Compressive Stress at 50% strain (psi) | 8.2 (3.96) | 2.9 (0.32) |
| Tensile Max Load (N) | 24 (4) | 25 (4) |
| Tensile Stress (psi) | 55.2 (9.2) | 57.5 (9.2) |
| Elongation (%) | 159 (15) | 396 (57) |
| DSC Analysis Tg (° C.) | −15 (1) | 14 (5) |

Standard Deviations are provided in parenthesis. The high values of elongation to break (>150%) for all formulations demonstrate the elastomeric nature of these scaffolds.

Resorbable Segment Diisocyanates (RSDIs) based on PGA and PLA were made by Bezwada Biomedical and were termed as PGA-PGA RSDI (Di ethylene glycol diglycolate diisocyanate) and PLA RSDI (Di ethylene glycol dilactide diisocyanate). PGA RSDI. Molecular Formula: $C_{22}H_{20}N_2O_9$ and PLA RSDI Molecular Formula: $C_{24}H_{24}N_2O_9$.

The resorbable reticulated elastomeric matrices were subjected to in vitro aging at physiological pH of about 7.3 and at normal physiological temperature of 37° C. as described in Example 3.

At T=0, tensile load and elongation for PGA RSDI is 24N and 159%, after t=6 months in-vitro exposure at 37° C., tensile load and elongation dropped to 0N and 1% showing complete in vitro degradation.

At T=0, tensile load and elongation for PLA RSDI is 25N and 396%, after t=6 months in-vitro exposure at 37° C., tensile load and elongation dropped to 0.3 N and 139% showing substantial in vitro degradation.

Example 6

Synthesis and Properties of Degradable Reticulated Elastomeric Matrix Containing Polycaprolactone/Polyglycolide Copolymer Polyol A reticulated partially resorbable elastomeric matrix was made by the following procedure: The aromatic isocyanate MONDUR MQL (from Bayer Material Science) was used as the isocyanate component. MONDUR MQL is a liquid at 25° C. MONDUR MQL contains 4,4'diphenylmethane diisocyanate (4,4 MDI) and 2,4'-diphenylmethane diisocyanate (2,4 MDI) and has an isocyanate functionality of about 2.0. The ratio of (4,4 MDI) to 2,4-MDI) is approximately 2.5:1. A difunctional polyol made from a 70:30 mole ratio of polycaprolactone and polyglycolic acid with a molecular weight of 2,040 Daltons was used as the polyol component and was a viscous liquid at 25° C. Distilled water was used as the blowing agent. The catalysts used were the amines triethylene diamine (33% by weight in dipropylene glycol; DABCO 33LV from Air Products) and bis(2 dimethylaminoethyl) ether (23% by weight in dipropylene glycol; NIAX A-133 from Momentive Performance Chemicals). Silicone-based surfactants TEGOSTAB BF 2370, TEGOSTAB B5055, AND TEGOSTAB B8300 (from Evonik Degussa) were used for cell stabilization. A cell-opener was used (ORTEGOL 501 from Evonik Degussa). The proportions of the ingredients that were used are given as Form C9 in Table F below.

A number of reticulated partially resorbable reticulated elastomeric matrices using different caprolactone polyol (Arch Chemicals) made in conjunction with various diluents and caprolactone/glycolide copolymer polyol (custom prepared by Purac, Netherlands) were made by the procedure described above in this example used for Form C9. The proportions of the ingredients that were used for the various formulations and the measured T=0 properties (using methods described in Examples 1 and 2) are provided as Formulations (Form C10 to C13) in Table F below:

TABLE F

| Formulation | Form C9 | Form C10 | Form C11 | Form C12 | Form C13 |
|---|---|---|---|---|---|
| Polyol Composition | Caprolactone Polyol | Caprolactone/Glycolide 70/30 mole % Polyol | Caprolactone Polyol | Caprolactone Polyol | Caprolactone/Glycolide 70/30 mole % Polyol |
| Polyol Mol. Wt. | 2040 | 1986 | 2040 | 2040 | 1986 |
| Polyol | 100.00 | 100.00 | 100.00 | 100.00 | 100.00 |
| Aromatic Isocyante with f = 2.3 (apprx) (MONDUR 1488) | | | | | 57.9 |
| Aromatic Isocyante with f = 2.0 (MONDUR MQL) | 59.3 | 59.2 | 59.5 | 59.5 | |
| Diluent/Additive | | | Gelatin (collagen) 15 | Agar (starch) 15 | |
| Glycerin (external cross-linker) | 1.00 | 1.00 | 1.00 | 1.00 | |

TABLE F-continued

| Formulation | Form C9 | Form C10 | Form C11 | Form C12 | Form C13 |
|---|---|---|---|---|---|
| Water | 3.00 | 3.00 | 3.00 | 3.00 | 3.00 |
| 1,4 BDO (chain xtender) | — | — | — | — | — |
| Cell Opener | — | — | — | — | 1.00 |
| Surfactant 1 | 0.50 | 0.50 | 0.50 | 0.50 | 0.50 |
| Surfactant 2 | 1.25 | 1.50 | 1.25 | 1.25 | 1.50 |
| Surfactant 3 | 1.25 | 1.50 | 1.25 | 1.25 | 1.50 |
| Catalyst 1 | 0.65 | 0.65 | 0.70 | 0.70 | 0.40 |
| Catalyst 2 | 0.65 | 0.20 | 0.70 | 0.70 | 0.20 |
| Catalyst 3 | 0.25 | 0.20 | 0.50 | 0.50 | — |
| Catalyst 4 | 0.15 | 0.10 | 0.30 | 0.30 | — |
| Properties at T = 0. | | | | | |
| % Hard Segment | 34.82% | 34.80% | 31.83% | 31.83% | 33.76% |
| Permeability (Darcy) | 789 | 196 | 175 | 535 | 499 |
| Cell Size (mm) | 904 | 335 | 410 | 635 | 827 |
| Density (pcf)* | 1.90 | 3.95 | 2.27 | 2.25 | 3.03 |
| Comp Str. (psi)* | 0.36 | 1.63 | 0.54 | 0.53 | 1.32 |
| Tensile Max Load para (N)* | 11 | 9 | 10 | 8 | 18 |
| Elongation para (%)* | 467 | 209 | 355 | 262 | 196 |
| Density (pcf) | 1.96 | 3.50 | 2.31 | 2.33 | 3.12 |
| Comp Str. (psi) | 0.34 | 2.11 | 0.46 | 0.49 | 1.48 |
| Tensile Max Load para (N) | 13 | 8 | 11 | 8 | 19 |
| Tensile Stress (psi) | 29.9 | 18.4 | 25.3 | 18.4 | 43.7 |
| Elongation para (%) | 454 | 175 | 367 | 242 | 166 |

All data in Table F are for non-sterilized formulations. The high values of elongation to break (>150%) for all formulations demonstrate the elastomeric nature of these scaffolds.

Formulations C10 and C13 containing Caprolactone/Glycolide 70/30 mole % Polyol with two different isocyanates with f=2.3 and 2.0 were also gamma sterilized using 2.5 kGy.

The resorbable reticulated elastomeric matrices were subjected to in vitro aging at physiological pH of about 7.3 and at an accelerated degradation characteristic of 50° C. by the process described in Example 3.

At T=0, tensile load and elongation for non sterilized MDI (f=2.0)–PCL/PGA (C10) is 8N and 175%, after 2 months in-vitro exposure at 50° C., tensile load and elongation dropped to 0 and 7% showing complete in vitro degradation.

At T=0, tensile load and elongation for Gamma sterilized MDI (f=2.0)–PCL/PGA (C10) is 9N and 209%, after 2 months in-vitro exposure at 50° C., tensile load and elongation dropped to 0 and 0% showing complete in vitro degradation.

At T=0, tensile load and elongation for MDI (f'2.3)–PCL/PGA (C13) is 19N and 166%, after 2 months in-vitro exposure at 50° C., tensile load and elongation dropped to 5N and 36% showing substantial in vitro degradation At T=0, tensile load and elongation for Gamma Sterilized MDI (f=2.3)–PCL/PGA (C13) is 18N and 196%, after 2 months in-vitro exposure at 50° C., tensile load and elongation dropped to 2N and 14% at 50° C. in-vitro showing substantial in vitro degradation.

Matrices (C10) with MDI with f=2.0 (i.e. with no cross-linking) degrades faster in vitro than matrices (C13) with MDI with f=2.3 (i.e. with cross-linking) showing that cross-linking can be used to control degradation rates of reticulated degradable urethanes. Also eliminating chain extender, BDO, has helped in accelerating in vitro degradation for both C10 and C13.

The gamma sterilization had no effect of T=0 tensile properties for C13. However as observed with matrices (C13) with MDI with f=2.3, gamma sterilization causes faster drop in properties compared to non-gamma sterilized matrices showing that gamma sterilization can be used to control degradation rates of reticulated degradable urethanes.

The 90% recovery time following 75% compression for 10 minutes for MDI (f=2.0)–PCL/PGA (C10) is 2 minutes and for MDI (f=2.3)–PCL/PGA (C13) is 3 minutes.

Example 7

Synthesis and Properties of Degradable Reticulated Elastomeric Matrix Containing Caprolactone/Polyethylene Glycol Copolymer Polyol A reticulated partially resorbable reticulated elastomeric matrices using caprolactone/polyethylene glycol block copolymer polyol (custom prepared by Purac, Netherlands) and Aromatic Isocyante with f=2.0 (MONDUR MQL) was made by the procedure described in Example 2. The proportions of the ingredients are provided in Table G below:

TABLE G

| Formulation | Form C6 |
|---|---|
| Polyol Composition | Polycaprolactone/PEG Polyol |
| Polyol Mol. Wt. | 1900 |
| Polyol | 100.00 |
| Aromatic Isocyante with f = 2.0 (MONDUR MQL) | 59.3 |
| Glycerin (external cross-linker) | 1.00 |
| Water | 3.00 |
| 1,4 BDO (chain extender) | 0.0 |
| Cell Opener | 1.00 |
| Surfactant 1 | 1.00 |
| Surfactant 2 | 1.00 |
| Surfactant 3 | 1.00 |

TABLE G-continued

| Formulation | Form C6 |
|---|---|
| Catalyst 1 | 0.75 |
| Catalyst 2 | 0.75 |
| Catalyst 3 | 0.75 |
| Catalyst 4 | 0.75 |

The entire disclosure of each and every U.S. patent and patent application, each foreign and international patent publication and each other publication, and each unpublished patent application that is referenced in this specification, or elsewhere in this patent application, is hereby specifically incorporated herein, in its entirety, by the respective specific reference that has been made thereto.

While illustrative embodiments of the invention have been described above, it is understood that many and various modifications will be apparent to those in the relevant art, or may become apparent as the art develops. Such modifications are contemplated as being within the spirit and scope of the invention or inventions disclosed in this specification.

Industrial Utility

This invention has industrial applicability in providing hydrolytically-cleavable polyurethane foams, methods of their manufacture, and devices fabricated therefrom.

Incorporation By Reference

Throughout this application, various references including publications, patents, and pre-grant patent application publications are referred to. Disclosures of these publications in their entireties are hereby incorporated by reference into this application to more fully describe the state of the art to which this invention pertains. It is specifically not admitted that any such reference constitutes prior art against the present application or against any claims thereof. All publications, patents, and pre-grant patent application publications cited in this specification are herein incorporated by reference, and for any and all purposes, as if each individual publication or patent application were specifically and individually indicated to be incorporated by reference. In the case of inconsistencies the present disclosure will prevail.

The invention claimed is:

1. A reticulated matrix comprising (a) a soft segment comprising a polycaprolactone copolymer polyol and (b) a hard segment comprising an isocyanate having cross-linking and optionally having a chain extender, the reticulated matrix having a continuous-interconnected void phase, wherein the reticulated matrix is configured to be implantable and at least partially degradable, wherein the continuous-interconnected void phase extends from an interior portion to an exterior surface of said matrix; wherein a path through the void phase can be drawn in a substantially linear direction across an entirety of said matrix beginning at any portion of an exterior surface of said matrix containing said void phase.

2. The reticulated matrix of claim 1, wherein the reticulated matrix is substantially fully degradable.

3. The reticulated matrix of claim 1, wherein the reticulated matrix comprises a cross-linked polycaprolactone polyurethane-urea or a polycaprolactone polyurethane.

4. The reticulated matrix of claim 1, wherein the hard segment comprises aromatic and/or aliphatic isocyanate and the soft segment comprises polyester polyol, polycaprolactone polyol, a poly(caprolactone-co-glycolide)polyol, a poly(caprolactone-co-l-lactide) polyol, a poly(caprolactone-co-d-l-lactide)polyol, poly(caprolactone-co-paradioxanone polyol poly(caprolactone-co-glycolide-co-lactide)polyol, poly(caprolactone-co-glycolide-co-d/l lactide)polyol, poly (caprolactone-co-lactide-co-d/lactide)polyol, a poly(caprolactone-co-polyethylene glycolide)polyol or their appropriate combinations.

5. The reticulated matrix of claim 1, wherein the reticulated matrix comprises a reticulated, resiliently-compressible, elastomeric matrix that promotes tissue ingrowth and comprises a continuous network of intercommunicating and interconnected solid void space, wherein said void space comprises a plurality of interconnected cells and pores that are fully accessible.

6. The reticulated matrix of claim 1, wherein the reticulated matrix is biocompatible and conducive to allow for fluid transfer, tissue ingrowth, regeneration and re- modeling with bio-integration to wound or defect site to heal tissue defect.

7. The reticulated matrix of claim 1, wherein hydrolytic of the reticulated matrix degradation rates are controllable through multiple different mechanisms.

8. The reticulated matrix of claim 1, wherein hydrolytic of the reticulated matrix are controllable by the composition of polyol-derived soft segments, molecular weight of the polyol-derived soft segments, relative molecular weights of the copolymers of the polyol-derived soft segments, degree and extent of cross-linking, degree and extent of chain extension, application of gamma sterilization or combinations thereof.

9. A process of making a reticulated matrix comprising a foaming by reacting isocyanate with polyol in presence of a blowing agent to form a porous reaction product, and thermally reticulating of the porous matrix to form the reticulated matrix, wherein the reticulated matrix is configured to be implantable and at least partially degradable wherein the reticulated matrix having a continuous-interconnected void phase, wherein the continuous-interconnected void phase extends from an interior olio to an exterior surface of said matrix; wherein a path through the void phase can be drawn in a substantially linear direction across an entirety of said matrix beginning at any portion of an exterior surface of said matrix containing said void phase.

10. The process of claim 9, wherein the foaming comprises reacting (a) a soft segment comprising a polycaprolactone copolymer polyol and (b) a hard segment comprising an isocyanate having cross-linking and optionally having a chain extender.

11. The process of claim 9, wherein the reticulated matrix comprises a cross-linked polycaprolactone polyurethane-urea or a polycaprolactone polyurethane.

12. The process of claim 11, wherein the hard segment comprises aromatic and/or aliphatic isocyanate and the soft segment comprises polyester polyol, polycaprolactone polyol, a poly(caprolactone-co-glycolide)polyol, a poly(caprolactone-co-l-lactide)polyol, a poly(caprolactone-co-d-l-lactide)polyol, poly(caprolactone-co-paradioxanone polyol poly(caprolactone-co-glycolide-co-lactide)polyol, poly(caprolactone-co-glycolide-co-d/l lactide)polyol, poly(caprolactone-co-lactide-co-d/l lactide)polyol, a poly(caprolactone-co-polyethylene glycolide)polyol or their appropriate combinations.

13. The process of claim 9, wherein during the foaming, gelation occurs such that the porous reaction product has dimension structural stability.

14. The process of claim 13, wherein the reticulated matrix post said gelation contains ruptured cell membranes and cell windows for substantially continuous passage of combustion gases during reticulation.

15. The process of claim 9, wherein the reticulated matrix comprises a reticulated, resiliently-compressible, elastomeric matrix that promotes tissue ingrowth and comprises a continuous network of intercommunicating and inter-connected solid void space, wherein said void space comprises a plurality of interconnected cells and pores that are fully accessible.

16. The process of claim 9, wherein hydrolytic degradation rates of the reticulated matrix are controllable through multiple different mechanisms.

17. The process of claim 9, wherein the foaming comprises reacting (a) a soft segment comprising a polycaprolactone copolymer polyol and (b) a hard segment comprising an isocyanate having cross-linking and optionally having a chain extender.

\* \* \* \* \*